US008765720B2

(12) United States Patent
Berenson

(10) Patent No.: US 8,765,720 B2
(45) Date of Patent: Jul. 1, 2014

(54) COMBINATION THERAPY FOR THE TREATMENT OF MULTIPLE MYELOMA

(75) Inventor: James R. Berenson, Beverly Hills, CA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 13/292,553

(22) Filed: Nov. 9, 2011

(65) Prior Publication Data

US 2012/0071445 A1    Mar. 22, 2012

Related U.S. Application Data

(63) Continuation of application No. PCT/US2009/067174, filed on Dec. 8, 2009, which is a continuation of application No. PCT/US2009/003467, filed on Jun. 9, 2009.

(60) Provisional application No. 61/232,594, filed on Aug. 10, 2009, provisional application No. 61/185,501, filed on Jun. 9, 2009, provisional application No. 61/181,550, filed on May 27, 2009.

(51) Int. Cl.
*A61K 31/69* (2006.01)

(52) U.S. Cl.
USPC .......................................................... 514/64

(58) Field of Classification Search
USPC .......................................................... 514/64
See application file for complete search history.

(56) References Cited

U.S. PATENT DOCUMENTS

| | | | | | |
|---|---|---|---|---|---|
| 6,066,730 | A | * | 5/2000 | Adams et al. | .................... 544/69 |
| 2005/0107307 | A1 | * | 5/2005 | Bernadini et al. | ............... 514/19 |
| 2006/0030547 | A1 | | 2/2006 | Dukart et al. | |
| 2006/0172978 | A1 | | 8/2006 | Russell et al. | |
| 2006/0252740 | A1 | | 11/2006 | Johnson et al. | |
| 2007/0265230 | A1 | | 11/2007 | Rousso et al. | |

FOREIGN PATENT DOCUMENTS

| WO | WO 2008091620 A2 * | 7/2008 | .............. A61K 31/69 |
|---|---|---|---|
| WO | WO 2009/061345 A2 | 5/2009 | |

OTHER PUBLICATIONS

Richardson, Paul G., et al. A Phase II study of Bortezomib in Relapsed, Refractory Myeloma. The New England Journal of Medicine. 348, pp. 2609-2618, published Jun. 26, 2003.*
Berenson, James R. et al. Phase I/II Trial Assessing Bortezomib and Melphalan Combination Therapy for the Treatment of Patients With Relapsed or Refractory Multiple Myeloma. Journal of Clinical Oncology 24, 937-945. Published Feb. 20, 2006.*
Reagan-Shaw, S. et al. Dose Translation from animal to human studies revisited. FASEB Journal. 22, 659-661, Published 2007.*
Piva, Roberto et al. CEP-18770: A novel, orally active proteasome inhibitor with a tumor-selective pharmacologic profile competitive with bortezomib. Blood 111, 2765-2775. Prepublished online Dec. 5, 2007.*
Berenbaum, M.C., et al. Synergy, additivism and antagonism in immunosuppression: A critical review. Clin. Exp. Immunol. vol. 28 pp. 1-18. Published 1977.*
Chou, T.C. Drug Combination Studies and Their Synergy Quantification Using the Chou-Talalay Method. Cancer Research. vol. 70 pp. 440-446. Published 2010.*
Piva, R. et al. Blood vol. 111 pp. 2765-2777. Published online Dec. 2007.*
Chauhan. D. et al., Blood. vol. 103, pp. 3158-3166. Published online Dec. 2003.*
Ahn et al., "Salinosporamide A (NPI-0052) potentiates apoptosis, suppresses osteoclastogenesis, and inhibits invasion through down-modulation of NF-KB-regulated gene products", *Blood* (2007), 110, pp. 2286-2295.
ALKERAN® for Injection, Prescribing Information (2008), pp. 1-9.
ALKERAN® Tablets, Prescribing Information (2008), pp. 1-8.
Argyriou et al., "Bortezomib-induced peripheral neuropathy in multiple myeloma: a comprehensive review of the literature", *Blood* (2008), 112, pp. 1593-1599.
Berenson et al., "Safety and efficacy of bortezomib and melphalan combination in patients with relapsed or refractory multiple myeloma: updated results of a phase ½ study after longer follow-up", *Ann. Hematol.* (2008), 87, pp. 623-631.
Berenson et al., "Phase I/II Trial Assessing Bortezomib and Melphalan Combination Therapy for the Treatment of Patients With Relapsed or Refractory Multiple Myeloma", *J. Clin. Oncol.* (2006), 24, pp. 937-944.
Bianchi et al., "The proteasome load versus capacity balance determines apoptotic sensitivity of multiple myeloma cells to proteasome inhibition", *Blood* (2009), 113, pp. 3040-3049.
Bissery et al., "Experimental Antitumor Activity of Taxotere (RP56976, NSC628503), a Taxol Analogue", *Cancer Res.* (1991), 51, pp. 4845-4852.
Bold et al., "Chemosensitization of Pancreatic Cancer by Inhibition of the 26S Proteasome", *J. Sorg. Res.* (2001), 100, pp. 11-17.
Campbell et al., Antimyeloma effects of arsenic trioxide are enhanced by melphalan, bortezomib and ascorbic acid, *Br. J. Haematol.* (2007), 138, pp. 467-478.
Chauhan et al., "Mechanisms of cell death and survival in multiple myeloma (MM): Therapeutic implications", *Apoptosis* (2003), 8, pp. 337-343.
Chauhan et al., "Combination of proteasome inhibitors bortezomib and NPI-0052 trigger in vivo synergistic cytotoxicity in multiple myeloma", *Blood* (2008), 111, pp. 1654-1664.
Chauhan et al., "In Vitro and In Vivo Proteasome Activity Profiles of Bortezomib and a Novel Proteasome Inhibitor NPI-0052" (2005) Abstract 3363.
Chen et al., "The FA/BRCA pathway is involved in melphalan-induced DNA interstrand cross-link repair and accounts for melphalan resistance in multiple myeloma cells", *Blood* (2005), 106, pp. 698-705.

(Continued)

*Primary Examiner* — Paul Zarek
*Assistant Examiner* — George W Kosturko
(74) *Attorney, Agent, or Firm* — Baker & Hostetler LLP

(57) ABSTRACT

The present invention provides a method for treating multiple myeloma in a subject, comprising the step of administering to the subject a combination of COMPOUND 1 and bortezomib. The invention further provides a method for treating multiple myeloma in a subject, comprising the step of administering to the subject a combination of COMPOUND 1 and melphalan.

16 Claims, 28 Drawing Sheets

(56) References Cited

OTHER PUBLICATIONS

Chou, "Theoretical Basis, Experimental Design, and Computerized Simulation of Synergism and Antagonism in Drug Combination Studies", *Pharmacol. Rev.* (2006), 58, pp. 621-681.

Crawford et al., "Comparative Selectivity and Specificity of the Proteasome Inhibitors BzLLLCOCHO, PS-341 and MG-132", *Cancer Res.* (2006), 66, pp. 6379-6386.

Cusack et al., "Enhanced Chemosensitivity to CPT-11 with Proteasome Inhibitor PS-341: Implications for Systemic Nuclear Factor-KB Inhibition", *Cancer Res.* (2001), 61, pp. 3535-3540.

Demo et al., "Antitumor Activity of PR-171, a Novel Irreversible Inhibitor of the Proteasome", *Cancer Res.* (2007), 67, pp. 6383-6391.

Dorsey et al., "Discovery of a Potent, Selective, and Orally Active Proteasome Inhibitor for the Treatment of Cancer", *J. Med. Chem.* (2008), 51, pp. 1068-1072.

Hamburger et al., "Primary Bioassay of Human Myeloma Stem Cell", *J. Clin. Invest.* (1977), 60, pp. 846-854.

Hideshima et al., "Molecular Mechanisms of Novel Therapeutic Approaches for Multiple Myeloma", *Nat. Rev. Cancer* (2002), 2, pp. 927-937.

Hideshima et al., "The Proteasome Inhibitor Ps-341 Inhibits Growth, Induces Apoptosis, and Overcomes Drug Resistance in Human Multiple Myeloma Cells," *Cancer Res* (2001), 61, pp. 3071-3076.

Jacquemont et al., "Proteasome Function is Required for DNA Damage Response and Fanconi Anemia Pathway Activation", *Cancer Res.* (2007), 67, pp. 7395-7405.

Jagannath et al., "A phase 2 study of two doses of bortezomib in relapsed or refractory myeloma", *Br. J. Haematol.* (2004), 127, pp. 165-172.

Jemal et al., "Cancer Statistics, 2008", *CA Cancer J. Clin.* (2008), 58, pp. 71-96.

Ma et al., "The Proteasome Inhibitor PS-341 Markedly Enhances Sensitivity of Multiple Myeloma tumor Cells to Chemotherapeutic Agents", *Clin. Cancer Res.* (2003), 9, pp. 1136-1144.

Marangon et al., "Development of a HPLC-MS/MS assay to measure the novel proteasome inhibitor CEP-18770 in plasma. Preliminary pharmacokinetic evaluation in cancer patients", 57th ASMS Conference, Philadelphia, May 31-Jun. 4, 2009 (Poster).

Matsui et al., "Characterization of clonogenic multiple myeloma cells", *Blood* (2004), 103, pp. 2332-2336.

Matsui et al., Clonogenic Multiple Myeloma Progenitors, Stem Cell Properties, and Drug Resistance, *Cancer Res.* (2008), 68, pp. 190-197.

Meister et al., "Extensive Immunoglobulin Production Sensitizes Myeloma Cells for Protesome Inhibitors", *Cancer Res.* (2007), 67, pp. 1783-1792.

Mitsiades et al., "Trail/Apo2L ligand selective induces apoptosis and overcomes drug resistance in multiple myeloma: therapeutic applications", *Blood* (2001), 98, pp. 795-804.

Mitsades et al., "Apoptotic signaling induced by immunomodulatory thalidomide analogs in human multiple myeloma cells: therapeutic implications" *Blood* (2002), 99, pp. 4525-4530.

Mitsiades et al., "The proteasome inhibitors PS-341 potentiates sensitivity of multiple myeloma cells to conventional chemotherapeutic agents: therapeutic applications," *Blood* (2003), 101, pp. 2377-2380.

Mitsiades et al., "Molecular sequelae of proteasome inhibition in human multiple myeloma cells", *Proc. Nat'l, Acad. Sci.* (2002), 99, pp. 14374-14379.

Obeng et al., "Proteasome inhibitors induce a terminal unfolded protein response in multiple myeloma cells", *Blood* (2006), 107, pp. 4907-4916.

Pei et al., "Synergistic Induction of Oxidative Injury and Apoptosis in Human Multiple Myeloma Cells by the Proteasome Inhibitor Bortezomib and Histone Deacetylase Inhibitors", *Clin. Cancer Res.* (2004), 10, pp. 3839-3852.

Pineda-Roman et al., "VTD combination therapy with bortezomib-thalidomide-dexamethasone is highly effective in advanced and refractory multiple myeloma", *Leukemia* (2008), 22, pp. 1419-1427.

Piva et al., "CEP-18770: A novel, orally active proteasome inhibitor with a tumor-selective pharmacologic profile competitive with bortezomib", *Blood* (2008), 111, pp. 2765-2775.

Podar et al., "Targeting PKC in multiple myeloma: in vitro and in vivo effects of the novel, orally available small-molecular inhibitor enzastaurin (LY317615.HC1)", *Blood* (2007), 109, pp. 1669-1677.

Reagan-Shaw et al., "Dose translation from animal to human studies revisited" *FASEB Journal* (2007), 22, pp. 659-661.

Richardson et al., Bortezomib demonstrates superior survival compared with high-dose dexamethasone and higher response rates after extended follow-up in the Apex trial in relapse multiple myeloma *11th Congress of the European Hematology Assoc.* (2006), No. 0224.

Richardson et al., "A Phase 2 Study of Bortezomib in Relapsed, Refractory Myeloma", *New England J. Med.* (2003), 348, pp. 2609-2617.

Roccaro et al., "Bortezomib mediates antiangiogenesis in Multiple Myeloma via Direct and Indirect Effedts on Endothelial Cells", *Cancer Res.* (2006), 66, pp. 184-191.

Ruschak et al., Novel Proteasome Inhibitors to Overcome Bortezomib Resistance, *J. Nat'l Cancer Inst.* (2011), 103, pp. 1007-1017.

Sanchez et al., "Oral Dosing of the Novel Proteasome Inhibitor CEP-18770 shows Marked anti-Myeloma Effects in SCID-Hu Models of Multiple Myeloma", *Blood (ASH Annual Meeting Abstracts)* (2009), 114, Abstract 1840.

Sanchez et al., The proteasome inhibitor CEP-18770 enhances the anti-myeloma activity of bortezomib and melphalan, *Br. J. Haematol.* (2009), 148, pp. 569-581.

Sanchez et al., The Novel Proteasome Inhibitor CEP-18770 Inhibits Myeloma Tumor Growth in Vitro and in Vivo, and Enhances the Anti-MM Effects of Melphalan, Doxorubicin and Arsenic Trioxide, *ASH Oral Presentation*, Dec. 9, 2008.

Sanchez et al., The Novel Proteasome Inhbitor CEP-18770 Inhibits Myelom Tumor Growth in Vitro and in Vivo and Enhances the Anti-MM Effects of Melphalan, *Blood (ASH Annual Meeting Abstracts)* (2008), 112, Abstract 843.

San Miguel et al., "Updated Follow-Up and Results of Subsequent Therapy in the Phase III VISTA Trial: Bortezomib Plus Melphalan-Prednisone Versus Melphalan-Prednisone in Newly Diagnosed Multiple Myeloma", *Blood (Ash Annual Meeting Abstracts)* (2008), 112, Abstract 650.

Shah et al.,"26S proteasome inhibition induces apoptosis and limits growth of human pancreatic cancer", *J. Cellular Biochem.* (2001), 82, pp. 110-122.

Teicher et al., "The Proteasome Inhibitor PS-341 in Cancer Therapy", *Clin. Cancer Res.* (1999), 5, pp. 2638-2645.

Velcade for Injection, Prescribing Information (2008), pp. 1-34.

Zweegman et al., "Treatment of myeloma: recent developments", *Anti-Cancer Drugs* (2002), 13, pp. 339-351.

Baumann et al., Alkylating agents induce activation of NFKB in multiple myeloma cells, *Leukemia Research* (2008), 32, pp. 1144-1147.

Campbell et al., "Animal Models of Multiple Myeloma and Their Utility in Drug Discovery", *Current Protocols in Pharmacology* (2008), pp. 14.9.1-14.9.22.

Chauhan et al., "Chapter 12: Targeting Proteasomes as Therapy in Multiple Myeloma", *Advances Experimental Medicine and Biology* (2008), pp. 251-260.

Chou et al., "Quantitative Analysis of Dose-Effect Relationships: The Combined Effects of Multiple Drugs or Enzyme Inhibitors", *Adv Enzyme Regul.* (1984) pp. 27-55.

McConkey et al., "Mechanisms of proteasome inhibitor action and resistance in cancer", *Drug Resistance Updates* (2008), 11, pp. 164-179.

Pilarski et al., "Leukemic B cells clonally identical to myeloma plasma cells are myelomagenic in NOD/SCID mice", *Experimental Hematology* (2002), 30, pp. 221-228.

Pink, #787, PS-341 "Enhances chemotherapeutic effect in human xenograft models", *Proceedings of the American Assoc. for Cancer Research* (2002), 43, p. 158.

Sunters et al., "The Cytotoxicity, DNA Crosslinking Ability and DNA Sequence Selectivity of the Aniline Mustards Melphalan, Chlorambucil and 4-[Bis(2-Chloroethyl)amino] Benzoic Acid", *Biochem. Pharmacology* (1992), 44(1), pp. 59-64.

\* cited by examiner

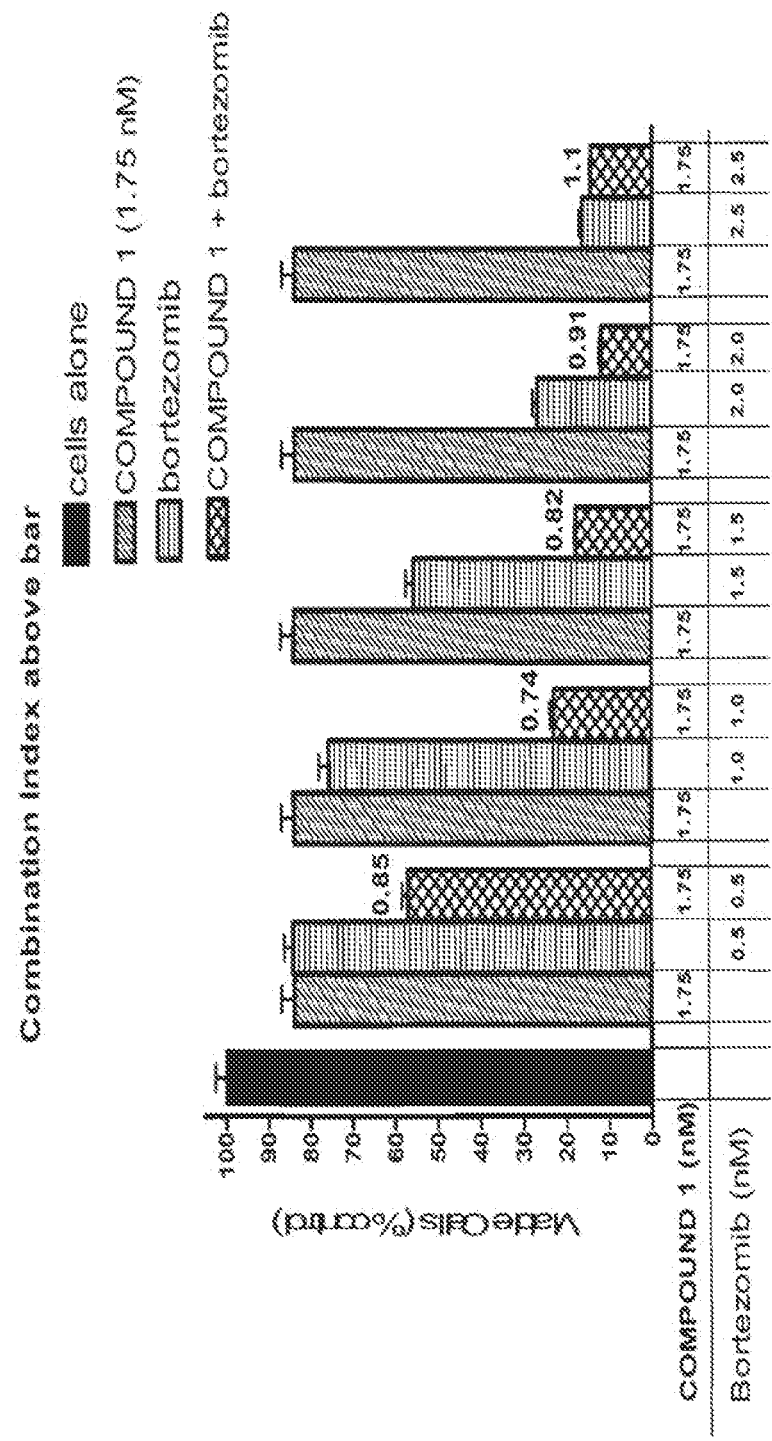

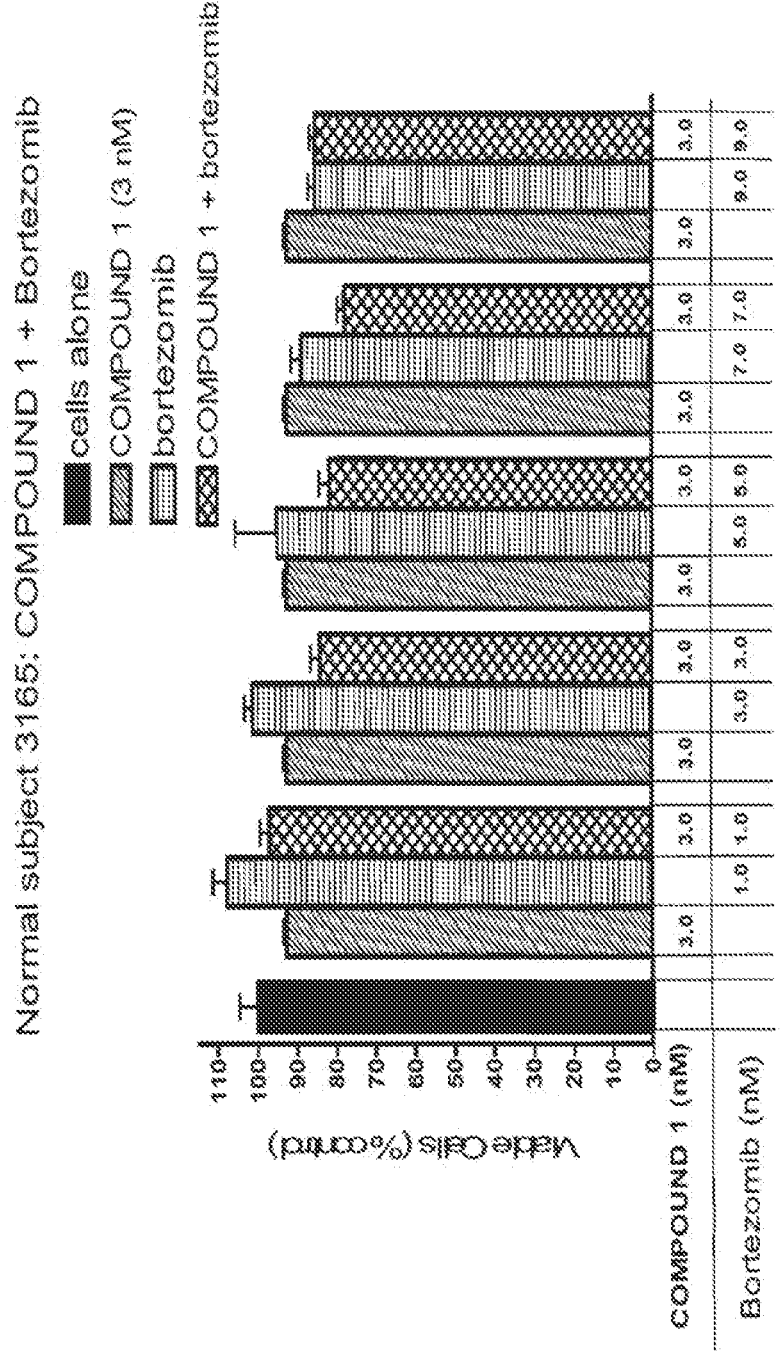

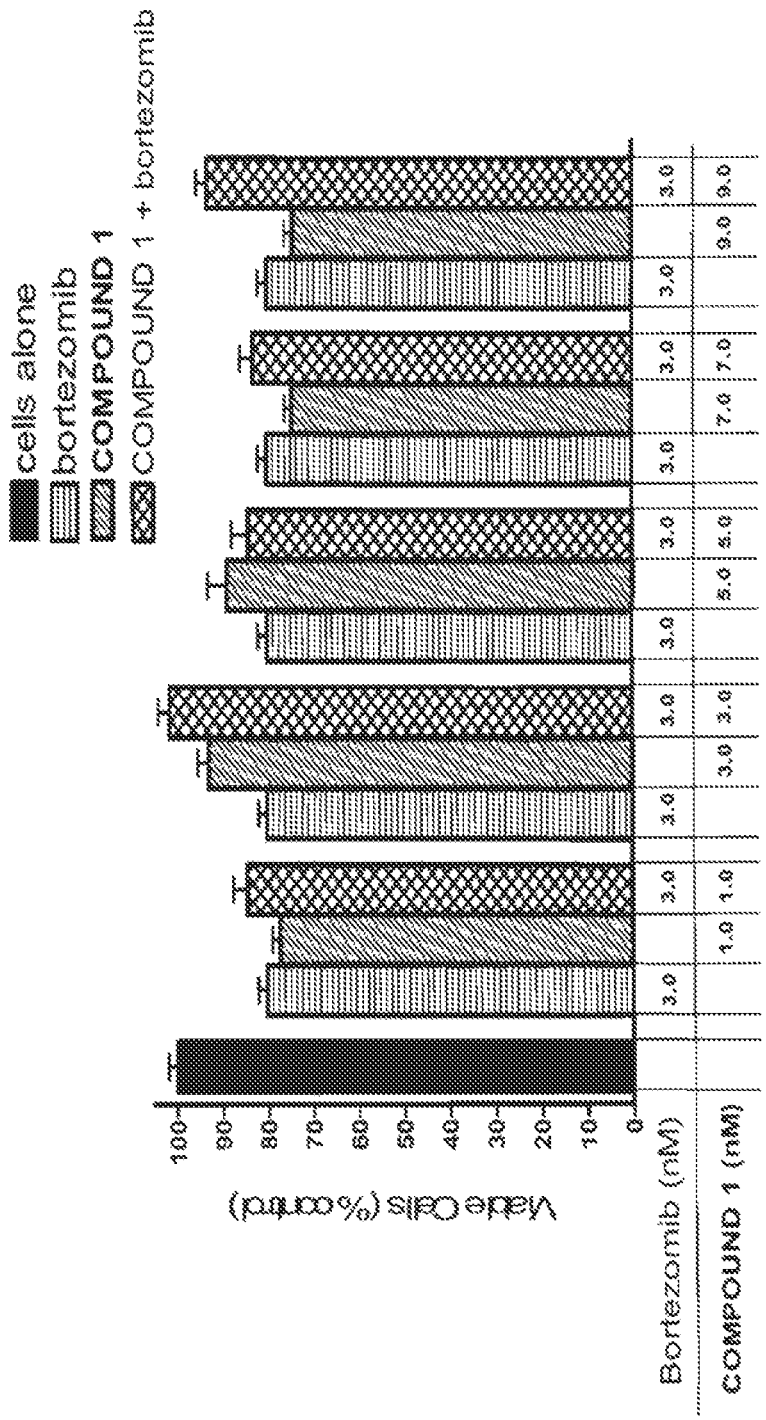

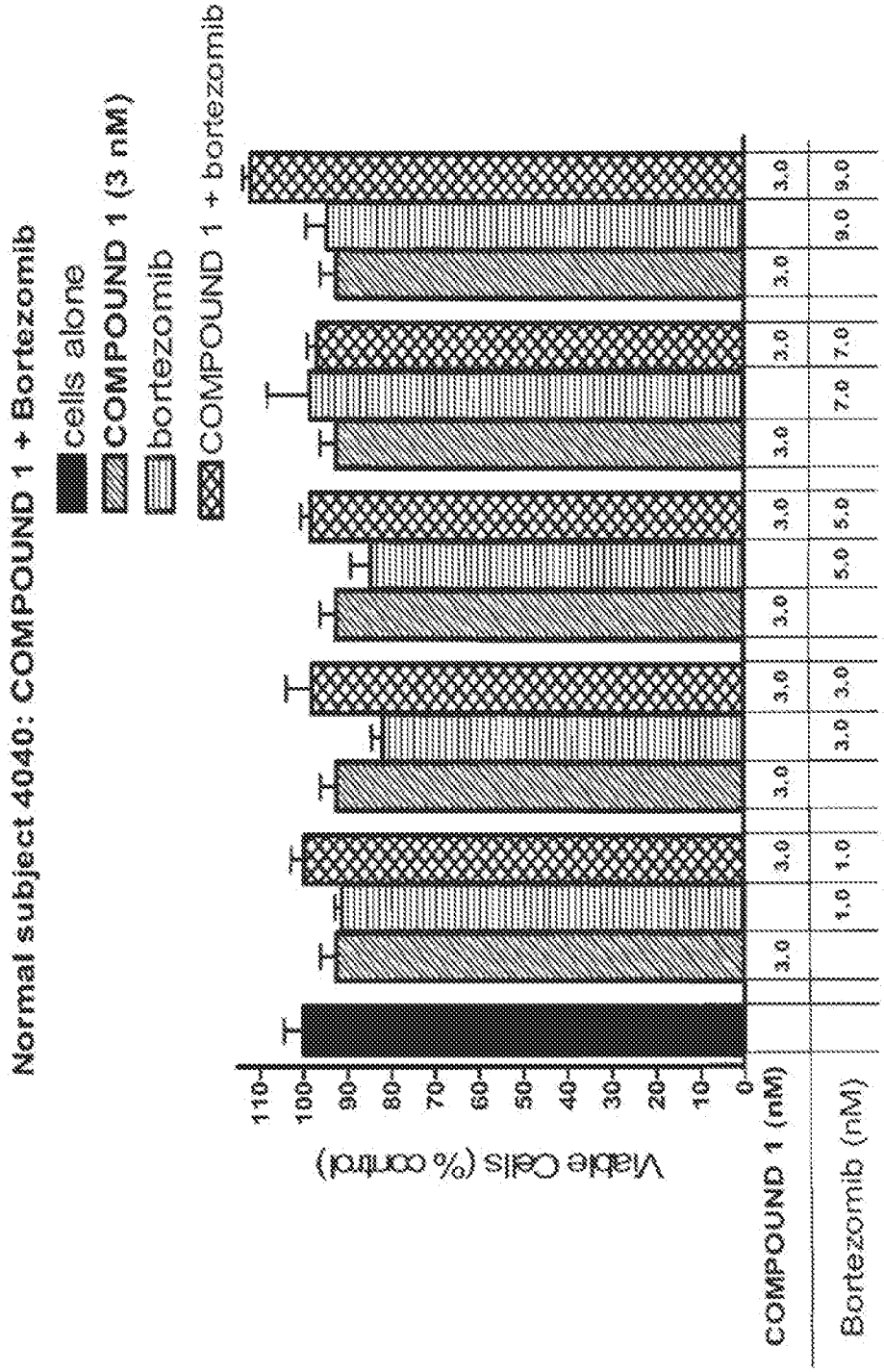

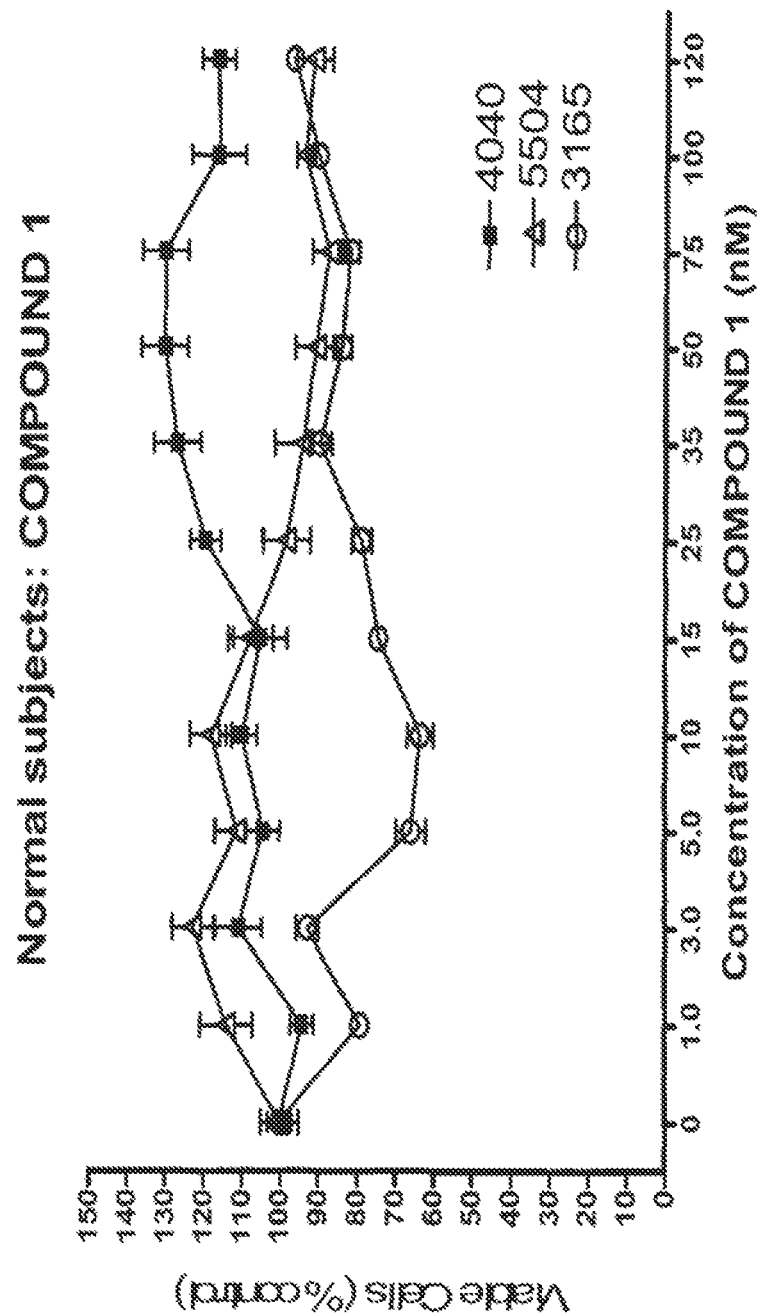

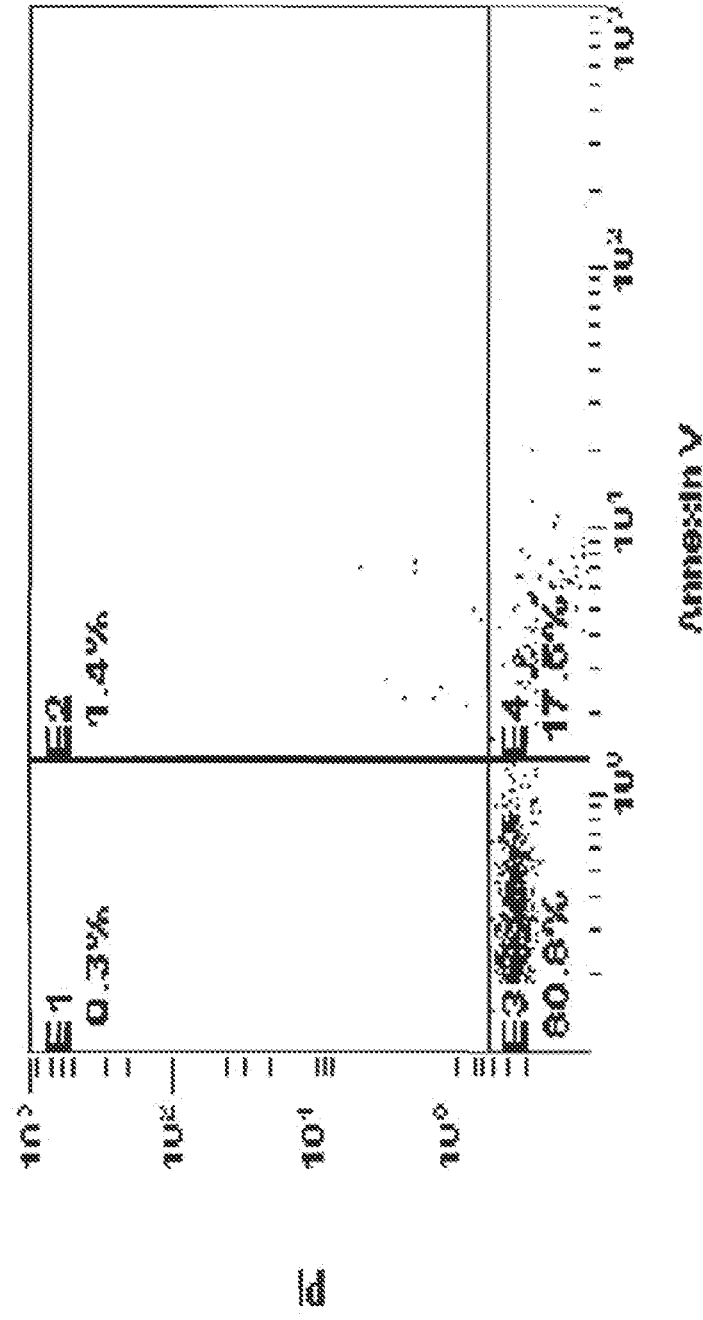

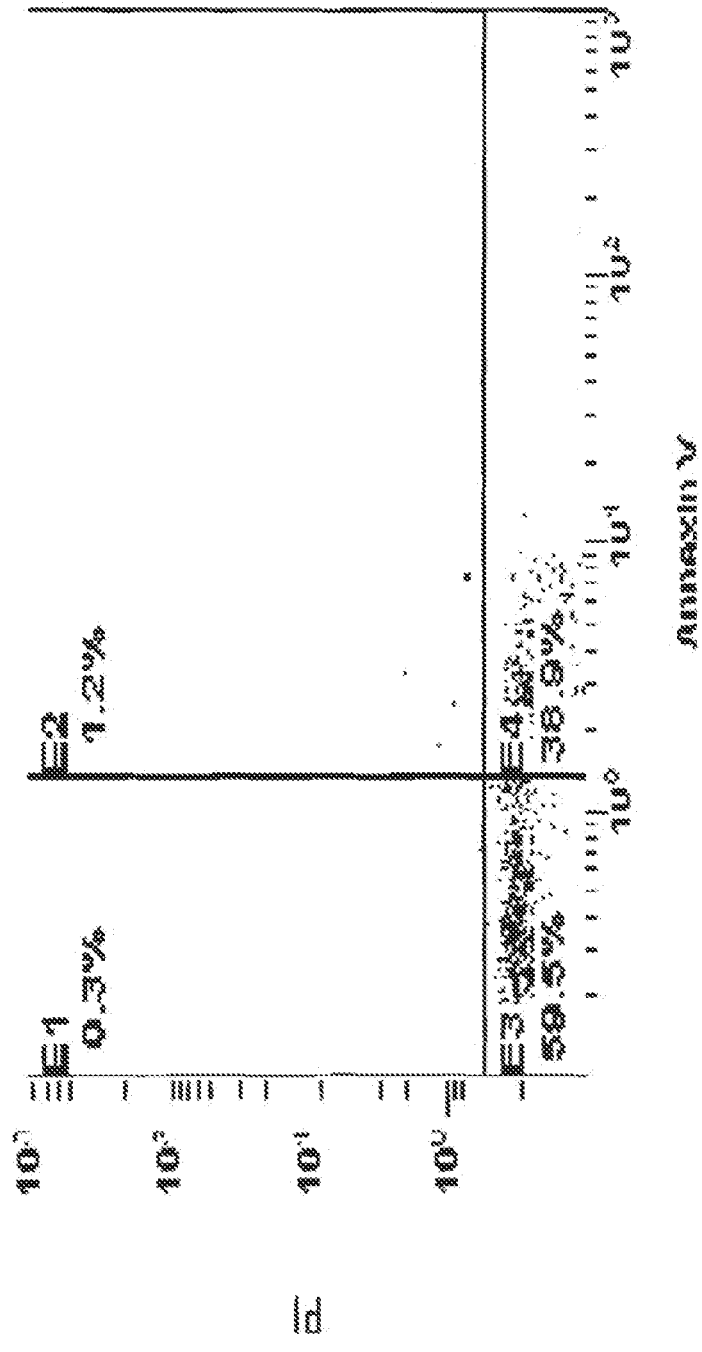

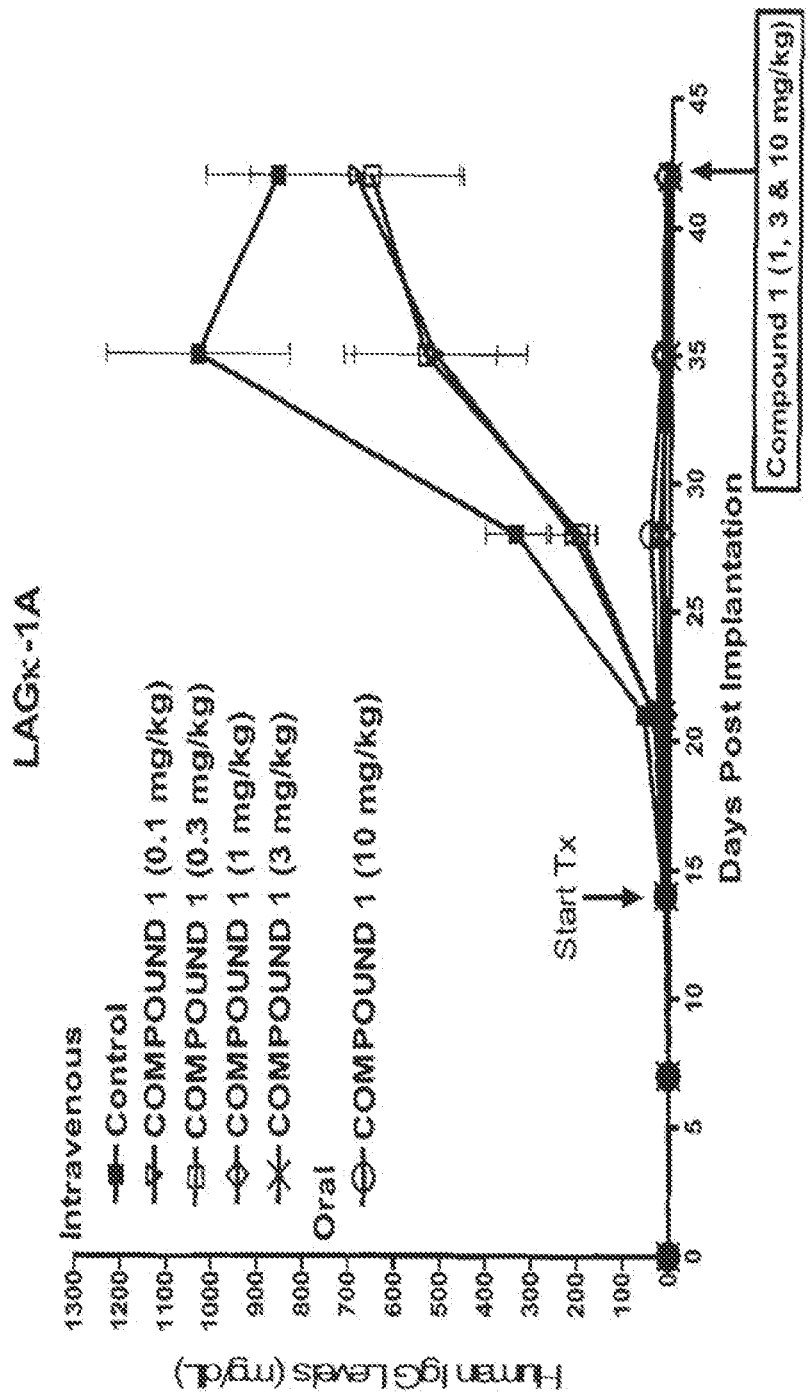

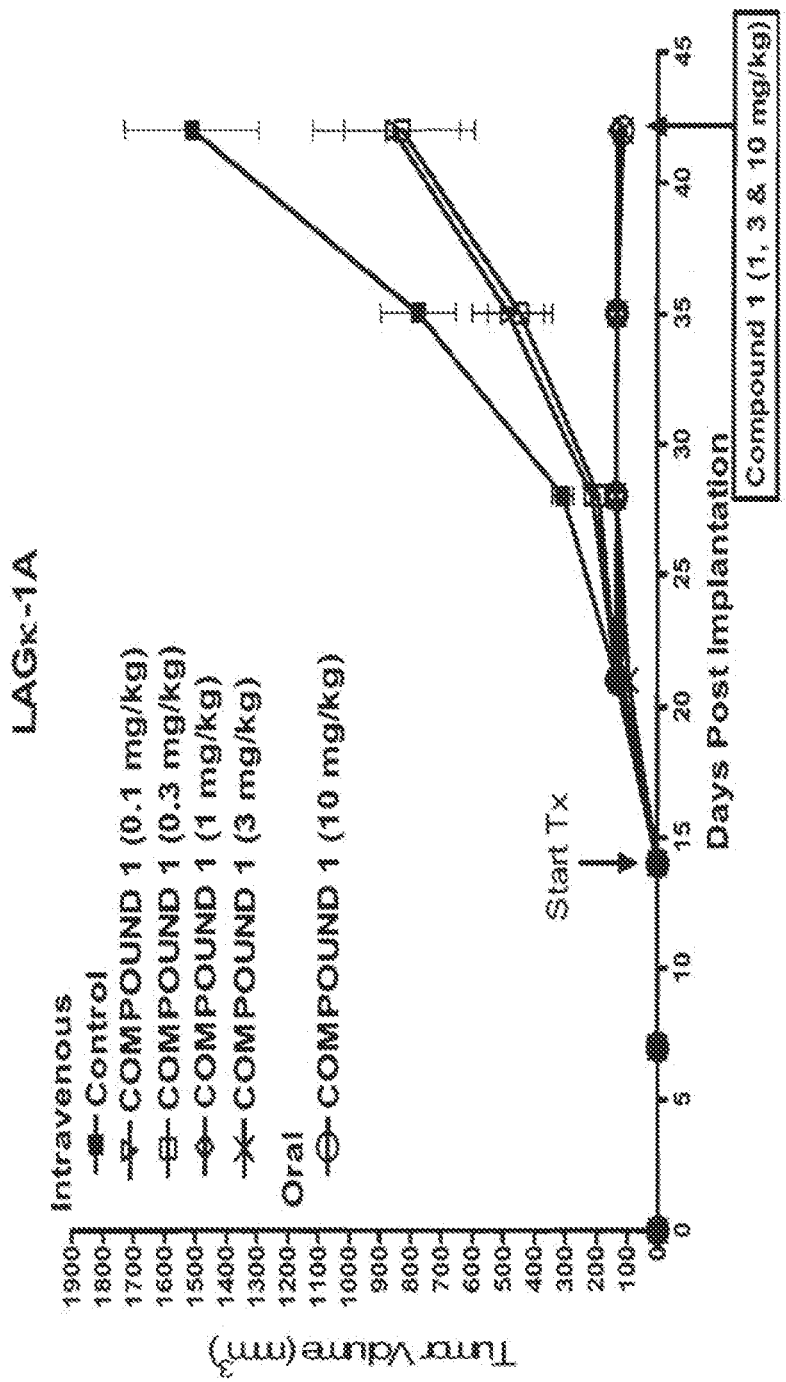

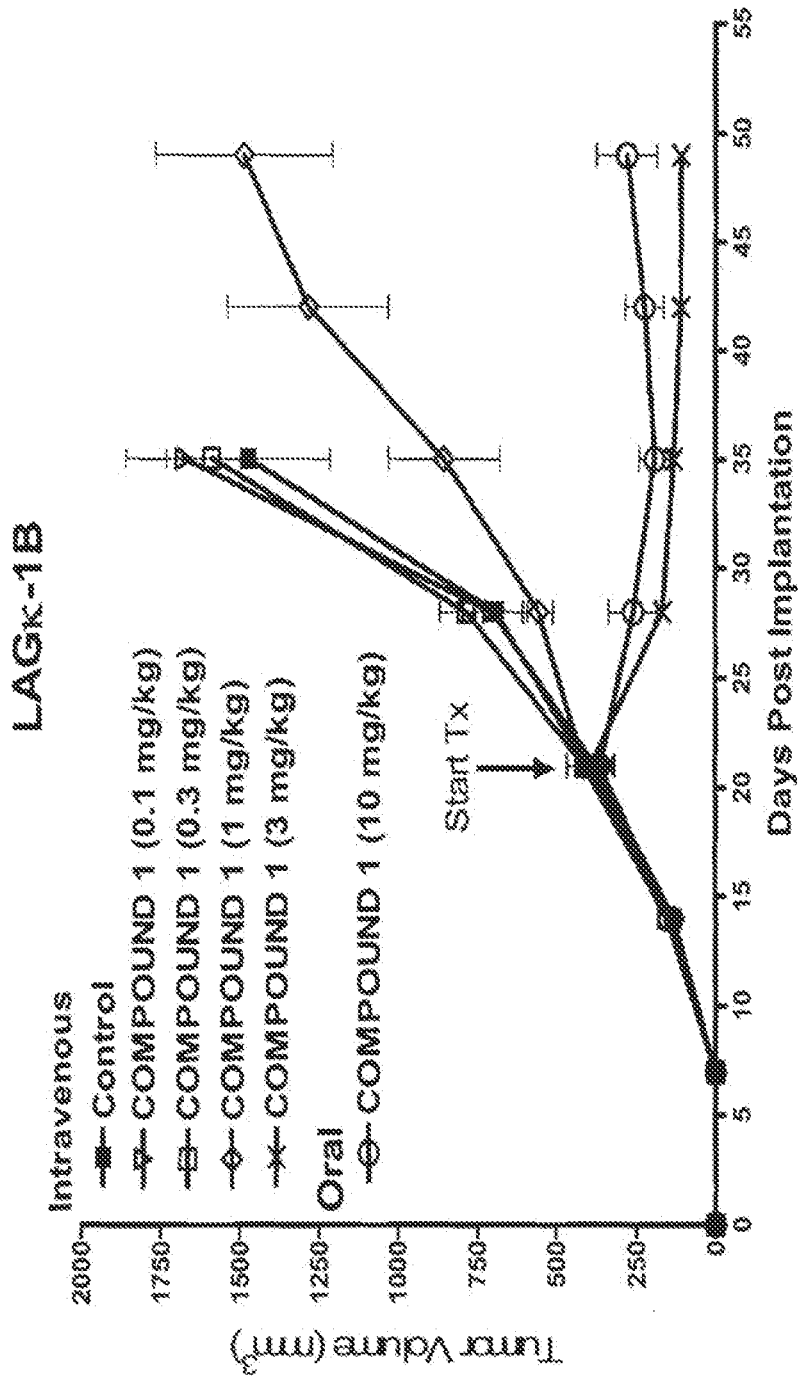

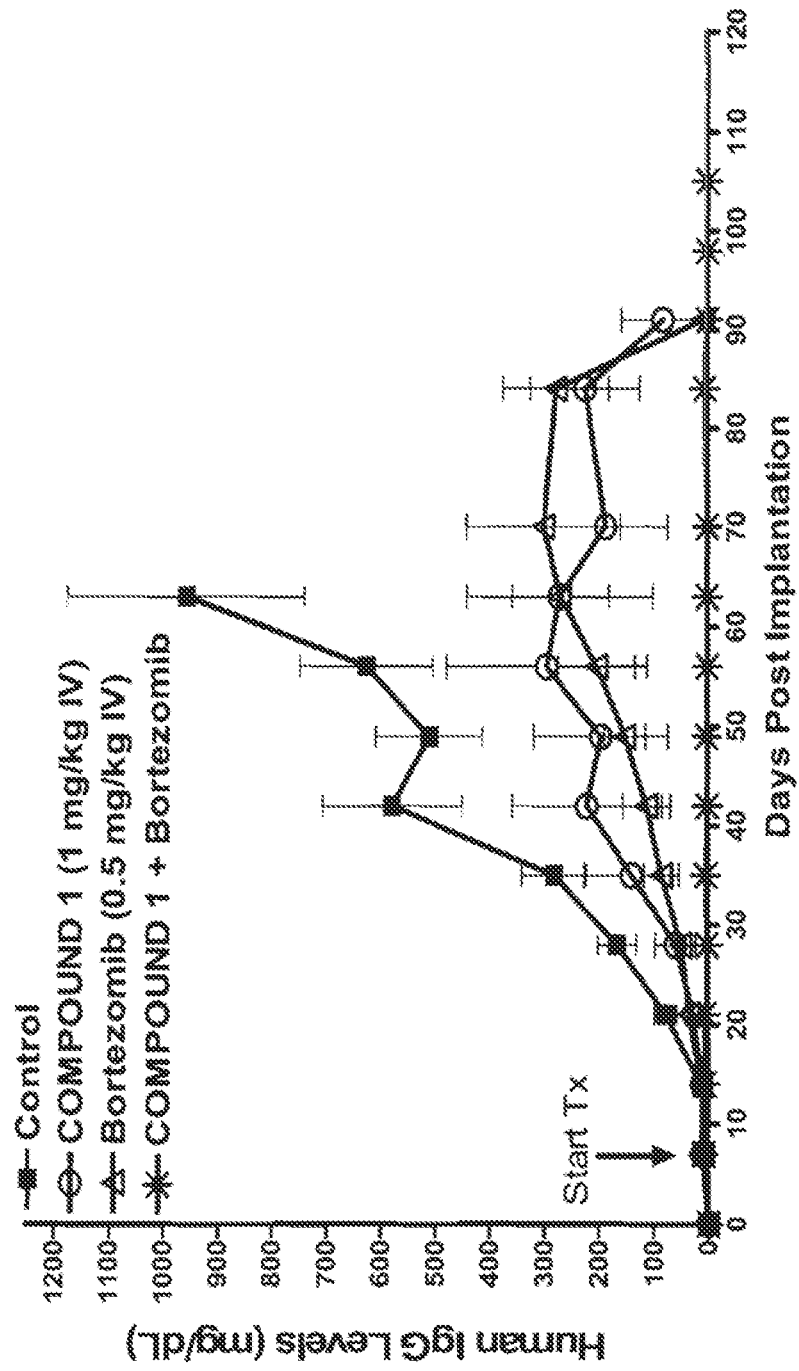

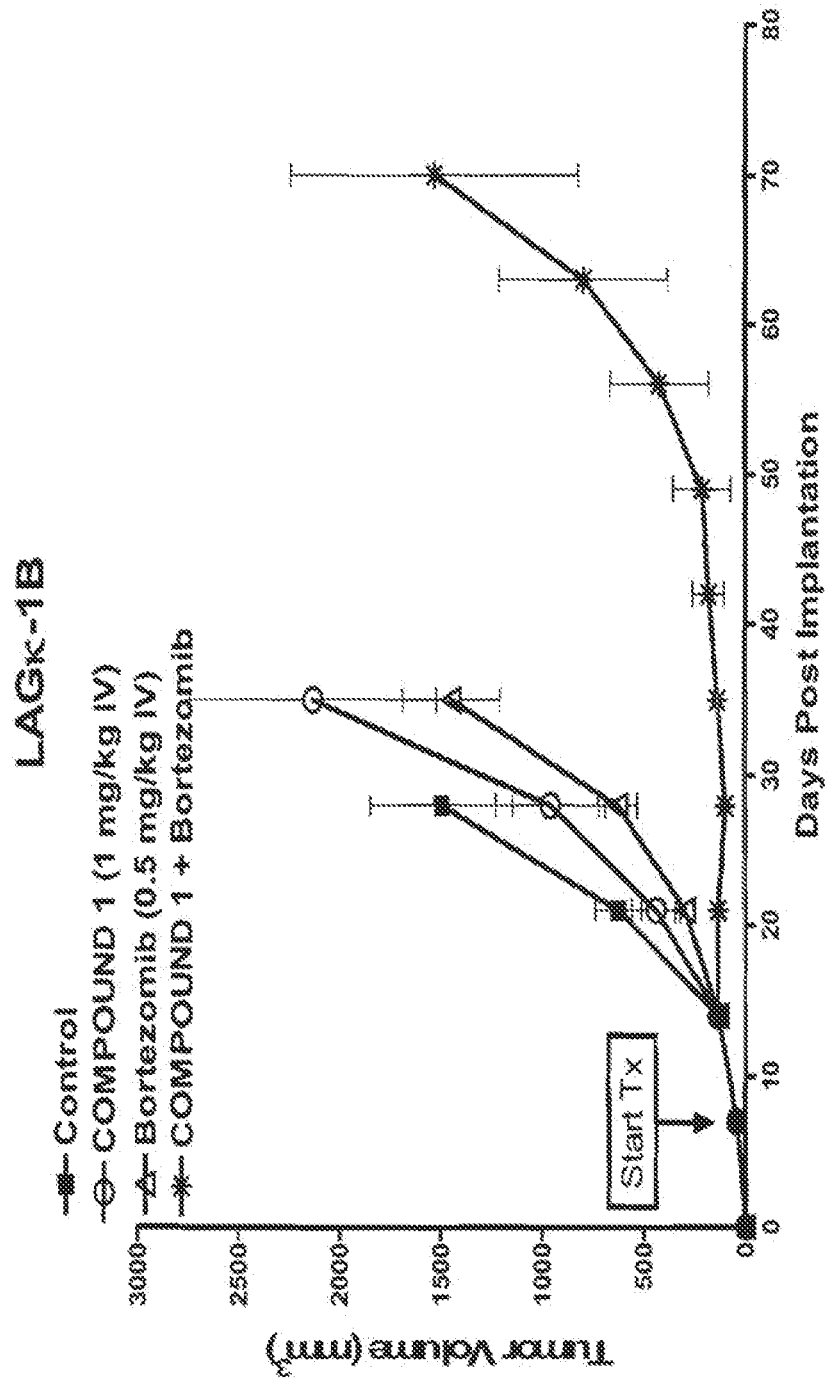

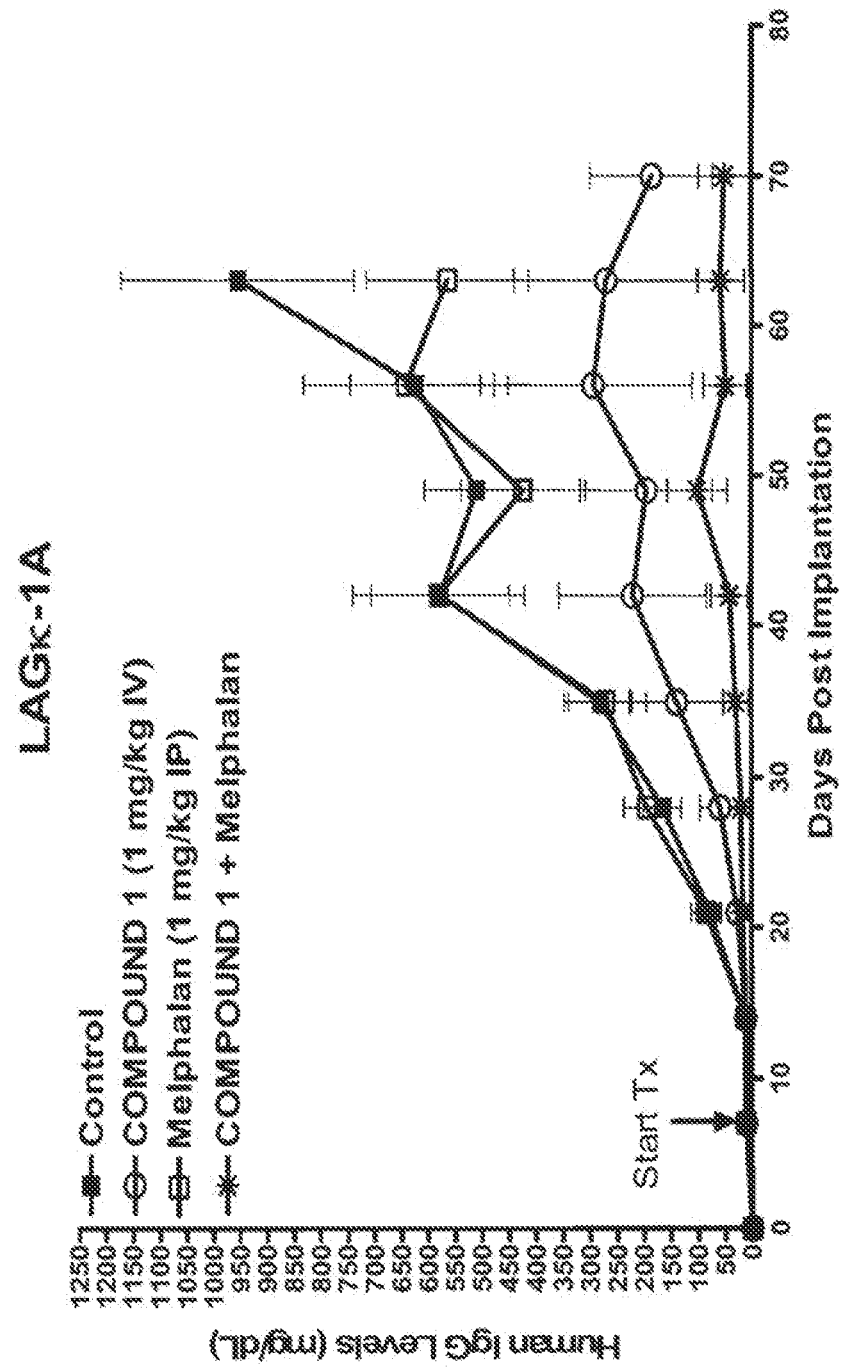

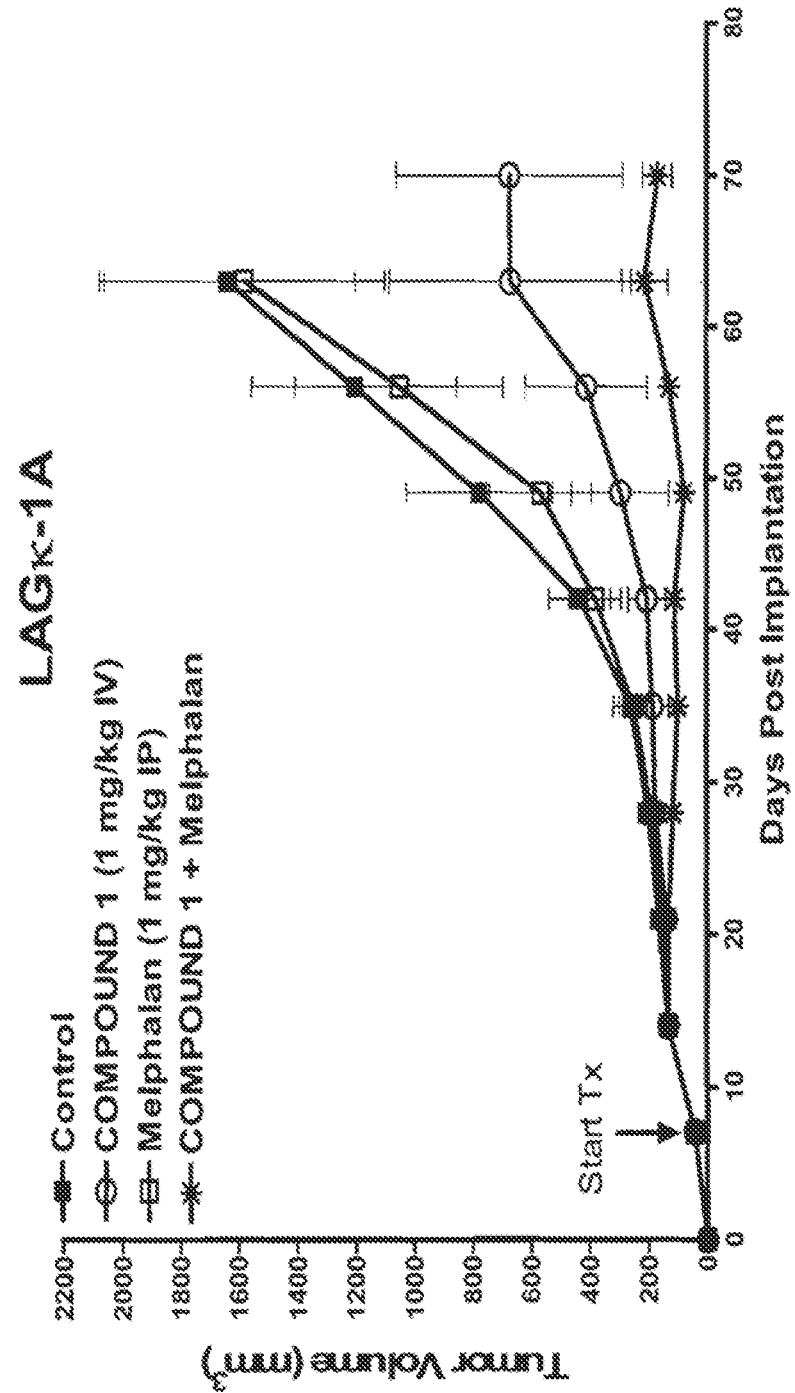

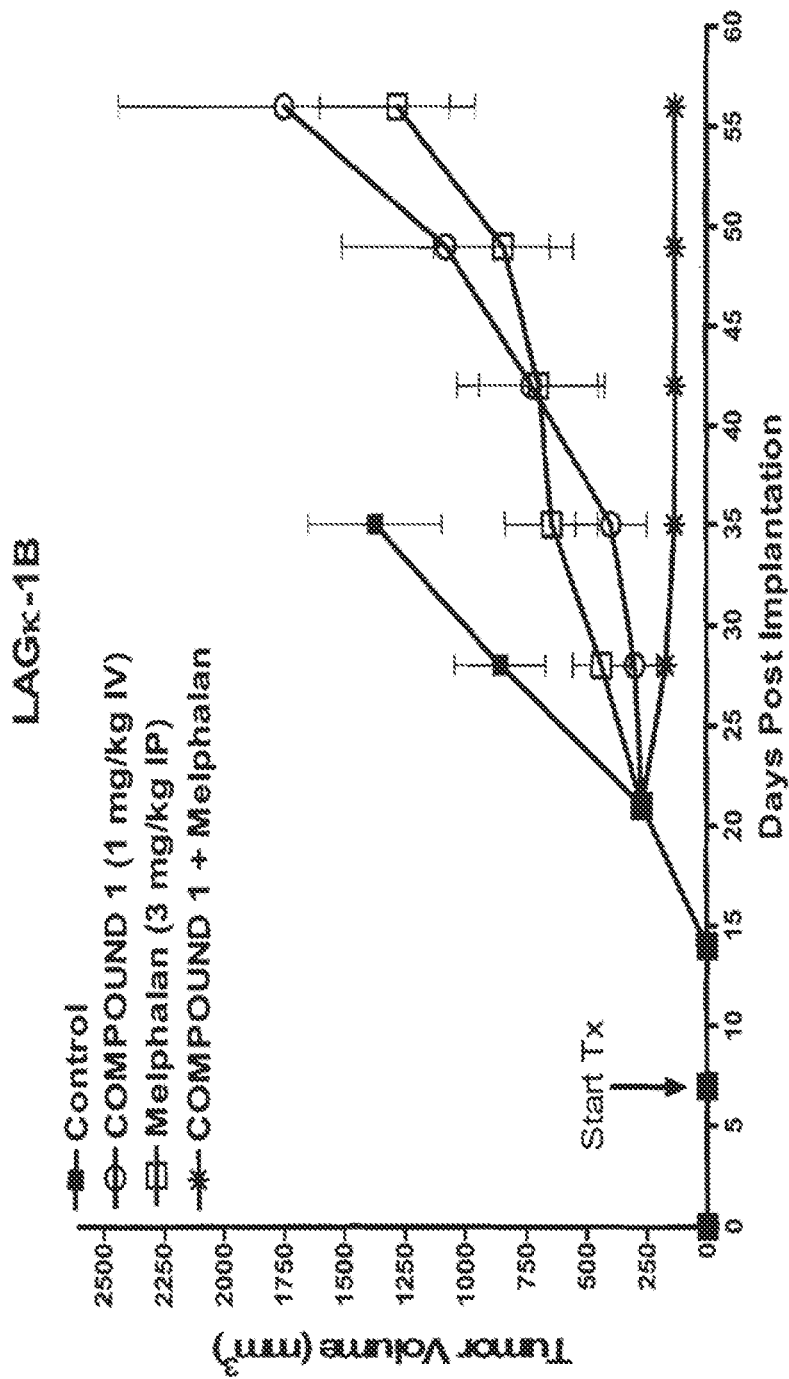

Control

Isotype control

COMPOUND 1

Isotype control

Bortezomib 0.5 mg/kg

Isotype control

COMPOUND 1 + Bortezomib

Isotype control

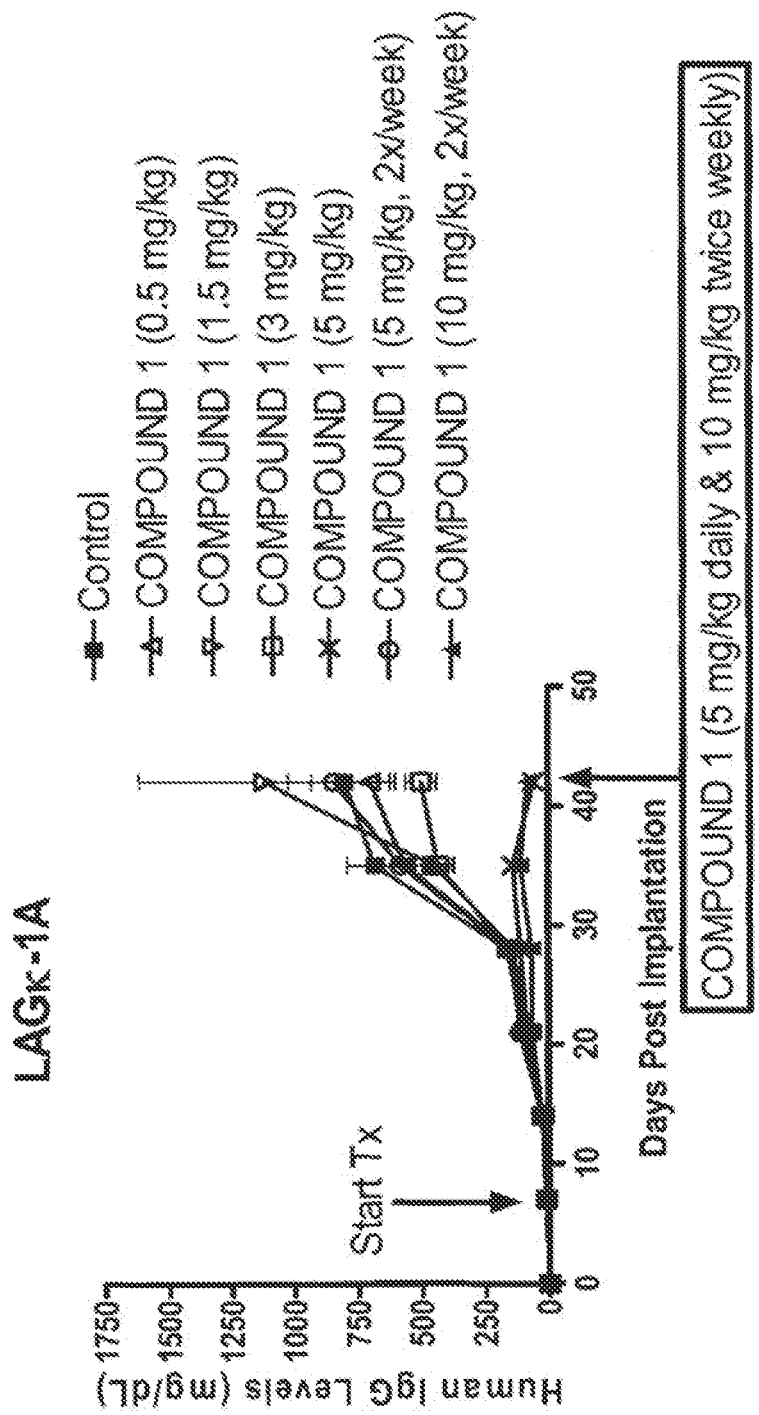

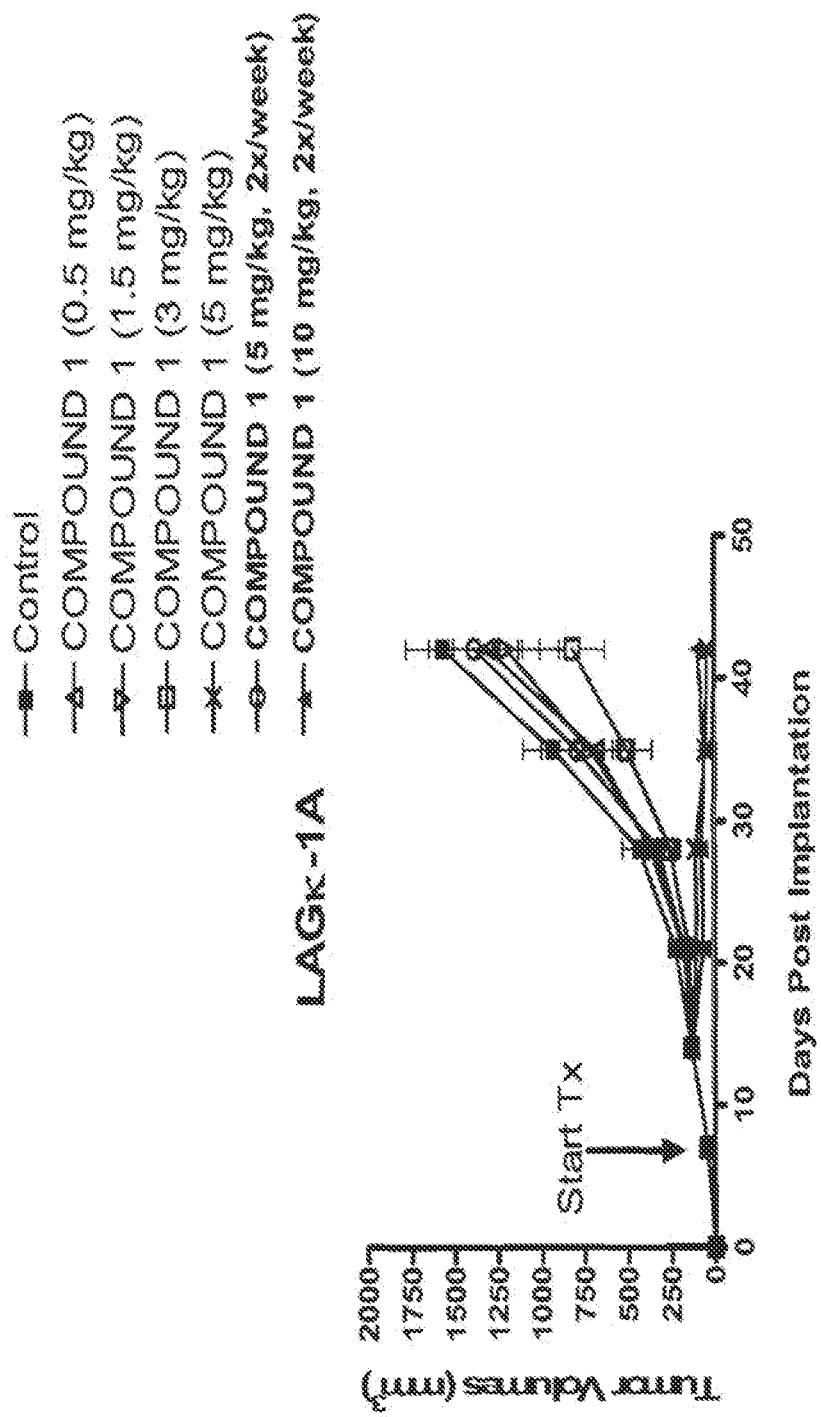

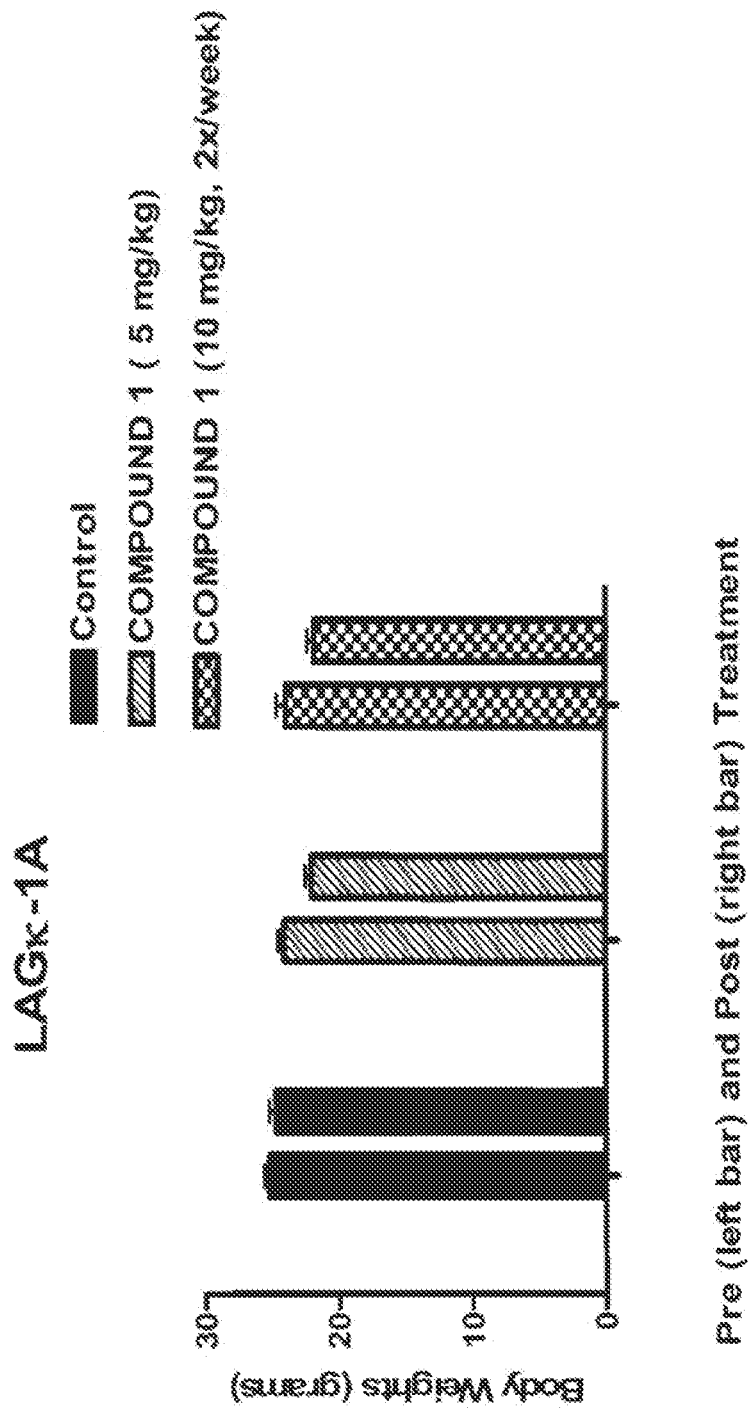

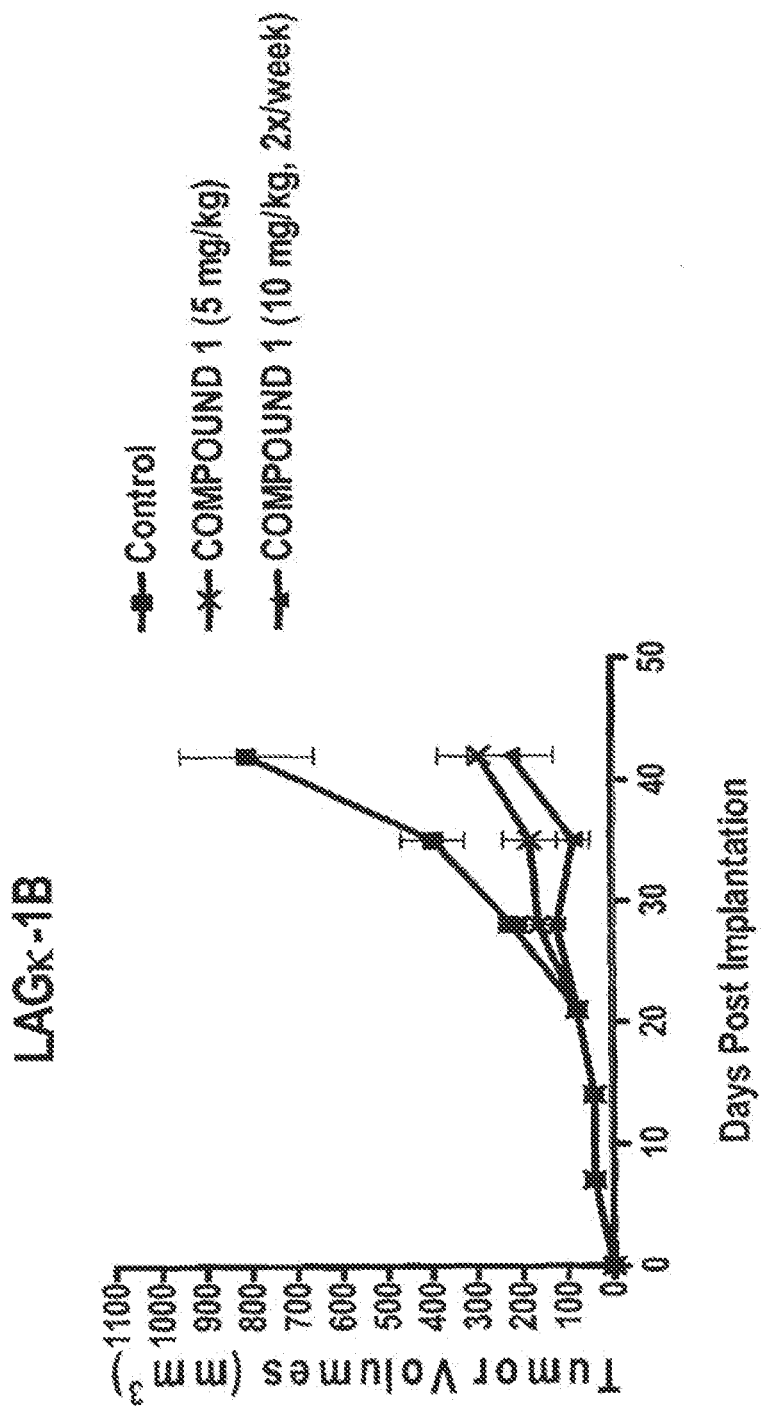

COMBINATION THERAPY FOR THE TREATMENT OF MULTIPLE MYELOMA

CROSS REFERENCE TO RELATED APPLICATIONS

This application is a continuation of International Application PCT/US2009/067174, filed Dec. 8, 2009, which claims the benefit of U.S. Provisional Application No. 61/181,550, filed May 27, 2009, U.S. Provisional Application No. 61/185,501, filed Jun. 9, 2009, International Application PCT/US2009/003467, filed Jun. 9, 2009, and U.S. Provisional Application No. 61/232,594, filed Aug. 10, 2009, the disclosures of which are incorporated herein by reference in their entireties.

TECHNICAL FIELD

Combination drug therapy for multiple myeloma.

BACKGROUND

Multiple myeloma (MM), a plasma cell neoplasm, comprises approximately 10% of all hematologic malignancies (1). The clinical success of the proteasome inhibitor (PI) bortezomib in MM has validated the ubiquitin-proteasome system (UPS) as a compelling target for drug development (2). The proteasome is a multi-subunit protein complex responsible for degrading misfolded and damaged proteins as well as intracellular signaling intermediates (3). Because of their dysregulated signaling pathways, neoplastic cells rely heavily on the UPS, and therefore are particularly sensitive to proteasome inhibition (4). Apoptosis of MM cells following proteasome inhibition occurs through multiple mechanisms, including down-regulation of prosurvival NF-κB signaling, inhibition of angiogenesis, activation of a misfolded protein stress response, induction of intrinsic and extrinsic cell death pathways, and inhibition of MM cell adhesion to the bone marrow stromal cells (5-8).

The first PI in clinical development, bortezomib (also known as PS-341 or [(1R)-3-methyl-1-({(2S)-3-phenyl-2-[(pyrazin-2-ylcarbonyl)amino]propanoyl}amino)butyl]boronic acid), was approved by the FDA in 2003 following two successful single-agent phase II trials in relapsed MM (9,10). Bortezomib also shows remarkable activity in combination with other agents. In preclinical studies, subtoxic concentrations of bortezomib overcame the resistance of MM cells to chemotherapeutic drugs, including melphalan, doxorubicin, or mitoxantrone (11-13). In addition, bortezomib potentiates the activity of novel therapies for MM, including lenalidomide, arsenic trioxide, and inhibitors of histone deacetylase or PKC, as well as second-generation PIs (14-18). Synergistic in vitro activity has translated to enhanced in vivo efficacy in clinical studies testing bortezomib-based combination therapies. In the phase III VISTA trial evaluating melphalan and prednisone (MP) with or without bortezomib (V), VMP was associated with a 3-year overall survival rate of 72%, compared with 59% for MP therapy (P=0.003) (19). Notably, the addition of bortezomib to a regimen can, in some cases, resensitize patients to failed therapies. For example, in a phase II study, 60% of MM patients who relapsed following melphalan treatment subsequently responded to bortezomib/melphalan combination therapy (20). Similarly, bortezomib combined with thalidomide and dexamethasone yielded a 63% overall response rate in a relapsed population of MM patients, 73% of whom had previous exposure to thalidomide (21).

Although the approval of bortezomib has transformed treatment of MM, a sizeable proportion of patients fail to respond to bortezomib therapy. The results of a recent study suggest that differing proteasome expression and activity levels may underlie the variable sensitivity of MM tumors to treatments with PIs (22). Furthermore, even patients who initially respond to bortezomib face almost-certain relapse. Growing evidence suggests that a small population of drug-resistant cancer stem cells may be responsible for recurrence of MM following remission (23-26). These cells express surface antigens characteristic of normal memory B cells, lack the plasma cell marker CD138, and do not secrete antibody (24). Furthermore, when challenged with commonly used anti-myeloma drugs (e.g., dexamethasone, lenalidomide, cyclophosphamide) the CD138-negative stem cell population shows greater drug resistance than the rest of the malignant cell population (24). Single-agent bortezomib, for example, is active against MM cells that produce high amounts of immunoglobulin (27), but has little effect on growth of CD138-negative MM cells (24). These data highlight the need for new MM therapies that target cancer stem cells, as well as the remainder of the malignant plasma cell subtypes within the tumor population A search for novel, more potent, or better-tolerated PIs resulted in the synthesis of COMPOUND 1 (also known as [(1R)-1-[[(2S,3R)-3-hydroxy-2-[6-phenyl-pyridine-2-carbonyl)amino]-1-oxobutyl]amino]-3-methylbutylboronic acid; Bernardini, et al., U.S. Application No. US 2005/0107307). Like bortezomib, COMPOUND 1 is a reversible PI in the peptide boronic acid class (28). In contrast to bortezomib, which is administered by intravenous (IV) bolus, COMPOUND 1 is active as an oral formulation in preclinical studies (28,29). Furthermore, COMPOUND 1 shows similar or better single-agent antitumor activity when compared with bortezomib, both in primary MM plasma cells in vitro and in RPMI8226 mM xenografts in vivo (29). COMPOUND 1 has the following chemical structure:

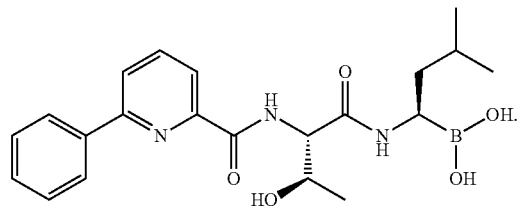 [SMILES: CC(C)C[C@H](NC(=O)[C@@H](NC(=O)c1cccc(-c2ccccc2)n1)[C@@H](C)O)B(O)O]

There remains a need for treatment options that can offer the best long-term outcome for multiple-myeloma patients. The need is especially urgent for novel therapies for patients with relapsed or refractory disease. Until the study disclosed herein, the combination therapy of COMPOUND 1 with either bortezomib or melphalan had never been investigated. These combination therapies offer attractive treatment options for MM patients, including those with relapsed or refractory disease.

All references cited are hereby incorporated by reference.

SUMMARY

Provided are methods for treating multiple myeloma in a subject with COMPOUND 1. In one embodiment, the subject is administered a combination of COMPOUND 1 and bortezomib. Preferably, the bortezomib is administered as a prodrug. Preferably, the bortezomib is administered intravenously or orally.

Preferably, the bortezomib is administered at a dose in the range of about 0.5 mg/m² to about 2 mg/m². Preferably, the bortezomib is administered at a dose in the range of about 0.7 mg/m² to about 1.3 mg/m².

Preferably, the bortezomib is administered pursuant to a scheduled dosing cycle in which bortezomib is administered every 3 to 7 days for 2 to 4 weeks, followed by a rest period of about 7 to 21 days during which bortezomib is not administered. Preferably, the bortezomib is administered pursuant to a scheduled dosing cycle in which bortezomib is administered on days 1, 4, 8 and 11 of a 21 day cycle. Preferably, the bortezomib is administered pursuant to a scheduled dosing cycle in which bortezomib is administered on days 1, 4, 8 and 11 of a 28 day cycle. Preferably, the scheduled cycle is repeated at least once.

In another embodiment, the subject is administered a combination of COMPOUND 1 and melphalan. Preferably, the melphalan is administered as a prodrug. Preferably, the melphalan is administered orally or intravenously.

Preferably, the melphalan is administered at a dose in the range of about 0.025 mg/kg to about 0.5 mg/kg. Preferably, the melphalan is administered at a dose in the range of about 0.025 mg/kg to about 0.3 mg/kg.

Preferably, the melphalan is administered pursuant to a scheduled dosing cycle in which melphalan is administered every 3 to 7 days for 1 to 2 weeks, followed by a rest period of about 4-6 weeks during which melphalan is not administered. Preferably, the melphalan is administered pursuant to a scheduled dosing cycle in which melphalan is administered once-daily for about 4 to about 7 days, followed by a rest period of about 4-6 weeks. Preferably, the melphalan is administered pursuant to a scheduled dosing cycle in which melphalan is administered once-daily for about 4 to about 5 days, followed by a rest period of about 4-6 weeks. Preferably, the scheduled cycle is repeated at least once.

Preferably, the COMPOUND 1 is administered as a prodrug. Preferably, the COMPOUND 1 prodrug is a pharmaceutically acceptable ester form of COMPOUND 1. Preferably, the COMPOUND 1 is administered intravenously or orally.

Preferably, the COMPOUND 1 is administered at a dose in the range of about 0.5 mg/m² to about 5 mg/m². Preferably, the COMPOUND 1 is administered at a dose in the range of about 1 mg/m² to about 3 mg/m². Preferably, the COMPOUND 1 is administered pursuant to a scheduled dosing cycle in which COMPOUND 1 is administered every 3 to 14 days for 2 to 4 weeks, followed by a rest period of about 7 to 21 days during which COMPOUND 1 is not administered.

Preferably, the COMPOUND 1 is administered pursuant to a scheduled dosing cycle in which COMPOUND 1 is administered on days 1, 4, 8 and 11 of a 21 day cycle. Preferably, the COMPOUND 1 is administered pursuant to a scheduled dosing cycle in which COMPOUND 1 is administered on days 1, 4, 8 and 11 of a 28 day cycle. Preferably, the COMPOUND 1 is administered pursuant to a scheduled dosing cycle in which COMPOUND 1 is administered on days 1, 8 and 15 of a 28 day cycle. Preferably, the COMPOUND 1 is administered pursuant to a scheduled dosing cycle in which COMPOUND 1 is administered on days 1 and 15 of a 21 day cycle. Preferably, the COMPOUND 1 is administered pursuant to a scheduled dosing cycle in which COMPOUND 1 is administered on days 1 and 15 of a 28 day cycle. Preferably, the scheduled cycle is repeated at least once.

Preferably, the COMPOUND 1 is administered on days 1, 5 and 9 of a 21 day cycle or a 28 day cycle, and bortezomib is administered on days 3, 8, and 12 of the 21 day cycle or the 28 day cycle. Preferably, the bortezomib is administered on days 1, 5 and 9 of a 21 day cycle or a 28 day cycle, and COMPOUND is administered on days 3, 8, and 12 of the 21 day cycle or the 28 day cycle.

BRIEF DESCRIPTION OF THE DRAWINGS

FIG. 2. COMPOUND 1, alone or in combination with bortezomib, does not inhibit the viability of normal peripheral blood mononuclear cells (PBMCs). A, PBMCs from a healthy volunteer were incubated with vehicle control (black bar), COMPOUND 1 alone (3.0 nM) (white bars), bortezomib alone (indicated concentrations) (striped bars), or COMPOUND 1 (3.0 nM)+bortezomib (indicated concentrations) (hatched bars) for 48 hours, after which cell viability was determined with the MTS assay. B, PBMCs from the same volunteer as in A were incubated with vehicle control (black bar), bortezomib alone (3.0 nM) (white bars), COMPOUND 1 alone (indicated concentrations) (striped bars), or COMPOUND 1 (indicated concentrations)+bortezomib (3.0 nM) (hatched bars), after which cell viability was determined using the MTS assay. C, PBMCs from a second volunteer were incubated with vehicle control (black bar), COMPOUND 1 alone (3.0 nM) (white bars), bortezomib alone (indicated concentrations) (striped bars), or COMPOUND 1 (3.0 nM)+bortezomib (indicated concentrations) (hatched bars) for 48 hours, after which cell viability was determined with the MTS assay. D, PBMCs from 3 healthy volunteers were incubated with increasing concentrations of COMPOUND 1 for 48 hours, after which cell viability was determined with the MTS assay. Each graph (A-D) is representative of three independent experiments.

FIG. 4. COMPOUND 1 inhibits the growth of human MM tumors. Following 28 days of drug treatment with IV COMPOUND 1, serum hIgG levels (A) were essentially undetectable (P=0.0001 for 1 mg/kg and P=0.0002 for 3 mg/kg) compared with control. Similarly, COMPOUND 1 administered IV at 1 or 3 mg/kg resulted in reductions in tumor volumes (B) compared with mice treated with diluent alone at the same time point (P=0.0001 for each dose compared with control). Starting on day 21, mice bearing human LAGκ-1B tumors were treated twice weekly for the duration of the study with vehicle control or the indicated concentrations of COMPOUND 1, and tumor volume was assessed weekly. Compared with control-treated mice, mice treated with COMPOUND 1 twice weekly at 3 mg/kg IV or 10 mg/kg oral COMPOUND 1 showed significantly smaller tumors (C) following 14 days of treatment (P=0.0008 and P=0.0028, respectively). Data are presented as means±standard error of the mean, with 7-8 mice per group.

FIG. 7. Oral COMPOUND 1 inhibits the growth of human MM tumors. Significant inhibition of paraprotein levels and tumor volume (A and B, respectively) following three weeks and four weeks of treatment with COMPOUND 1 at 10 mg/kg twice weekly (hIgG: P=0.0011; tumor volume: P=0.001) and daily at 5 mg/kg (hIgG: P<0.0001; tumor volume: P<0.0001), respectively. Body weight changes during five weeks of treatment (C). Similarly, at day 35, 5 mg/kg administered daily or 10 mg/kg twice weekly resulted in significant tumor volume inhibition (P=0.0327; P=0.0018, respectively) in the LAGκ-1B model (D).

DETAILED DESCRIPTION OF ILLUSTRATIVE EMBODIMENTS

Figure 1A:
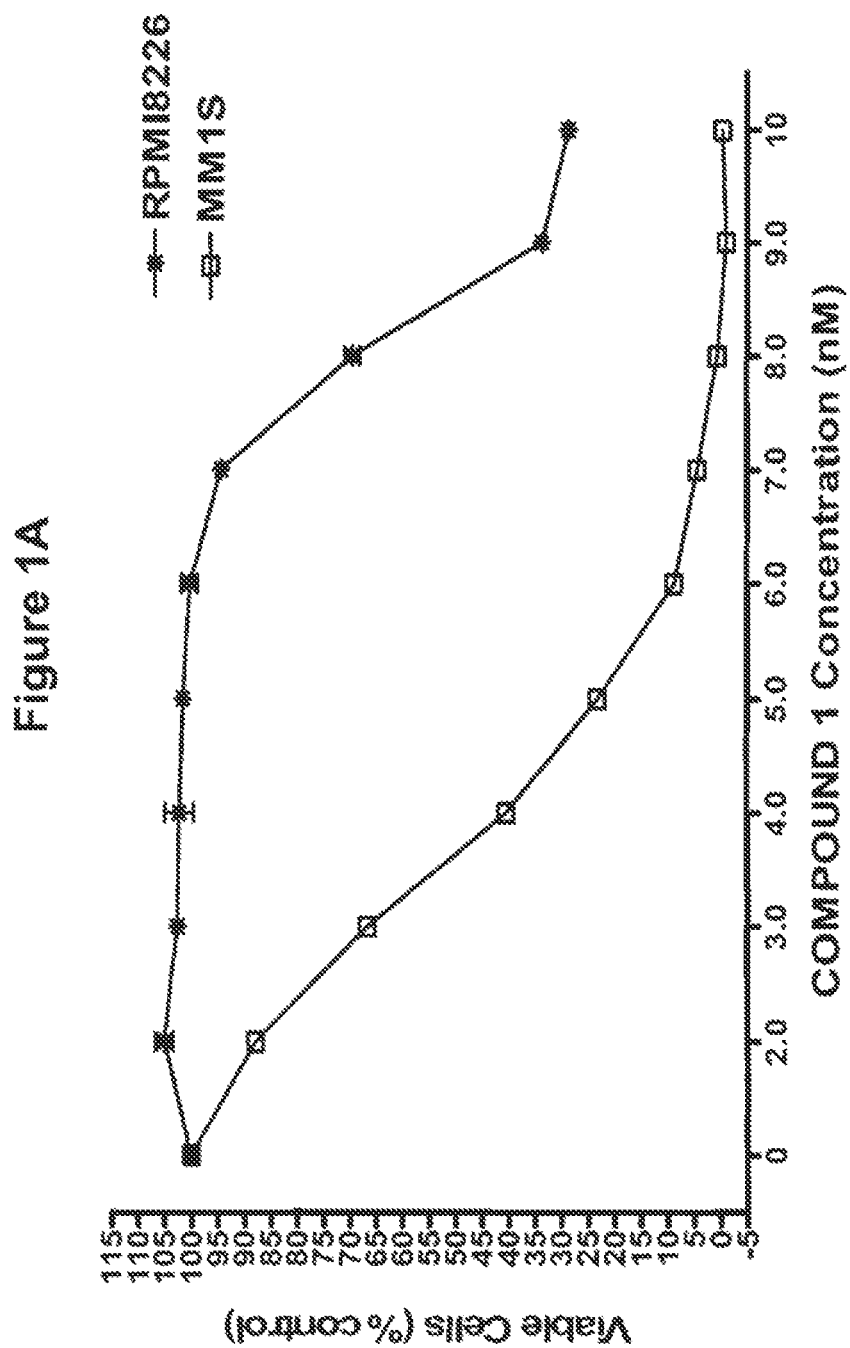
FIG. 1. COMPOUND 1 inhibits the viability of MM cell lines as a single agent or in combination with other anti-MM therapeutics. A, The viability of MM1S (triangles) and RPMI8226 (squares) was assessed by MTS assay following 48 hours of incubation with the indicated concentrations of COMPOUND 1. B, MM1S cells were exposed to vehicle control (black bar), COMPOUND 1 (white bars), bortezomib (striped bars), or both agents (hatched bars) at the concentrations indicated for 48 hours, and viability was quantified by MTS assay. C, RPMI8226 cells were exposed to vehicle control (black bar), melphalan (40 nM) (white bars), COMPOUND 1 (concentrations indicated) (striped bars), or both agents (hatched bars) for 48 hours, and viability was quantified by MTS assay. Data graphed are the mean±standard error of the mean (SEM) using 6 replicates. In B and C, combination indices (CI) are displayed above the hatched bars. CI values below 0.9 indicate synergistic activity; CI values between 0.9 and 1.1 indicate additive activity, and CI values above 1.1 indicate antagonistic activity.

The term "about" as used herein when referring to a measurable value such as an amount, a temporal duration, and the like, is meant to encompass variations of ±10% from the specified value. For example, the phrase "about 50%" includes±10% of 50, or from 45% to 55%.

As used herein, the term "subject" includes warm blooded animals, preferably mammals, including humans. In a preferred embodiment, the subject is a primate. In an even more preferred embodiment, the subject is a human.

Provided are methods for treating multiple myeloma in a subject. In one embodiment, the subject is administered a combination of COMPOUND 1 and bortezomib. Bortezomib ([(1R)-3-methyl-1-({(2S)-3-phenyl-2-[(pyrazin-2-ylcarbonyl)amino]propanoyl}amino)butyl]boronic acid; marketed by Millennium Pharmaceuticals under the trade name Velcade®) has the following chemical structure:

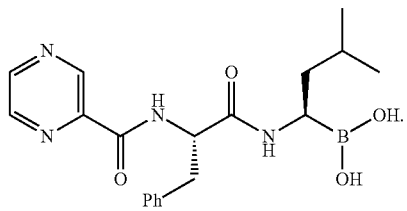 [SMILES: CC(C)C[C@H](NC(=O)[C@H](Cc1ccccc1)NC(=O)c1cnccn1)B(O)O]

We have found that the method of treating multiple myeloma with a combination of COMPOUND 1 and bortezomib according to the present invention synergistically treats multiple myeloma. This is surprising because COMPOUND 1 and bortezomib are both reversible boronic acid proteasome inhibitors that induce cell death through activation of the extrinsic and intrinsic apoptotic signaling pathways (7,29). Furthermore, both agents primarily target the proteasome's chymotrypsin-like catalytic activity, with minor inhibition of the caspase-like and little inhibition of the trypsin-like activities (29,34). Thus, COMPOUND 1 and bortezomib appear to have similar mechanisms of action. In addition, the compounds have very similar chemical structures. Thus, the means through which COMPOUND 1 and bortezomib together induce enhanced activity against MM cells in vitro and tumors, particularly nonsecretory tumors, in vivo is unclear.

In another embodiment, the subject is administered a combination of COMPOUND 1 and melphalan. We have found that the method of treating multiple myeloma with a combination of COMPOUND 1 and melphalan according to the present invention synergistically treats multiple myeloma.

Melphalan (4-[bis(2-chloroethyl)amino]-L-phenylalanine; marketed by GlaxoSmithKline under the trade name Alkeran®) has the following chemical structure:

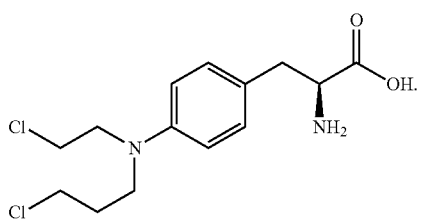 [SMILES: N[C@@H](Cc1ccc(N(CCCl)CCCCl)cc1)C(=O)O]

The COMPOUND 1, bortezomib and/or melphalan used in the present invention may be administered in any suitable chemical form, including as prodrugs, such as a pharmaceutically acceptable salt form and/or pharmaceutically acceptable ester form of the parent compound. Preferably, the pharmaceutically acceptable salt or ester derivative of the parent compound converts to the parent compound upon administration. As used herein, "pharmaceutically acceptable salt" refers to a derivative of the parent compound in which the compound is modified by making an acid or base salt thereof. Examples of pharmaceutically acceptable salts include, but are not limited to, mineral or organic acid salts of basic residues such as amines; alkali or organic salts of acidic residues such as carboxylic acids or boronic acids; and the like. As used herein, "pharmaceutically acceptable ester" refers to a derivative of the parent compound in which an acid residue is modified by making an ester thereof. Examples of pharmaceutically acceptable esters include, for example, boronic esters, i.e., an ester derivative of a boronic acid compound, and cyclic boronic esters. Examples of cyclic boronic esters include, but are not limited to, pinanediol boronic ester, pinacol boronic ester, 1,2-ethanediol boronic ester, 1,3-propanediol boronic ester, 1,2-propanediol boronic ester, 2,3-butanediol boronic ester, 1,1,2,2-tetramethylethanediol boronic ester, 1,2-diisopropylethanediol boronic ester, 5,6-decanediol boronic ester, 1,2-dicyclohexylethanediol boronic ester, bicyclohexyl-1,1'-diol, and 1,2-diphenyl-1,2-ethanediol boronic ester.

Therefore, in certain embodiments the COMPOUND 1 and/or bortezomib is administered as a boronic ester derivative of the parent compound. In one embodiment, the COMPOUND 1 is administered as a boronic ester derivative of COMPOUND 1. In one embodiment, the bortezomib is administered as a boronic ester derivative of bortezomib.

Any suitable method of administration may be used. Examples include injection (subcutaneous, intravenous, parenterally, intraperitoneally, intrathecal, etc.), oral, inhalation, and transdermal. When administered by injection, the injection can be bolus or continuous infusion. The COMPOUND 1 and bortezomib can be administered to the subject separately (e.g., as sequential injections, an injection and an oral administration, or separate oral administrations) or together as a mixture (e.g., in a single injection or a single oral administration, such as by administration of a single tablet containing both COMPOUND 1 and bortezomib). In the same way, the COMPOUND 1 and melphalan can be administered to the subject separately or together as a mixture. The proportion or concentration of a compound of the invention in a pharmaceutical composition can vary depending upon a number of factors including dosage, chemical characteristics (e.g., hydrophobicity), and the route of administration.

For example, bortezomib is suitable for oral administration or intravenous injection. For example, bortezomib is available under the trade name Velcade® from Millennium Pharmaceuticals as a sterile lyophilized powder in a single use vial, which contains 3.5 mg bortezomib and 35 mg of the bulking agent mannitol. The powder is reconstituted with 3.5 mL of 0.9% NaCl by the clinician for injection. The bortezomib is present as a mannitol boronic ester in the Velcade lyophilized formulation, and after reconstitution is present as the mannitol boronic ester in equilibrium with the parent boronic acid (42). Therefore, in one embodiment the bortezomib is administered by intravenous (IV) injection. In another embodiment, the bortezomib is administered orally, preferably in a tablet or capsule. In one embodiment, the bortezomib is administered by injection in the form of a prodrug, such as a boronic ester. In one embodiment, the bortezomib is administered orally in the form of a prodrug, such as a boronic ester.

For example, melphalan is suitable for oral administration or intravenous injection. For example, melphalan is available under the trade name Alkeran® from GlaxoSmithKline as either a film coated tablet for oral administration or a sterile lyophilized powder in a single use vial. The film coated tablet contains 2 mg melphalan, and the excipients colloidal silicon dioxide, crospovidone, hypromellose, macrogol/PEG 400, magnesium stearate, microcrystalline cellulose, and titanium dioxide. The lyophilized powder contains melphalan hydrochloride equivalent to 50 mg melphalan, and 20 mg povidone. The powder is reconstituted for injection using the vial of sterile diluent provided, which contains sodium citrate 0.2 g, propylene glycol 6.0 mL, ethanol (96%) 0.52 mL, and Water for Injection to a total of 10 mL (43). Therefore, in one embodiment the melphalan is administered by intravenous (IV) injection as the hydrochloride salt. In another embodiment, the melphalan is administered orally, preferably in a tablet or capsule.

For example, COMPOUND 1 is suitable for administration by IV injection or by oral dosage form, such as in a tablet or capsule (28, 29). For example, COMPOUND 1 is presently under evaluation in a first in man Phase I clinical study in patients with solid tumor or Non-Hodgkin's lymphoma. In the Phase I study, COMPOUND 1 is provided as a sterile lyophilized powder in a single use vial, which contains 4 mg COMPOUND 1, 196 mg of the bulking agent hydroxypropyl-β-cyclodextrin, and 156.8 mg of the bulking agent mannitol. The powder is reconstituted with either 5 mL or 10 mL (depending upon the intended dose) of either sterile Water for Injection, 0.9% NaCl, or 5% mannitol before injection. Therefore, in one embodiment the COMPOUND 1 is administered by intravenous (IV) injection. In another embodiment, the COMPOUND 1 is administered orally, preferably in a tablet or capsule. In one embodiment, the COMPOUND 1 is administered by injection in the form of a prodrug, such as a boronic ester. In one embodiment, the COMPOUND 1 is administered orally in the form of a prodrug, such as a boronic ester.

The combination of COMPOUND 1 and bortezomib or COMPOUND 1 and melphalan is preferably administered in an amount effective to treat multiple myeloma, e.g., effective to prevent, alleviate, or ameliorate symptoms of the disease, prolong survival of the subject being treated, prevent undesirable cell growth, or reduce the size of a pre-existing benign cell mass or malignant tumor in the subject. Determination of the effective amount of each agent in the combination is well within the capability of those skilled in the art in light of the detailed disclosure and examples provided herein. The effective amount can vary depending on such factors as the type of cell growth being treated or inhibited, the size of the subject, the severity of the cancer cell growth or tumor, the frequency of administration (e.g., daily vs. once every several days), the manner of administration of the compound, the health and co-morbid conditions of the patient, the judgment and experience of the prescribing physician (e.g., with the same or similar drugs), the mode of administration, the bioavailability characteristics of the dosage form administered, the dose regimen selected, and the kind of concurrent treatment (e.g., additional chemotherapeutic agents). U.S. Pat. No. 5,427, 916, for example, describes method for predicting the effectiveness of antineoplastic therapy in individual patients, and illustrates certain methods which can be used in conjunction with the treatment protocols of the instant invention. For example, effective doses can be extrapolated from dose-response curves derived from in vitro or animal model test systems, and may be based on the surface area of the patient.

Treatment can be initiated with smaller dosages which are less than the optimum dose of the compound. Thereafter, the dosage can be increased by small increments until the optimum effect under the circumstances is reached. The total administration of the COMPOUND 1 and bortezomib or COMPOUND 1 and melphalan can be readily varied by the treating physician to optimize efficacy and minimize side effects in light of the above considerations and the present detailed disclosure.

There is wide flexibility in the dosing schedules for COMPOUND 1, bortezomib, and melphalan according to present invention. In certain embodiments, the dosing schedules can be adapted from dosing schedules known to be suitable for these drugs. For example, bortezomib (1.3 mg/m$^2$) is approved to treat previously untreated multiple myeloma by administration as a 3-5 second bolus IV injection in combination with oral melphalan (9 mg/m$^2$) and oral prednisone (60 mg/m$^2$) for nine 6-week treatment cycles as shown in Table 1. In Cycles 1-4, bortezomib is administered twice weekly on days 1, 4, 8, 11, 22, 25, 29 and 32. In Cycles 5-9, bortezomib is administered once weekly on days 1, 8, 22 and 29 (42).

TABLE 1

Dosage Regimen for Patients with Previously Untreated Multiple Myeloma

| | | | Week | | | | | | | |
|---|---|---|---|---|---|---|---|---|---|---|
| | | 1 | | 2 | 3 | | 4 | | 5 | 6 |
| Twice Weekly Bortezomib (Cycles 1-4) | | | | | | | | | | |
| Bortezomib (1.3 mg/m$^2$) | Day 1 | — | — | Day 4 | Day 8 | Day 11 | rest period | Day 22 | Day 25 | Day 29 | Day 32 | rest period |
| Melphalan (9 mg/m$^2$) Prednisone (60 mg/m$^2$) | Day 1 | Day 2 | Day 3 | Day 4 | — | — | rest period | — | — | — | — | rest period |
| Once Weekly Bortezomib (Cycles 5-9 when used in combination with Melphalan and Prednisone) | | | | | | | | | | |
| Bortezomib (1.3 mg/m$^2$) | Day 1 | — | — | Day 8 | | Rest period | Day 22 | | Day 29 | | rest period |
| Melphalan (9 mg/m$^2$) Prednisone (60 mg/m$^2$) | Day 1 | Day 2 | Day 3 | Day 4 | — | — | Rest period | — | — | — | — | rest period | daily dosage may be divided and administered in portions during the day if desired. To optimize the dosing regimen, the effectiveness of a combination of COMPOUND 1 with bortezomib or COMPOUND 1 with melphalan to treat multiple myeloma can be monitored by comparing tumor measurements at two or more time points obtained from a patient undergoing anti-cancer treatment. In general, it is preferable to obtain the initial assessment of tumor burden from the patient prior to beginning therapy and one or more additional assessments at different time points during treatment. In such a use, a baseline determination of tumor burden prior to therapy is determined and then changes in the amount of cancer are determined during the course of therapy. Alternatively, two or more successive determinations can be made during treatment without the need of a pre-treatment baseline measurement of tumor burden. In such a use, the first assessment of tumor burden should be made from the subject as a baseline level for determining whether the tumor burden is increasing or decreasing.

The regimen of administration, e.g., the timing and/or sequence of administration, of the COMPOUND 1 and bortezomib or COMPOUND 1 and melphalan can vary depending on such factors as the pharmacokinetics of each dosage form, the type of cell growth being treated or inhibited, the size of the subject, the severity of the cancer cell growth or tumor, and the effective dosage. The timing and sequence of If significant drug-related toxicity is observed during the treatment regimen (e.g., hematological toxicity), subsequent bortezomib doses can be skipped and/or reduced (e.g., from 1.3 mg/m$^2$ to 1 mg/m$^2$, and possibly to 0.7 mg/m$^2$). Additionally or alternatively, melphalan doses can be reduced by 25% in the next cycle (42).

As another example, bortezomib is approved to treat relapsed or refractory multiple myeloma by administration as a 3-5 second bolus IV injection on days 1, 4, 8, and 11 of a 3-week cycle followed by a 10-day rest period (days 12-21). For extended therapy of more than 8 cycles, bortezomib can be administered on the standard schedule or on a maintenance schedule of once weekly for 4 weeks (days 1, 8, 15 and 22) followed by a 13-day rest period (days 23-35) (42).

If significant drug-related toxicity is observed during the treatment regimen (e.g., hematological toxicity, neuropathic pain and/or peripheral neuropathy), subsequent bortezomib doses can be skipped and/or reduced (e.g., from 1.3 mg/m$^2$ to 1 mg/m$^2$, and possibly to 0.7 mg/m$^2$) (42).

For use in the combination of the present invention, the bortezomib regimen may be similar to or different from the approved multiple myeloma regimens, including those presented above. For example, the bortezomib may be administered more or less frequently than in the approved regimens, and may optionally be administered at higher or lower doses.

The bortezomib may be administered in conjunction with COMPOUND 1 at any suitable dose. Suitable bortezomib doses can be in the range of about 0.5 mg/m² to about 7 mg/m², such as about 0.5 mg/m² to about 5 mg/m², for example about 0.5 mg/m² to about 3 mg/m². A suitable bortezomib dose will typically range from about 0.5 mg/m² to about 2 mg/m². Preferably, the bortezomib dose is in the range of about 0.6 mg/m² to about 1.5 mg/m². More preferably, the bortezomib dose is in the range of about 0.7 mg/m² to about 1.3 mg/m². Preferred bortezomib doses include, but are not limited to, 0.7 mg/m², 1 mg/m², or 1.3 mg/m². The preceding doses are suitable for any method of bortezomib administration, and are especially suitable for subcutaneous or intravenous dosing, with intravenous dosing preferred. Oral doses of bortezomib will typically be at the high end of the preceding ranges, such as about 1 mg/m² to about 5 mg/m², about 1.5 mg/m² to about 4 mg/m², or about 2 mg/m² to about 3 mg/m².

The bortezomib may be administered at the above-described doses with COMPOUND 1 according to any suitable schedule. The bortezomib dose amounts may be constant or varied within the dosing schedule. Preferably, the bortezomib dose is maintained at a constant level during the schedule unless significant drug-related toxicity is observed, in which case subsequent doses can be reduced, for example by about 20-30%. The bortezomib may be administered on the same or different days as the COMPOUND 1. In one embodiment, the bortezomib and COMPOUND 1 are administered on the same days during the schedule. A suitable bortezomib schedule will typically range from once-daily dosing to once-weekly dosing or even once-monthly dosing. Preferably, the bortezomib is administered less frequently than once-daily, such as one dose every 2-14 days. Preferably, the bortezomib is administered every 3 to 7 days, such as every 3 to 4 days. Preferably, the schedule includes, after treatment with bortezomib for one or more weeks, such as 2, 3, or 4 weeks, a period of at least 5 days during which bortezomib is not administered, such as a period of about 7 to 21 days. Preferably, the rest period is about 10 to 17 days, such as about 10 days or about 17 days. For example, the bortezomib can be administered on days 1, 4, 8 and 11 of a 21 day cycle, wherein days 12-21 are a rest period. As another example, the bortezomib can be administered on days 1, 4, 8, and 11 of a 28 day cycle, wherein days 12-28 are a rest period. As another example, the bortezomib can be administered once weekly for 4 weeks (e.g., days 1, 8, 15 and 22 of a 35 day cycle) followed by a 13-day rest period (e.g., days 23 to 35 of the 35 day cycle). The scheduled dosing cycles can be repeated one or more times. For example, the scheduled cycle may be repeated until maximum response is observed, plus one or two additional cycles. As another example, the scheduled cycle may be repeated for 6 to 12 cycles. Optionally, after the initial cycles are completed, a "maintenance schedule" may be used in which the bortezomib is administered less frequency than in the initial schedule, such as once per week or once every two weeks. The maintenance schedule may be continued either for a fixed period of time, generally 1-2 years, or indefinitely as long as the patient is continuing to show no signs of progressive disease and is tolerating the treatment without significant toxicity.

The COMPOUND 1 may be administered in conjunction with bortezomib at any suitable dose. Suitable COMPOUND 1 doses can be in the range of about 0.5 mg/m² to about 10 mg/m², such as about 0.5 mg/m² to about 5 mg/m², or about 0.5 mg/m² to about 3 mg/mg². A suitable COMPOUND 1 dose will typically range from about 0.5 mg/m² to about 3 mg/m². Preferably, the COMPOUND 1 dose is in the range of about 1 mg/m² to about 3 mg/m². More preferably, the COMPOUND 1 dose is in the range of about 1.5 mg/m² to about 2.5 mg/m². Preferred COMPOUND 1 doses include, but are not limited to, 1.1 mg/m², 1.5 mg/m², 1.8 mg/m², 2.1 mg/m², or 2.4 mg/m². The preceding doses are suitable for any method of COMPOUND 1 administration, and are especially suitable for subcutaneous or intravenous dosing, with intravenous dosing preferred. Oral doses of COMPOUND 1 will typically be at the high end of the preceding ranges, such as about 1 mg/m² to about 7 mg/m². In one embodiment, the oral dose of COMPOUND 1 is about 2 mg/m² to about 6 mg/m², such as about 3 mg/m² to about 5 mg/m². Exemplary oral COMPOUND 1 doses include, but are not limited to, 2 mg/m², 3 mg/m², 4 mg/m², 5 mg/m² or 6 mg/m².

The COMPOUND 1 may be administered at the above-described doses with bortezomib according to any suitable schedule. The COMPOUND 1 dose amounts may be constant or varied within the dosing schedule. Preferably, the COMPOUND 1 dose is maintained at a constant level during the schedule unless significant drug-related toxicity is observed, in which case subsequent doses can be reduced, for example by about 20-30%. The COMPOUND 1 may be administered on the same or different days as the bortezomib. In one embodiment, the COMPOUND 1 and bortezomib are administered on the same days during the schedule. A suitable COMPOUND 1 schedule will typically range from once-daily dosing to once-weekly dosing or even once-monthly dosing. Preferably, the COMPOUND 1 is administered less frequently than once-daily, such as one dose every 2-14 days. Preferably, the COMPOUND 1 is administered every 3 to 28 days, such as every 7 to 21 days. For example, the COMPOUND 1 may be administered twice per week. In another example, COMPOUND 1 may be administered once per week. In another example, COMPOUND 1 may be administered once every two weeks. Preferably, the schedule includes, after treatment with COMPOUND 1 for one or more weeks, such as 2, 3, or 4 weeks, a period of at least 5 days during which COMPOUND 1 is not administered, such as a period of about 7 to 21 days. Preferably, the rest period is about 10 to 17 days, such as about 10 days or about 17 days. For example, the COMPOUND 1 can be administered on days 1, 4, 8 and 11 of a 21 day cycle, wherein days 12-21 are a rest period. In another embodiment, the COMPOUND 1 can be administered on days 1, 4, 8, and 11 of a 28 day cycle, wherein days 12-28 are a rest period. In another embodiment, the COMPOUND 1 can be administered on days 1, 8 and 15 of a 28 day cycle, wherein days 16-28 are a rest period. In another embodiment, the COMPOUND 1 can be administered on days 1 and 8 of a 21 day cycle, wherein days 12-21 are a rest period. In another embodiment, the COMPOUND 1 can be administered on days 1 and 8 of a 28 day cycle, wherein days 12-28 are a rest period. In another embodiment, the COMPOUND 1 can be administered on days 1 and 15 of a 21 day cycle. In another embodiment, the COMPOUND 1 can be administered on days 1 and 15 of a 28 day cycle. As previously mentioned, the bortezomib can be administered on the same or different days of the schedule. For example, both the COMPOUND 1 and bortezomib can be administered on days 1, 4, 8 and 11 of a 21 day cycle. In another embodiment, both the COMPOUND 1 and bortezomib can be administered on days 1, 4, 8, and 11 of a 28 day cycle. In another embodiment, the bortezomib can be administered on days 1, 4, 8 and 11 of a 21 day cycle, and COMPOUND 1 can be administered on days 1 and 8 of the 21 day cycle. In another embodiment, the bortezomib can be administered on days 1, 4, 8 and 11 of a 28 day cycle, and COMPOUND 1 can be administered on days 1 and 8 of the 28 day cycle. In another embodiment, the bortezomib can be administered on days 1, 4, 8 and 11 of a 28 day cycle, and COMPOUND 1 can be administered on days 1, 8 and 15 of the 28 day cycle. In another embodiment, the bortezomib can be administered on days 1, 4, 8, and 11 of a 21 day cycle, and COMPOUND 1 can be administered on days 1 and 15 of the 21 day cycle. In another embodiment, the bortezomib can be administered on days 1, 4, 8, and 11 of a 28 day cycle, and COMPOUND 1 can be administered on days 1 and 15 of the 28 day cycle. In another embodiment, the COMPOUND 1 can be administered on days 1, 4, 8 and 11 of a 21 day cycle or a 28 day cycle, and bortezomib can be administered on days 2, 5, 9 and 12 of the 21 day cycle or the 28 day cycle. In another embodiment, the bortezomib can be administered on days 1, 4, 8 and 11 of a 21 day cycle or a 28 day cycle, and COMPOUND 1 can be administered on days 2, 5, 9 and 12 of the 21 day cycle or the 28 day cycle. In another embodiment, the COMPOUND 1 can be administered on days 1 and 8 of a 21 day cycle or a 28 day cycle, and bortezomib can be administered on days 2, 5, 9 and 12 of the 21 day cycle or the 28 day cycle. In another embodiment, the COMPOUND 1 can be administered on days 1, 8 and 15 of a 28 day cycle, and bortezomib can be administered on days 2, 5, 9 and 12 of the 28 day cycle. In another embodiment, the bortezomib can be administered on days 1, 4, 8 and 11 of a 21 day cycle or a 28 day cycle, and COMPOUND 1 can be administered on days 2 and 9 of the 21 day cycle or the 28 day cycle. In another embodiment, the COMPOUND 1 can be administered on days 1 and 15 of a 21 day cycle or a 28 day cycle, and bortezomib can be administered on days 2, 5, 9, and 12 of the 21 day cycle or the 28 day cycle. In another embodiment, the bortezomib can be administered on days 1, 4, 8, and 11 of a 21 day cycle or a 28 day cycle, and COMPOUND 1 can be administered on days 2 and 16 of the 21 day cycle or the 28 day cycle. In another embodiment, the COMPOUND 1 can be administered on days 1 and 8 of a 21 day cycle or a 28 day cycle, and bortezomib can be administered on days 4 and 11 of the 21 day cycle or the 28 day cycle. In another embodiment, the COMPOUND 1 can be administered on days 1, 8 and 15 of a 28 day cycle, and bortezomib can be administered on days 4 and 11 of the 28 day cycle. In another embodiment, the bortezomib can be administered on days 1 and 8 of a 21 day cycle or a 28 day cycle, and COMPOUND 1 can be administered on days 4 and 11 of the 21 day cycle or the 28 day cycle. In another embodiment, the bortezomib can be administered on days 1 and 8 of a 21 day cycle or a 28 day cycle, and COMPOUND 1 can be administered on days 1 and 8 of the 21 day cycle or the 28 day cycle. In another embodiment, the COMPOUND 1 can be administered on days 1, 5 and 9 of a 21 day cycle or a 28 day cycle, and bortezomib can be administered on days 3, 8, and 12 of the 21 day cycle or the 28 day cycle. In another embodiment, the COMPOUND 1 can be administered on days 1, 8 and 15 of a 28 day cycle, and bortezomib can be administered on days 3, 8, and 12 of the 28 day cycle. In another embodiment, the bortezomib can be administered on days 1, 5 and 9 of a 21 day cycle or a 28 day cycle, and COMPOUND 1 can be administered on days 3, 8, and 12 of the 21 day cycle or the 28 day cycle. In another embodiment, the COMPOUND 1 can be administered on days 1 and 15 of a 21 day cycle or a 28 day cycle, and bortezomib can be administered on days 1, 6 and 11 of the 21 day cycle or the 28 day cycle. In another embodiment, the COMPOUND 1 can be administered on days 1, 8 and 15 of a 28 day cycle, and bortezomib can be administered on days 1, 6 and 11 of the 28 day cycle. In another embodiment, the bortezomib can be administered on days 1 and 11 of a 21 day cycle or a 28 day cycle, and COMPOUND 1 can be administered on days 5 and 15 of the 21 day cycle or the 28 day cycle. In another embodiment, the bortezomib can be administered on days 1 and 11 of a 28 day cycle, and COMPOUND 1 can be administered on days 1, 8 and 15 of the 28 day cycle. The scheduled dosing cycles can be repeated one or more times. For example, the scheduled cycle may be repeated until maximum response is observed, plus one or two additional cycles. As another example, the scheduled cycle may be repeated for 6 to 12 cycles. Optionally, after the initial cycles are completed, a "maintenance schedule" may be used in which the bortezomib and COMPOUND 1 are administered less frequency than in the initial schedule, such as once per week, once every two weeks, once every three weeks, or once every four weeks. The maintenance schedule may be continued either for a fixed period of time, generally 1-2 years, or indefinitely as long as the patient is continuing to show no signs of progressive disease and is tolerating the treatment without significant toxicity.

As previously mentioned, there is wide flexibility in the dosing schedules for COMPOUND 1 and melphalan according to present invention. In certain embodiments, the dosing schedules can be adapted from dosing schedules known to be suitable for these drugs. For example, oral melphalan (9 mg/m$^2$) is approved to treat previously untreated multiple myeloma in combination with bortezomib (1.3 mg/m$^2$) and oral prednisone (60 mg/m$^2$) for nine 6-week treatment cycles as shown in Table 1 above. Melphalan is administered on days 1, 2, 3, and 4 of each 6-week cycle (42).

Oral melphalan is usually administered as a single agent at a dose of 6 mg daily. The dose is adjusted, as required, on the basis of blood counts done at approximately weekly intervals. After 2-3 weeks of treatment, the drug is discontinued for up to 4 weeks, during which time the blood count should be followed carefully. When the white blood cell and platelet counts are rising, a maintenance dose of 2 mg daily may be instituted (43).

For use in the combination of the present invention, the melphalan regimen may be similar to or different from the approved multiple myeloma regimens, including those presented above. For example, the melphalan may be administered more or less frequently than in the approved regimens, and may optionally be administered at higher or lower doses.

The melphalan may be administered in conjunction with COMPOUND 1 at any suitable dose. Suitable melphalan doses can be in the range of about 0.025 mg/kg to about 0.5 mg/kg, such as about 0.05 mg/kg to about 0.3 mg/kg. A suitable melphalan dose will typically range from about 0.025 mg/kg to about 0.3 mg/kg. Preferably, the melphalan dose is in the range of about 0.05 mg/kg to about 0.25 mg/kg. More preferably, the melphalan dose is in the range of about 0.1 mg/kg to about 0.2 mg/kg. Preferred melphalan doses include, but are not limited to, 0.1 mg/kg, 0.15 mg/kg, 0.2 mg/kg, or 0.25 mg/kg. The preceding doses are suitable for any method of melphalan administration, and are especially suitable for subcutaneous, intravenous, or oral dosing, with oral dosing preferred.

The melphalan may be administered at the above-described doses with COMPOUND 1 according to any suitable schedule. The melphalan dose amounts may be constant or varied within the dosing schedule. Preferably, the melphalan dose is maintained at a constant level during the schedule unless significant drug-related toxicity is observed, in which case subsequent doses can be reduced, for example by about 20-30%. The melphalan may be administered on the same or different days as the COMPOUND 1. A suitable melphalan schedule will typically occur on consecutive days for a period of days, followed by a rest period. Preferably, the melphalan is administered once-daily for about 3 to about 7 days, followed by a rest period of about 1-6 weeks. Preferably, the melphalan is administered once-daily for about 4 to about 7 days, followed by a rest period of about 4-6 weeks. Preferably, the melphalan is administered once-daily for about 4 to about 5 days, followed by a rest period of about 4-6 weeks. The schedules can be repeated one or more times.

The COMPOUND 1 may be administered in conjunction with melphalan at any suitable dose. Suitable COMPOUND 1 doses can be in the range of about 0.5 mg/m$^2$ to about 10 mg/m$^2$, such as about 0.5 mg/m$^2$ to about 5 mg/m$^2$, or about 0.5 mg/m$^2$ to about 3 mg/mg$^2$. A suitable COMPOUND 1 dose will typically range from about 0.5 mg/m$^2$ to about 3 mg/m$^2$. Preferably, the COMPOUND 1 dose is in the range of about 1 mg/m$^2$ to about 3 mg/m$^2$. More preferably, the COMPOUND 1 dose is in the range of about 1.5 mg/m$^2$ to about 2.5 mg/m$^2$. Preferred COMPOUND 1 doses include, but are not limited to, 1.1 mg/m$^2$, 1.5 mg/m$^2$, 1.8 mg/m$^2$, 2.1 mg/m$^2$, or 2.4 mg/m$^2$. The preceding doses are suitable for any method of COMPOUND 1 administration, and are especially suitable for subcutaneous or intravenous dosing, with intravenous dosing preferred. Oral doses of COMPOUND 1 will typically be at the high end of the preceding ranges, such as about 1 mg/m$^2$ to about 7 mg/m$^2$. In one embodiment, the oral dose of COMPOUND 1 is about 2 mg/m$^2$ to about 6 mg/m$^2$, such as about 3 mg/m$^2$ to about 5 mg/m$^2$. Exemplary oral COMPOUND 1 doses include, but are not limited to, 2 mg/m$^2$, 3 mg/m$^2$, 4 mg/m$^2$, 5 mg/m$^2$ or 6 mg/m$^2$.

The COMPOUND 1 may be administered at the above-described doses with melphalan according to any suitable schedule. The COMPOUND 1 dose amounts may be constant or varied within the dosing schedule. Preferably, the COMPOUND 1 dose is maintained at a constant level during the schedule unless significant drug-related toxicity is observed, in which case subsequent doses can be reduced, for example by about 20-30%. The COMPOUND 1 may be administered on the same or different days as the melphalan. A suitable COMPOUND 1 schedule will typically range from once-daily dosing to once-weekly dosing or even once-monthly dosing. Preferably, the COMPOUND 1 is administered less frequently than once-daily, such as one dose every 2-14 days. Preferably, the COMPOUND 1 is administered every 3 to 28 days, such as every 7 to 21 days. For example, the COMPOUND 1 may be administered twice per week. In another example, COMPOUND 1 may be administered once per week. In another example, COMPOUND 1 may be administered once every two weeks. Preferably, the schedule includes a period of at least 5 days during which COMPOUND 1 is not administered, such as a period of about 7 to 21 days. Preferably, the rest period is about 10 to 17 days, such as about 10 days or about 17 days. For example, the COMPOUND 1 can be administered on days 1, 4, 8 and 11 of a 21 day cycle, wherein days 12-21 are a rest period. In another embodiment, the COMPOUND 1 can be administered on days 1, 4, 8, and 11 of a 28 day cycle, wherein days 12-28 are a rest period. In another embodiment, the COMPOUND 1 can be administered on days 1, 8, and 15 of a 28 day cycle, wherein days 16-28 are a rest period. In another embodiment, the COMPOUND 1 can be administered on days 1 and 8 of a 21 day cycle, wherein days 12-21 are a rest period. In another embodiment, the COMPOUND 1 can be administered on days 1 and 8 of a 28 day cycle, wherein days 12-28 are a rest period. In another embodiment, the COMPOUND 1 can be administered on days 1 and 15 of a 21 day cycle. In another embodiment, the COMPOUND 1 can be administered on days 1 and 15 of a 28 day cycle. In one embodiment, the COMPOUND 1 can be administered on days 1, 4, 8, 11, 22, 25, 29 and 32 of a 42 day cycle, and melphalan can be administered on days 1, 2, 3 and 4 of the 42 day cycle. In one embodiment, the COMPOUND 1 can be administered on days 15, 22 and 29 of a 42 day cycle, and melphalan can be administered on days 1, 2, 3 and 4 of the 42 day cycle. In another embodiment, the COMPOUND 1 can be administered on days 1, 4, 8, 11, 22, 25, 29, 32, 43, 50, 64, and 71 of an 84 day cycle, and melphalan can be administered on days 1, 2, 3, 4, 43, 44, 45, and 46 of the 84 day cycle. In another embodiment, the COMPOUND 1 can be administered on days 15, 22, 29, 57, 66, and 71 of an 84 day cycle, and melphalan can be administered on days 1, 2, 3, 4, 43, 44, 45, and 46 of the 84 day cycle. In another embodiment, the melphalan can be administered on days 1, 2, 3, and 4, of a 28 day cycle, and COMPOUND 1 can be administered on days 1 and 15 of the 28 day cycle. In another embodiment, the melphalan can be administered on days 1, 2, 3, and 4, of a 28 day cycle, and COMPOUND 1 can be administered on days 8 and 15 of the 28 day cycle. In another embodiment, the melphalan can be administered on days 1, 2, 3, and 4, of a 28 day cycle, and COMPOUND 1 can be administered on days 1, 8 and 15 of the 28 day cycle. In another embodiment, the melphalan can be administered on days 1, 2, 3, 4, and 5 of a 42 day cycle, and COMPOUND 1 can be administered on days 1, 8, 22 and 29 of the 42 day cycle. The schedules can be repeated one or more times.

One or more additional cancer treatments can be used in combination with the administration of the COMPOUND 1 and bortezomib or COMPOUND 1 and melphalan. Such treatments include cancer agents including, but not limited to, bortezomib, melphalan, dexamethasone and other steroids, doxorubicin, cyclophosphamide, thalidomide, lenalidomide, arsenic trioxide, and histone deacetylase inhibitors. Appropriate doses of these agents are well known in the art. In another aspect of the invention, an additional agent can be a granulocyte colony-stimulating factor (G-CSF) such as filgrastim. In a preferred embodiment, filgrastim is administered at a dose of about 5 µg/kg/day SC starting day 6 until neutrophil recovery to ANC>1000. ANC is an abbreviation for "absolute neutrophil count."

The combination therapy of the present invention may be used as part of a treatment course further involving attempts to surgically remove part or all of a cancerous growth. For instance, the combination therapy may be administered after surgical treatment of a subject to treat any remaining neoplastic or metastasized cells. Treatment can also precede surgery, in an effort to shrink the size of the tumor to reduce the amount of tissue to be excised, thereby making the surgery less invasive and traumatic.

Treating multiple myeloma with the combination therapy of the presently disclosed subject matter can further include one or more treatment courses with a radiotherapeutic agent to induce DNA damage. Radiotherapeutic agents include, for example, gamma irradiation, X-rays, UV-irradiation, microwaves, electronic emissions, radioisotopes and the like. Therapy can be achieved by irradiating the localized tumor site with the above-described forms of radiation.

Another aspect of the invention relates to methods for purging bone marrow, i.e., removing cancer cells from bone marrow, by exposing the bone marrow cells to the combination therapy of the present invention. The purged bone marrow may then be placed back into the subject from whom the bone marrow was removed, or placed into a different subject.

Materials and Methods

Reagents

COMPOUND 1 (4 mg; Cephalon, Frazer, Pa.) was dissolved in propylene glycol (800 µL) and added to 5% mannitol to generate a final stock concentration of 1 mg/mL; COMPOUND 1 stock solution was diluted to the indicated concentrations immediately before treatment. Bortezomib (Millennium Pharmaceuticals, Cambridge, Mass.) was obtained at 1 mg/mL and diluted as specified using 0.9% sodium chloride. Melphalan (Sigma, St. Louis, Mo.) was dissolved in 100 µL acid-EtOH (acid-EtOH: 47 µL concentrated HCl+1 mL of 100% EtOH) and diluted to 1 mL with phosphate-buffered saline. Formulations were prepared weekly.

Cell Lines and Primary Cells

The human myeloma cell line RPMI8226 was obtained from American Type Culture Collection (Rockville, Md.). The MM1S myeloma cell line was provided by Dr. Steven Rosen (Northwestern University, Chicago, Ill.). Normal peripheral blood mononuclear cells (PBMCs) were isolated by Histopaque® density gradient centrifugation, according to the manufacturer's protocol (Sigma-Aldrich, St. Louis, Mo.). Myeloma cell lines and PBMCs were maintained in RPMI 1640 (Omega Scientific, Tarzana, Calif.) supplemented with 10% fetal bovine serum, 2 mM L-glutamine, 100 IU/mL penicillin, 100 µg/mL streptomycin, and essential amino acids in an atmosphere of 5% carbon dioxide ($CO_2$) at 37° C.

Cell Viability Assay (MTS Assay)

Cells were seeded at $10^5$ cells/100 µL/well in 96-well plates and incubated for 24 hours. RPMI8226 and MM1S cells were cultured in the presence of vehicle, COMPOUND 1, bortezomib, melphalan, COMPOUND 1+bortezomib, or COMPOUND 1+melphalan for 48 hours. After the incubation period, cell viability was quantified using the CellTiter 96® AQueous Non-Radioactive Cell Proliferation Assay (Promega, Madison, Wis.). Each well was treated with MTS (3-(4,5-dimethylthiazol-2-yl)-5-(3-carboxymethoxyphenyl)-2-(4-sulfophenyl)-2H-tetrazolium, inner salt) for 1 to 4 hours, after which absorbance was recorded at 490 nm. The quantity of formazan product as measured by absorbance at 490 nm is directly proportional to the number of living cells in culture.

In vitro synergy between COMPOUND 1 and bortezomib or melphalan was assessed using the median effect method of Chou and Talalay (30). Combination indices (CIs) were calculated separately for each combination. Drug interactions were determined synergistic if the CI was less than 0.9 or antagonistic if the CI was greater than 1.1. CIs between 0.9 and 1.1 were considered to indicate additive drug effects (31).

Apoptotic Assay by Annexin V and Propidium Iodide Staining

To quantify apoptosis in response to drug treatment, RPMI8226 cells ($5 \times 10^5$ cells per well) were incubated with vehicle or PIs at 37° C. and 5% $CO_2$ for 30 hours. As a positive control, cells were incubated with 250 ng/mL of actinomycin D for 24 or 48 hours. Cells were then washed twice with phosphate-buffered saline, resuspended in binding buffer (100 mM HEPES/NaOH, pH 7.5 containing 1.4 M NaCl and 25 mM $CaCl_2$), and stained with fluorescein isothiocyanate (FITC)-conjugated annexin V and with the fluorescent dye propidium iodide (PrI), according to the manufacturer's protocol (BioVision, Mountain View, Calif.). For each drug treatment, $1 \times 10^5$ gated events were recorded. Cells negative for both PI and annexin V staining were considered live; annexin V-positive, PrI-negative cells were considered early apoptotic; annexin V-positive, PrI-positive cells were considered late apoptotic. Flow cytometric analyses were performed using a Beckman Coulter FC500 cytometer with Cytomics CXP software (Beckman Coulter, Fullerton, Calif.).

SCID Mice

Six- to 8-week-old male severe combined immunodeficient (SCID) mice were obtained from the Jackson Laboratory (Bar Harbor, Me.) and maintained in a specific pathogen-free area in our animal resources facility. All animal studies were conducted according to protocols approved by the Institutional Animal Care and Use Committee. Animals were anesthetized with ketamine, xylazine, and isoflurane prior to surgery and were euthanized when tumors reached 2 cm in diameter.

Intramuscular Tumor Xenograft Models

To establish the LAGκ-1A tumor (sensitive to bortezomib and melphalan), a bone marrow biopsy was obtained from a female MM patient who had progressed while on lenalidomide treatment Immediately subsequent to this biopsy, the patient was treated with a combination of melphalan and bortezomib and showed a response. Biopsy tissue was surgically implanted in the hind limbs of anesthetized SCID mice and passaged through succeeding generations (32). The LAGκ-1B tumor (resistant to bortezomib and melphalan) originated from the same patient as LAGκ-1A but was generated from a biopsy taken when the patient was progressing while receiving treatment with bortezomib and melphalan (32).

Myeloma tumors (LAGκ-1A or LAGκ-1B) were excised from an anesthetized donor mouse, sectioned into 20 to 40 $mm^3$ pieces, and surgically implanted into the left superficial gluteal muscle of anesthetized naive SCID mice. Recipient mice received weekly injections of anti-asialo GM1 rabbit serum (Wako Bioproducts, Richmond, Va.) to further suppress immune activity. Mice were blindly assigned to one of the experimental groups, and treatment was initiated 7 to 21 days after tumor implantation. COMPOUND 1 was administered via oral gavage daily (0.5-5.0 mg/kg) or twice weekly (5-10 mg/kg). COMPOUND 1 was also administered twice weekly (W, F) via either IV injection (0.5-3.0 mg/kg) or oral gavage (10 mg/kg), as specified. Melphalan (1 mg/kg) was provided via weekly intraperitoneal (IP) injections (W). Bortezomib (0.5 mg/kg) was dispensed twice weekly (T, Th) via IV injection. Control treatment consisted of COMPOUND 1 diluent (3.2 mL 5% mannitol and 800 µL propylene glycol) alone.

Human Immunoglobulin G (hIgG) Enzyme-Linked Immunosorbent Assay (ELISA)

Serum levels of hIgG secreted by LAGκ-1A tumors (LAGκ-1B tumors do not secrete paraprotein) were quantified by ELISA as a protein marker of tumor growth. Mice bearing MM tumors underwent weekly retro-orbital bleeds. Resulting samples were spun at 13,000 rpm for 30 minutes to isolate serum. The hIgG ELISA kit (Bethyl Laboratories, Montgomery, Tex.) was used according to the manufacturer's specifications. Absorbance at 450 nm with a reference wavelength of 550 nm was determined on a µQuant microplate spectrophotometer with KC Junior software (Bio-Tek Instruments, Winooski, Vt.). Data graphed are the mean±SEM with n=7-8 mice/group.

Determination of Tumor Volume

As a direct measurement of tumor growth, calipers were used to assess tumor volume weekly, and the formula for an ellipsoid volume was applied ($\frac{4}{3}\pi \times [width/2]^2 \times [length/2]$).

Percent Inhibition of Tumor Growth

Percent inhibition of tumor growth is represented as the tumor volume of the test drug group over the tumor volume of the untreated group (T/C). The optimal value is the minimal T/C ratio that reflects the maximal tumor growth inhibition achieved. The criterion for efficacy for the T/C ratio is ≤42%, according to National Cancer Institute (NCI) standard criteria (44).

Tumor Growth Delay

Efficacy of drug therapy against tumors was standardized to the time (t) required for the untreated tumor to grow to a determined size based on the greatest difference in time to reach a tumor volume between the control and treatment group. This value can be represented as the growth delay (in days) between treated and control ($t_t$-$t_c$) (44).

Immunohistochemical Analysis of Apoptosis-Inducing Factor (AIF) Expression in Tumor Cells LAGκ-1B tumors were fixed in 4% paraformaldehyde and cut into 5 μm sections. Briefly, sections were blocked with Tris-buffered saline with 0.05% Tween-20 (TBST) and 3% BSA for 1 hour at room temperature and then incubated overnight with a rabbit antibody against AIF (Sigma, St. Louis, Mo.). The sections were washed three times with TBST and treated with horse radish peroxidase(ARH)-conjugated anti-rabbit antibody (KPL, Gaithersburg, Md.) diluted 1:500 in TBST at room temperature for 2 hours. The slides were washed three times in TBST and placed in 3-amino-9-ethylcarbazole (AEC) buffer for 5 minutes, and color was detected using an AEC kit (Dako, Glostrup, Denmark). Staining was documented using an Olympus BX51 microscope (Olympus Imaging America Inc., Center Valley, Pa.) and analyzed by Microsuite Biological Suite program (Olympus BX51).

Statistical Analysis

Tumor growth and hIgG levels were analyzed in terms of treatment group means and standard error. Student's t-test was applied to determine the statistical significance of differences between treatment groups. Minimal significance level was P<0.05.

EXAMPLES

The data presented in the following Examples suggest that the combination therapy of the present invention may provide similar or greater efficacy in MM when COMPOUND 1 and bortezomib or COMPOUND 1 and melphalan are combined in low doses as compared with standard-dose single-agent therapy. In this way, drug-associated toxicities, such as peripheral neuropathy for bortezomib and myelosuppression for melphalan, may be reduced or avoided (40,41). In the experiments presented here, mice treated with combination therapies tolerated treatment well and experienced little or no tumor progression.

Example 1

COMPOUND 1 is Cytotoxic to MM Cells and Synergistic when Combined with Anti-MM Agents In Vitro RPMI8226 and MM1S cells were cultured in the presence of increasing concentrations of COMPOUND 1 (0.1-10 nM). After 48 hours, cell viability was assessed with the MTS assay. COMPOUND 1 induced concentration-dependent inhibition of viability in both cell lines (FIG. 1A). Results were similar when cells were treated with COMPOUND 1 for 24 or 72 hours (data not shown).

We next examined cell viability in the presence of COMPOUND 1 plus the PI bortezomib or the chemotherapeutic agent melphalan. First, MM1S cells were incubated with a fixed concentration of COMPOUND 1 (1.75 nM) and increasing concentrations of bortezomib (0.5-2.5 nM) for 48 hours. At bortezomib concentrations≤1.5 nM, the cytotoxic effects of COMPOUND 1 were enhanced. For example, as single agents, COMPOUND 1 (1.75 nM) and bortezomib at the lowest concentration (0.5 nM) each inhibited cell viability by approximately 16%. However, when COMPOUND 1 (1.75 nM) was combined with bortezomib (0.5 nM), cell viability decreased by approximately 43% (FIG. 1B). Chou-Talalay equations were applied to confirm the synergy of this combination (CIs, 0.74-0.85) (30,31). Similar results were obtained when the experiment was repeated with RPMI8226 cells (data not shown).

Figure 1C:
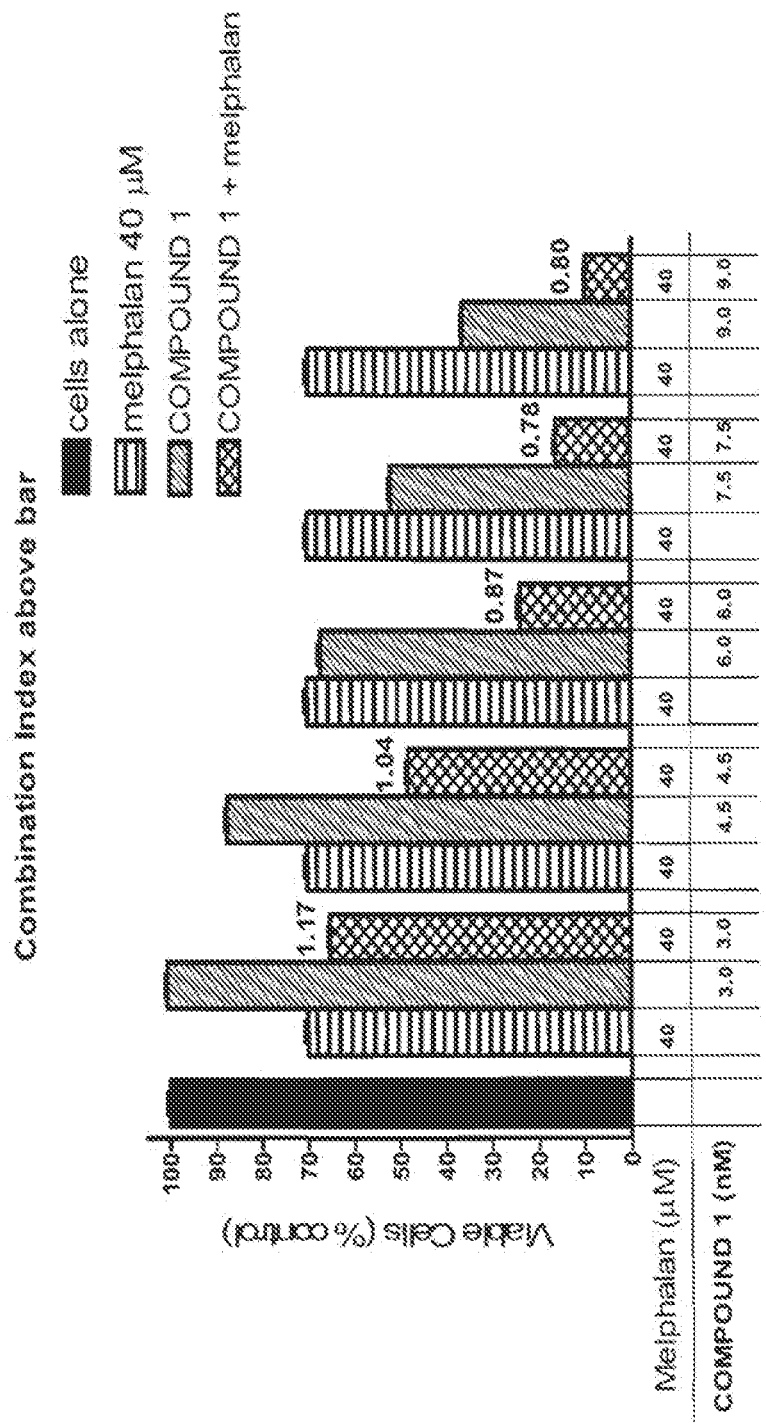

When RPMI8226 cells were incubated with melphalan (40 μM) and concentrations of COMPOUND 1≥6.0 nM ($IC_{50}$=8.5 nM), synergistic inhibition of viability was observed (CIs, 0.78-0.87). For example, cell viability decreased by approximately 30% in the presence of single-agent melphalan (40 μM) and by 64% in the presence of single-agent COMPOUND 1 (9.0 nM). When both drugs were applied simultaneously, cell viability was reduced by 90% (FIG. 1C). Together, these results demonstrate that COMPOUND 1 combined with bortezomib or melphalan can synergistically suppress MM cell viability.

Example 2

COMPOUND 1 and Bortezomib are Selectively Cytotoxic for Neoplastic Cells

In order for therapy with two or more PIs to be feasible in vivo, the combination must spare non-neoplastic cells. Therefore, we tested the effects of COMPOUND 1 plus bortezomib on the viability of normal PBMCs. A healthy donor's PBMCs were cultured for 48 hours in the presence of COMPOUND 1 alone, bortezomib alone, or both agents together, and cell viability was quantified by MTS assay. Monotherapy with either PI near its $IC_{50}$ in MM cells only modestly inhibited the viability of PBMCs (approximately 75% and 85% viable cells when PBMCs were treated with 9 nM COMPOUND 1 and 9 nM bortezomib, respectively) (FIGS. 2A, B). Co-incubation with both PIs did not further decrease or slightly increased cell viability compared with administration of either agent alone (3%-23% decrease in cell viability when both PIs were administered at all concentrations tested) (FIGS. 2A, B). Similar results were obtained with PBMCs derived from a second healthy donor (FIG. 2C). To determine whether PBMCs were vulnerable to higher concentrations of PIs, PBMCs were cultured with COMPOUND 1 up to 120 nM. When compared with controls, no significant differences in cell viability were detected at any concentration tested (FIG. 2D). Similar results were obtained when PBMCs were incubated with concentrations of bortezomib up to 120 nM (data not shown). Therefore, the combination therapy of the present invention provides enhanced efficacy against MM without increasing toxicity to normal cells.

Example 3

COMPOUND 1 in Combination with Bortezomib Induces Apoptosis of MM Cells

Figure 3A:
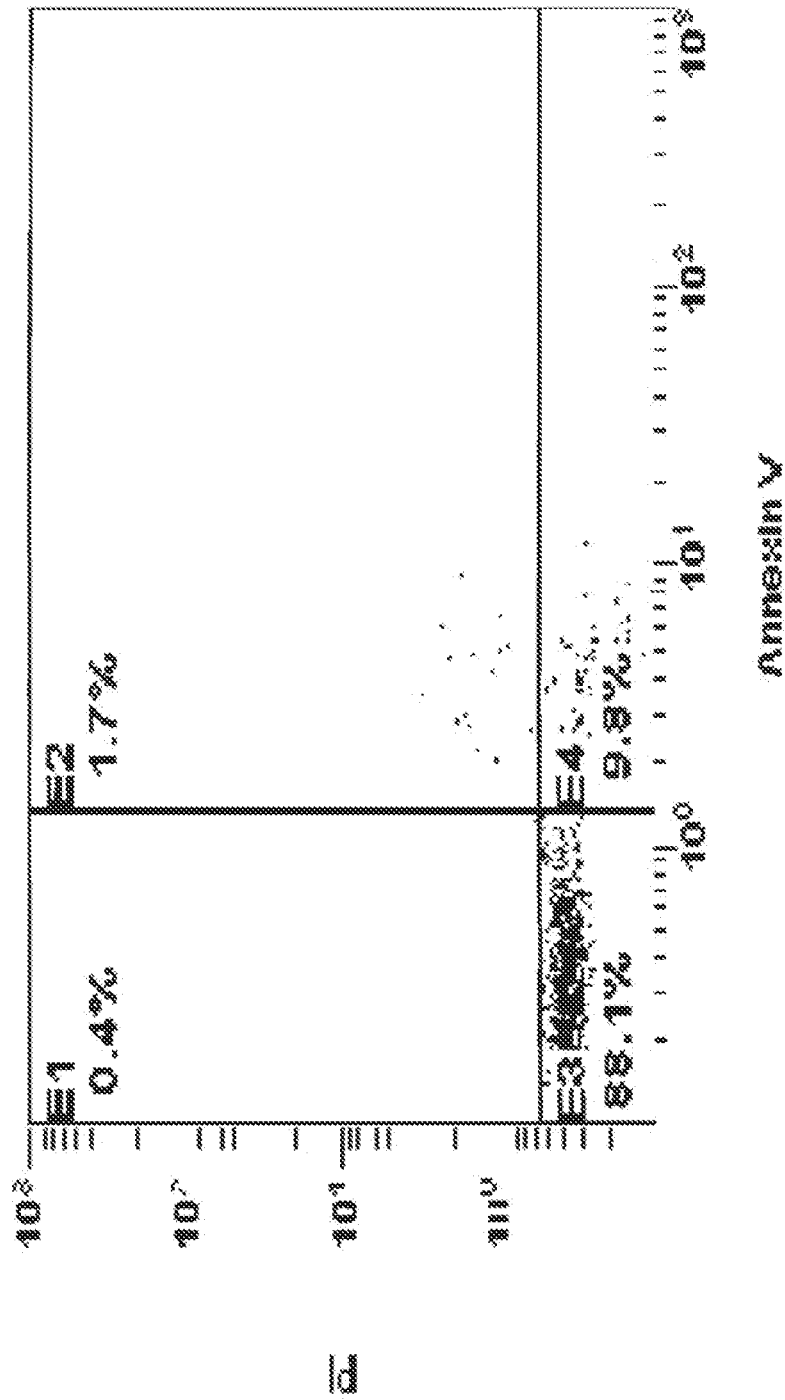
FIG. 3. COMPOUND 1 combined with bortezomib induces apoptosis in MM cells. RPMI8226 cells were incubated with (A) vehicle control, (B) COMPOUND 1 (2.5 nM), (C) bortezomib (2.5 nM), or (D) COMPOUND 1 (2.5 nM) plus bortezomib (2.5 nM) for 30 hours, and the percentage of staining positive for propidium iodide (PrI) and annexin V was quantified using flow cytometric analysis. Cells in early apoptosis are PrI negative and annexin V positive.
Figure 3B:
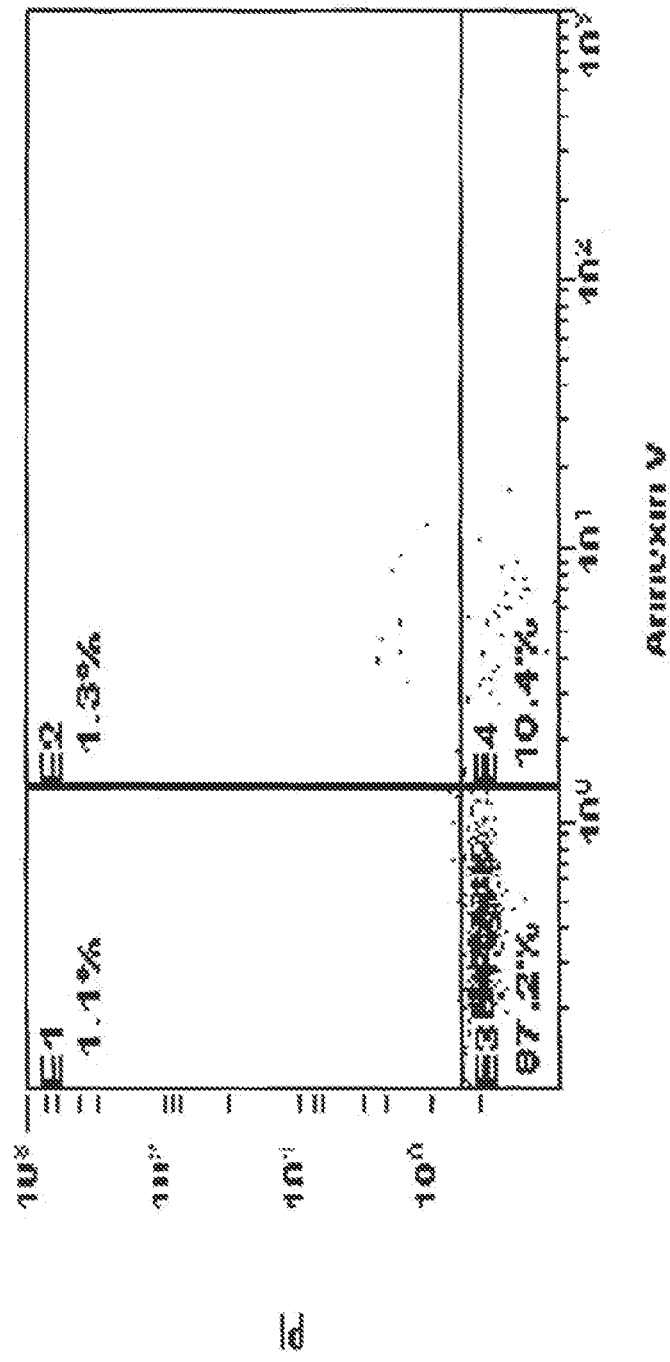

To determine whether the reduction in cell viability observed following treatment of MM cells with COMPOUND 1 and bortezomib was due to apoptosis, we incubated RPMI8226 cells with both agents (at 2.5 nM for each drug) for 30 hours and measured the fraction of cells stained with the viability dye PrI and the apoptosis marker annexin V. The proportion of cells in early apoptosis (PrI−/Annexin V+) was greater following treatment with both PIs (38.9% of cells) than with either agent alone (10.4% and 17.5% of cells treated with 2.5 nM COMPOUND 1 or 2.5 nM bortezomib, respectively) (FIG. 3). The proportion of cells in late apoptosis (PrI+/Annexin V+) or necrosis (PrI+/Annexin V−) did not vary among treatment groups at this time point.

Example 4

Single-Agent COMPOUND 1 Inhibited Human MM Tumor Growth In Vivo

Because COMPOUND 1 demonstrates potent anti-MM effects as a single agent and in combination in vitro, we next conducted a series of in vivo studies. For these experiments, we utilized mice bearing LAGκ-1A (bortezomib- and melphalan-sensitive) and LAGκ-1B (bortezomib- and melphalan-resistant) tumors, both of which were originally derived from bone marrow biopsies of an MM patient. These tumors closely resemble human MM and have been passaged through multiple generations of mice with consistent growth and chemoresistance patterns. Following intramuscular implantation of tumor tissue, mice underwent twice-weekly treatment with COMPOUND 1 at escalating doses ranging from 0.1 to 3 mg/kg IV or 10 mg/kg orally. Control group mice received COMPOUND 1 diluent.

Administration of single-agent COMPOUND 1 IV yielded a dose-dependent decrease in paraprotein secretion from LAGκ-1A tumors. Lower doses of COMPOUND 1 reduced tumor hIgG secretion, and higher doses rendered serum hIgG levels essentially undetectable ($P=0.0001$ for 1 mg/kg and $P=0.0002$ for 3 mg/kg IV COMPOUND 1, compared with control at 28 days of drug treatment) (FIG. 4A).

Unlike bortezomib, COMPOUND 1 also shows activity as an oral formulation (28,29). Within 2 weeks of treatment with oral COMPOUND 1, serum hIgG levels were significantly lower than in control-treated animals ($P=0.0007$). By 28 days of treatment with oral COMPOUND 1, serum hIgG levels were negligible ($P=0.0001$, compared with control-treated animals) (FIG. 4A).

In addition to effects on paraprotein levels, single-agent COMPOUND 1 slowed increases in LAGκ-1A tumor volume compared with vehicle-treated mice. After 4 weeks of drug treatment, COMPOUND 1 administered IV at 1 or 3 mg/kg resulted in an approximately 15-fold reduction in the volume of tumors, compared with control-treated xenografts at the same time point ($P=0.0001$ for each dose compared with control) (FIG. 4B). COMPOUND 1 delivered orally also inhibited tumor growth. After only 14 days of treatment with oral COMPOUND 1, a marked reduction in tumor volume, compared with control-treated tumors, was observed ($P=0.0002$), a difference that persisted throughout the duration of the study (FIG. 4B). Similarly, COMPOUND 1 monotherapy also resulted in a statistically significant reduction of 1 g levels and tumor volumes in a different MM tumor, LAGλ-1.

The effect of COMPOUND 1 on tumor volume was also tested in mice bearing the bortezomib-resistant nonsecretory LAGκ-1B tumor (FIG. 4C). As with the LAGκ-1A tumors, COMPOUND 1 inhibited tumor growth, both as an IV injection and as an oral formulation. Compared with control-treated mice, mice treated with 3 mg/kg IV or 10 mg/kg oral COMPOUND 1 showed tumors that were approximately 8 to 12 times smaller after 14 days of treatment ($P=0.0008$ and $P=0.0028$, respectively) (FIG. 4C). Because LAGκ-1B tumors used in these experiments are nonsecretory, mice bearing these tumors were not tested for serum hIgG levels.

Example 5

Figure 5B:
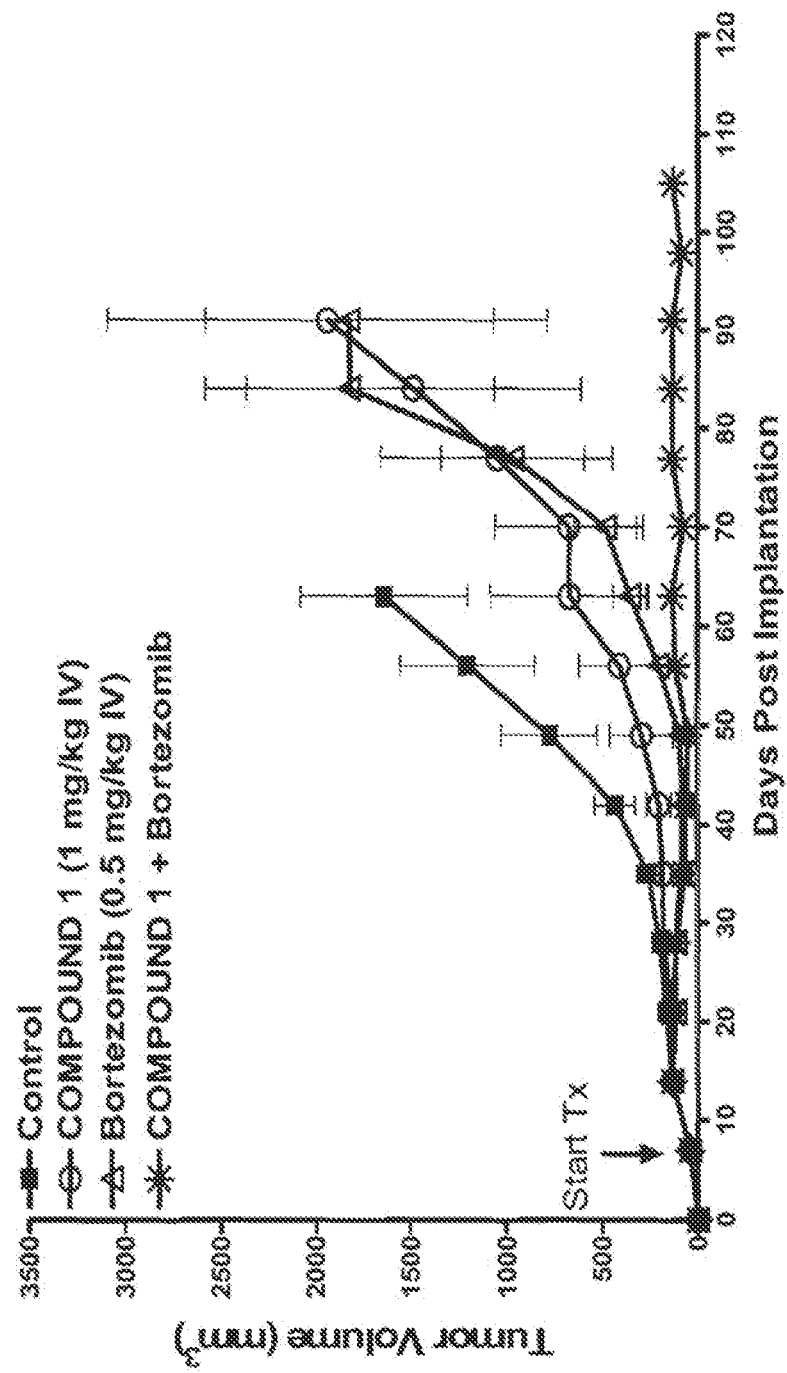
FIG. 5. COMPOUND 1 combined with bortezomib or melphalan markedly inhibits the growth of myeloma tumors. Treatment was initiated on day 7 in all of these studies. Mice bearing LAGκ-1A or LAGκ-1B tumors were treated twice weekly with vehicle control, COMPOUND 1 alone (1 mg/kg), bortezomib alone (0.5 mg/kg), or COMPOUND 1 plus bortezomib (A-C). Differences in growth between control-treated and combination therapy-treated LAGκ-1A tumors first became significant 28 days after the initiation of therapy (hIgG: P=0.0028; tumor volume: P=0.0265, A and B, respectively). LAGκ-1B-bearing mice treated with COMPOUND 1 plus bortezomib developed significantly smaller tumors (C) than vehicle-treated mice after 21 days of therapy (P=0.0014). COMPOUND 1 combined with bortezomib delayed the progression of LAGκ-1B tumor volume from 35 to 70 days. Furthermore, after 28 days of treatment, tumors in mice receiving combination therapy were also smaller than those in mice treated with either PI alone (P=0.0039 and P<0.0001, for comparisons with COMPOUND 1 alone and bortezomib alone, respectively). COMPOUND 1 combined with melphalan inhibits the growth of LAGκ-1A tumors. Mice bearing LAGκ-1A tumors were treated twice weekly with vehicle control, twice weekly with COMPOUND 1 alone (1 mg/kg), once weekly with melphalan alone (1 mg/kg), or twice weekly with COMPOUND 1 plus once weekly with melphalan (D-F). After 3 weeks of treatment, tumors exposed to the combination of COMPOUND 1 and melphalan showed a marked reduction in both hIgG secretion (P=0.0012) and tumor volume (P=0.032) compared with vehicle-treated tumors (D and E, respectively). COMPOUND 1 combined with melphalan also prevents increases in LAGκ-1B tumor volume. Mice bearing LAGκ-1B tumors were treated with vehicle control twice weekly, COMPOUND 1 alone twice weekly (1 mg/kg), melphalan alone once weekly (3 mg/kg), or COMPOUND 1 twice weekly plus melphalan once weekly. When COMPOUND 1 was combined with melphalan, tumor volumes were reduced to nearly undetectable levels (F) following three weeks of treatment (P=0.0019). Data in parts A-F are presented as means±standard error of the mean, with 7-8 mice per group.
Figure 6A:
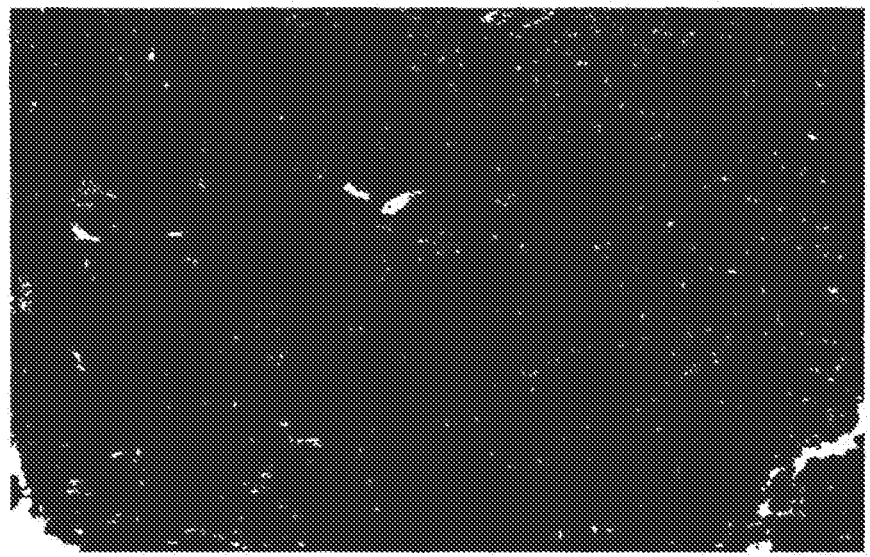
FIG. 6. LAGκ-1B tumors treated with COMPOUND 1 and bortezomib show increased expression of the apoptotic marker apoptosis-inducing factor (AIF). Tumors excised from LAGκ-1B-bearing mice following treatment with vehicle control (A), COMPOUND 1 (1 mg/kg) alone (B), bortezomib (0.5 mg/kg) alone (C), or both agents (D) were sectioned and stained for AIF. E-H, Sections from the same tumors as A-D stained with isotype controls. Slides were stained simultaneously.
Figure 6E:
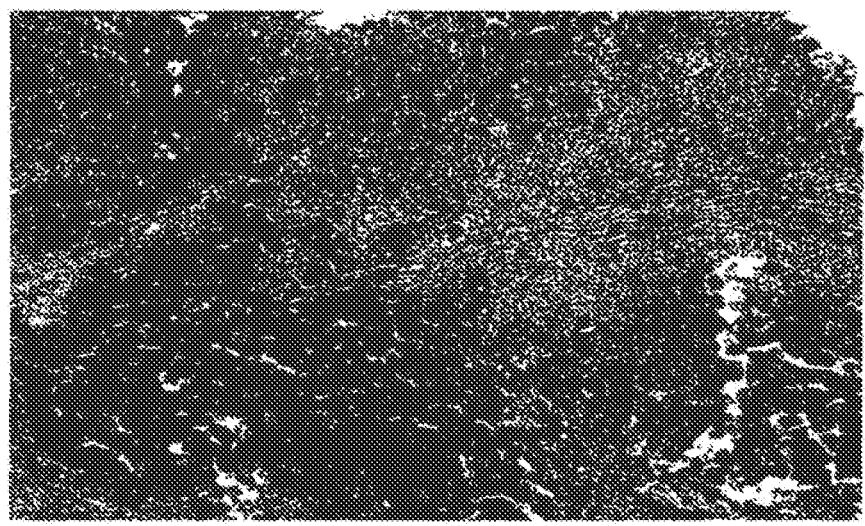
Figure 6B:
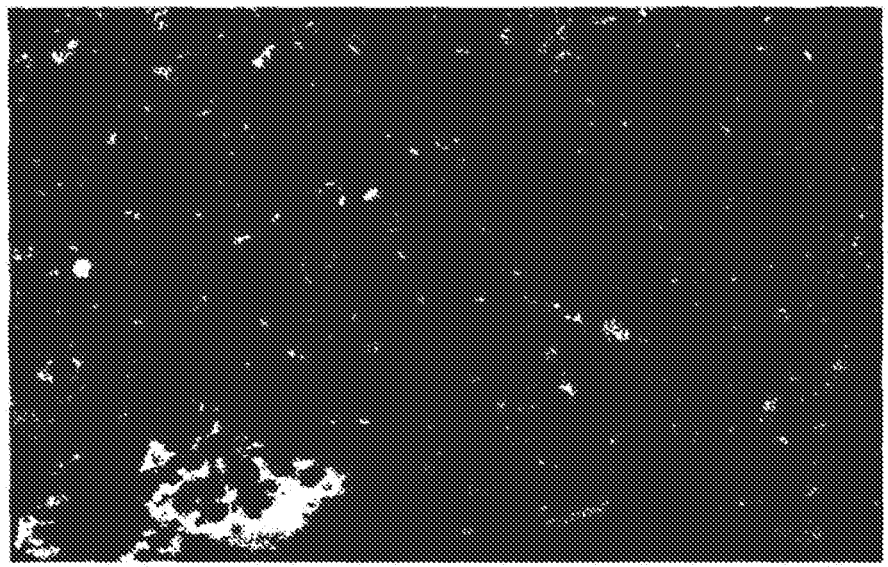
Figure 6F:
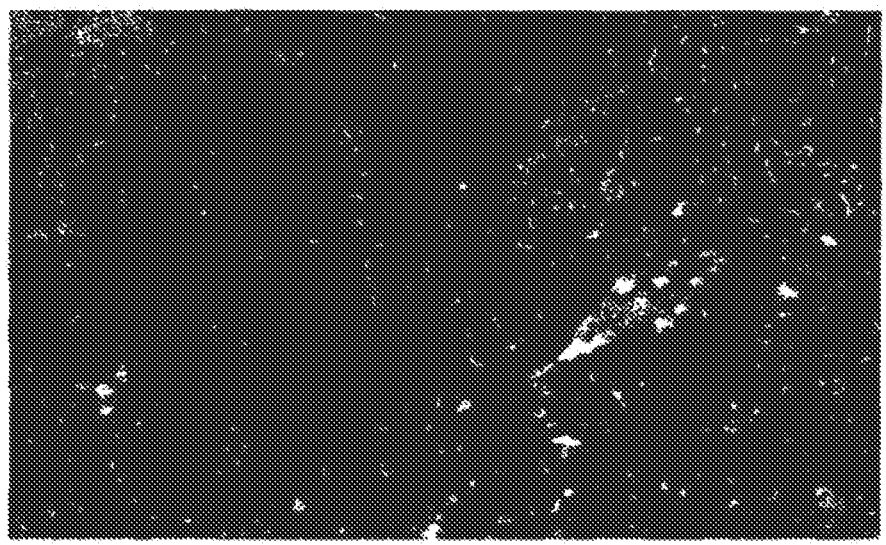
Figure 6C:
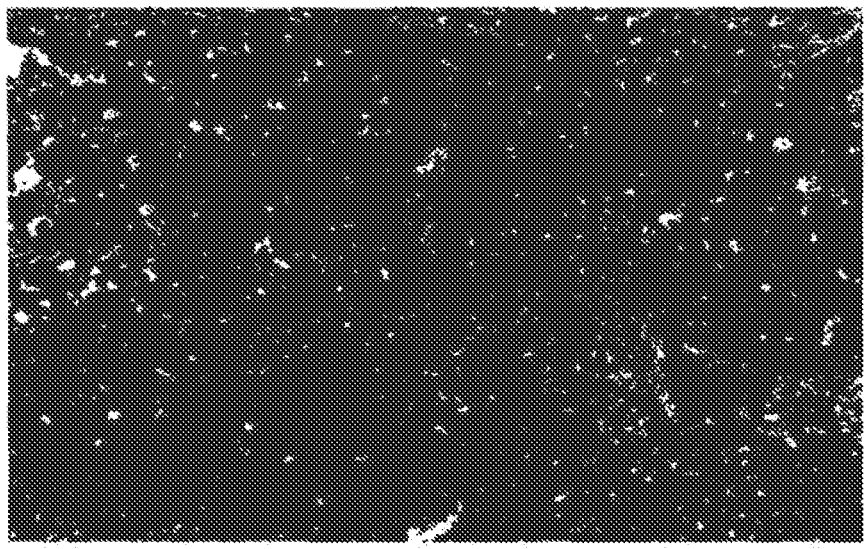
Figure 6G:
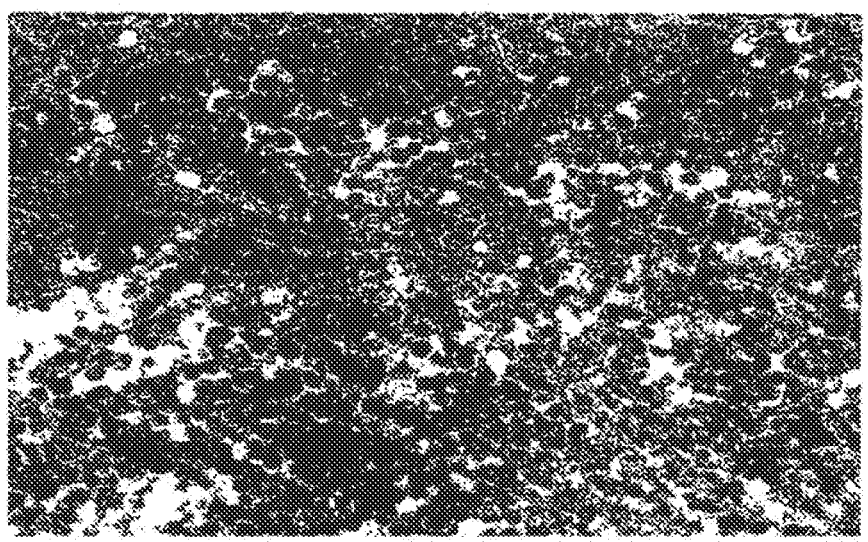
Figure 6D:
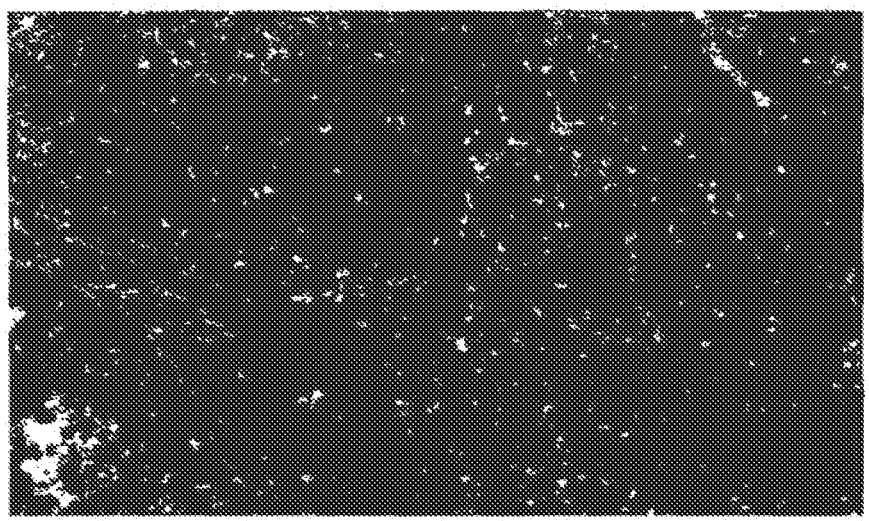
Figure 6H:
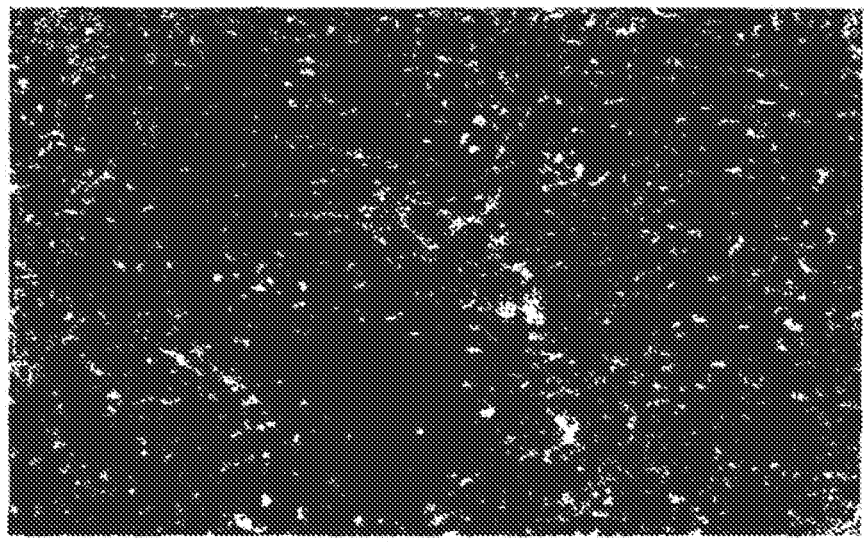

COMPOUND 1 in Combination with Bortezomib Inhibits the Growth of Bortezomib-Sensitive LAGκ-1A MM Tumors Because COMPOUND 1 combined with bortezomib induces synergistic apoptosis of MM cells in vitro, we tested this combination on human MM tumors in vivo. We selected drug concentrations with suboptimal single-agent antitumor activity. As monotherapy, both COMPOUND 1 (1 mg/kg IV) and bortezomib (0.5 mg/kg IV) only partially inhibited serum hIgG levels and volume of LAGκ-1A tumors compared with vehicle control (FIGS. 5A, B). However, gradual progression of tumor growth, as measured by both paraprotein secretion and tumor volume, persisted despite treatment with single-agent COMPOUND 1 or bortezomib. In contrast, co-administration of COMPOUND 1 with bortezomib at the same doses eliminated detectable paraprotein secretion and increases in tumor volume. Differences in growth between control-treated and combination therapy-treated LAGκ-1A tumors first became significant 28 days after the initiation of therapy ($P=0.0028$ for serum hIgG levels and $P=0.0265$ for tumor volume) (FIGS. 5A, B). Complete inhibition of tumor progression was maintained throughout the duration of the experiment (110 days). Furthermore, when mice treated with COMPOUND 1 plus bortezomib were euthanized, examination of excised hind limbs revealed only muscle mass and no tumor tissue, as only red muscle fibers were visible and not any plasma cells on examination. Tumors implanted at study initiation had regressed completely. Further support for this effect was shown with determination of hIg levels (FIG. 5A). Notably, the toxicity profiles were similar between mice dosed with the combination and single agent bortezomib or COMPOUND 1. All of the mice (7/7) treated with the combination of PIs remained alive throughout the duration of the study In previous studies, changes in the volume of hIgG-secreting myeloma tumors were tightly correlated with changes in serum human paraprotein levels (15,32). However, in these experiments, paraprotein secretion from tumors treated with single-agent COMPOUND 1 or bortezomib plateaued and then declined beginning on the 63rd day of treatment (study day 70); in contrast, tumor volumes continued to increase throughout the duration of the study (FIGS. 5A, B). Therefore, as monotherapy each agent suppressed increases in serum hIgG levels more effectively than tumor volume.

To verify these results, samples from day 70 onward were retested by ELISA, and decreasing hIgG levels were confirmed. The inverse relationship between hIgG levels and tumor volumes suggests that a population of nonsecretory, drug-resistant MM cells exist, perhaps derived from cancer stem cells. Thus, either bortezomib or COMPOUND 1 alone may act primarily against the antibody-secreting mature plasma cell component of MM (22), without affecting the small stem cell population responsible for delayed tumor growth (24).

In contrast, LAGκ-1A-bearing mice that received a combination of COMPOUND 1 and bortezomib showed a marked and sustained lack of tumor growth, as assessed by both hIgG and tumor volume measurements, throughout the 110-day study. These data indicate that MM cells that proliferate without producing paraprotein in the presence of single-agent PIs are sensitive to the combination of COMPOUND 1 and bortezomib.

Example 6

Combination Therapy with COMPOUND 1 and Bortezomib Overcomes Drug Resistance in Bortezomib-Resistant LAGκ-1B Tumors LAGκ-1B tumors are resistant to bortezomib; and, indeed, either PI alone (0.5 mg/kg IV bortezomib or 1 mg/kg IV COMPOUND 1) only modestly suppresses the growth of these tumors (FIG. 5C). In contrast, LAGκ-1B-bearing mice treated with COMPOUND 1 (1 mg/kg) plus bortezomib (0.5 mg/kg) developed significantly smaller tumors than vehicle-treated mice after only 21 days of therapy (P=0.0014). Furthermore, after 28 days of treatment, tumors in mice receiving combination therapy were also smaller than those in mice treated with either PI alone (P=0.0039 and P<0.0001, for comparisons with COMPOUND 1 alone and bortezomib alone, respectively) (FIG. 5C). In order to determine the time to tumor progression, dosing of mice in the combination-therapy group continued. Compared with tumors treated with single-agent PIs, progression of tumor volume in the combination-therapy group was delayed by 100% (from 35 days to tumor progression for mice treated with single-agent PIs versus 70 days to tumor progression for animals treated with both PIs). Finally, the overall survival of each treatment group was documented. Compared with vehicle-treated mice, mice receiving combination therapy lived 150% longer (70 days versus 28 days) in the cohort receiving the combination regimen. Mice treated with either PI alone survived 20% longer than vehicle-treated mice (data not shown). Mice treated with the combination showed only one mouse with a possible drug-related death by day 70 and mice treated with either single agent also suffered one death each related to toxicity. Together, these data demonstrate that COMPOUND 1 combined with bortezomib can overcome bortezomib resistance in human MM in vivo.

Example 7

COMPOUND 1 Combined with Melphalan Inhibits the Growth of LA GK-1A and LAGκ-1B Tumors Because COMPOUND 1 synergizes with melphalan to decrease viability in cultured MM cells, and bortezomib enhances the anti-MM effects of melphalan in both laboratory (11) and clinical studies (33), we evaluated the efficacy of this alkylating agent with COMPOUND 1 in vivo. Treatment with single-agent melphalan weekly at a low dose (1 mg/kg IP) had no effect on serum hIgG levels or tumor volumes in LAGκ-1A-bearing mice. Likewise, administration of single-agent COMPOUND 1 (1 mg/kg IV) resulted in a nonsignificant decrease in both paraprotein secretion and tumor volume. However, after 3 weeks of treatment, tumors exposed to both COMPOUND 1 and melphalan showed a marked reduction in both hIgG secretion (P=0.0012) and tumor volume (P=0.032) compared with vehicle-treated tumors (FIGS. 5D, E). A similar result was obtained in mice bearing bortezomib- and melphalan-resistant LAGκ-1B tumors. Single-agent melphalan at 3 mg/kg IP (3 times higher than the dose administered to LAGκ-1A-bearing mice) or COMPOUND 1 at 1 mg/kg IV (the same dose administered to LAGκ-1A-bearing mice) partially inhibited increases in tumor volume, but when COMPOUND 1 was combined with melphalan tumor volumes were reduced to practically undetectable levels following three weeks of treatment (FIG. 5F).

In contrast to single-agent treatment, tumor growth was prevented as long as combination therapy continued in mice bearing either tumor type (63 days of treatment in the LAGκ-1A mice and 49 days of treatment in the LAGκ-1B mice). Furthermore, the tolerability of combination therapy was similar to that of each agent alone (data not shown).

Example 8

Tumors from LAGκ-1B Mice Treated with COMPOUND 1 and Bortezomib Show Elevated Expression of Apoptosis-Inducing Factor Tumors from LAGκ-1B-bearing mice were excised post-treatment and stained with AIF, a marker of apoptosis. Tumors treated with single-agent COMPOUND 1 or bortezomib showed elevated AIF expression when compared with vehicle-treated tumors. However, AIF expression is further increased in tumors taken from animals treated with both PIs (FIG. 6). Tumors from LAGκ-1A-bearing mice that received COMPOUND 1 plus bortezomib were not available for histological analysis due to lack of available xenograft samples following complete tumor regression in this treatment group.

Example 9

Single-Agent Oral COMPOUND 1 Inhibited Human MM Tumor Growth In Vivo

These experiments were similar to those described in Example 4 and used mice bearing LAGκ-1A or LAGκ-1B tumors originally derived from human bone marrow biopsies. Seven days following intramuscular implantation of tumor tissue (20-40 mm$^3$, surgically implanted into the left hind limb superficial gluteal muscle), mice underwent daily or twice-weekly treatment with COMPOUND 1 at escalating doses ranging from 0.5 to 5 mg/kg orally each day or 5 to 10 mg/kg orally twice per week. Control group mice received COMPOUND 1 diluent.

Single-agent COMPOUND 1 administered orally significantly inhibited tumor growth in LAGκ-1A-bearing mice. COMPOUND 1 administered orally and daily at 3 mg/kg has moderate anti-myeloma activity for both human IgG levels and tumor volumes. A significant inhibition of both human paraprotein secretion and reduction of tumor volume was observed as soon as three weeks (day 28 from implantation of tumor tissue) following initiation of treatment with COMPOUND 1 at 10 mg/kg twice weekly (hIgG: P=0.0011; tumor volume: P=0.001) (FIGS. 7A and 7B). At day 35, daily administration of the PI at 5 mg/kg also resulted in significant tumor inhibition (hIgG: P<0.0001; tumor volume: P<0.0001) (FIGS. 7A and 7B). Statistical significance was maintained throughout the remainder of the study. Percentage T/C's of 29.3%, 17.3%, 6.1%, 6.1%, and 10.6% on days 21, 28, 35, 42, and 49, respectively, were obtained for mice dosed twice weekly with COMPOUND 1 at 10 mg/kg. Tumor volume growth to 700 mm$^3$ was delayed by 93.8% (30.5 days, from day 32.5 for control compared to day 63 for COMPOUND 1 at 10 mg/kg) in animals receiving this treatment regimen when compared to animals receiving no treatment. Similarly, T/C's of 25.3%, 5.3%, 2.7%, and 2.1% on days 28, 35, 42, and 49, respectively, were obtained for mice dosed daily with COMPOUND 1 at 5 mg/kg. Tumor volume growth to 87.5 mm$^3$ was delayed by 530% (53 days, from day 10 for control compared to day 63 for COMPOUND 1 at 5 mg/kg) in animals receiving this treatment regimen when compared to the untreated control group. Overall, the results of these studies show a marked reduction of tumor size and delay of tumor growth in LAGκ-1A-bearing mice for both the 10 mg/kg twice weekly and 5 mg/kg daily regimens of COMPOUND 1. Furthermore, all mice (15/15) dosed twice weekly with the PI at 10 mg/kg survived the five weeks of dosing and the three week dosing-free follow-up period. Two of fifteen mice in the daily 5 mg/kg group died of drug-related toxicity. Moreover, body weight measured at treatment cessation (day 42) was not significantly different between pre- and post-treatment levels for both treatment groups (FIG. 7C).

The effect of single-agent COMPOUND 1 dosed orally in SCID mice bearing nonsecretory LAGκ-1B tumors was also evaluated. Similar to the results obtained in LAGκ-1A-bearing mice, it significantly inhibited tumor growth without significant loss of body weight. At day 35, 5 mg/kg administered daily or 10 mg/kg twice weekly resulted in significant tumor volume inhibition (P=0.0327; P=0.0018, respectively) (FIG. 7D). Tumor volume growth to 300 mm$^3$ was delayed by 35.5% (11 days, from day 31 for control compared to day 42 for COMPOUND 1-treated group) in animals receiving 5 mg/kg daily compared to animals receiving no treatment. Percentage T/C's on days 35, 42, 49, and 56 were 21.6%, 27.5%, 26.1%, and 30.5%, respectively, for mice dosed twice weekly with COMPOUND 1 at 10 mg/kg. Tumor volume at 220 mm$^3$ was delayed by 50% (14 days, from day 28 for control compared to day 42 for COMPOUND 1-treated mice) in animals receiving 10 mg/kg twice weekly when compared to the untreated control group.

CONCLUSIONS

COMPOUND 1 has significant single-agent anti-MM activity in cell lines in vitro and human tumor models in vivo when administered both intravenously and orally at well-tolerated doses. COMPOUND 1 had negligible cytotoxic effects on normal peripheral blood mononuclear cells in vitro, even at concentrations that were ten-fold higher than those that produce cytotoxic effects on MM cells (data not shown). COMPOUND 1 potentiates the anti-MM activity of a second PI, bortezomib. Administration of these two PIs together shows synergistic anti-MM effects in vitro and prevents the growth of bortezomib-sensitive LAGκ-1A tumors and markedly delays progression of bortezomib-resistant LAGκ-1B tumors by more than 100% when compared to monotherapy with either PI. Notably, higher doses of COMPOUND 1 were not necessary to overcome in vivo drug resistance to bortezomib. Sub-optimal doses of COMPOUND 1 and bortezomib administered together to animals bearing the non-secretory and bortezomib resistant tumor LAGκ-1B were sufficient to produce a significant and sustained therapeutic effect. The elimination of paraprotein-producing LAGκ-1A cells with doses of COMPOUND 1 that allowed continued growth of the tumor supports recent reports suggesting that PIs preferentially kill cells with high Ig secretion (22, 27). In these examples, we have shown that the combination of both PIs is capable of eliminating this non-paraprotein producing population of MM cells.

COMPOUND 1 and bortezomib administered together markedly inhibited both paraprotein secretion and increases in tumor volume. As monotherapy, however, each agent suppressed increases in serum hIgG levels more effectively than their anti-MM effects on tumor volume. Specifically, in LAGκ-1A-bearing animals treated with COMPOUND 1 or bortezomib alone, serum hIgG concentrations stabilized by the 63rd day of treatment, then declined whereas tumor volume continued to increase throughout the duration of the experiment (82 days of treatment) (FIGS. 5A, B). Thus, as previously observed in other studies, single-agent PIs may act primarily against the antibody-secreting mature plasma cell component of MM (22), without affecting the small non-secretory stem cell population responsible for sustaining the tumor (24). Our results suggest that the combination of these two PIs targets both the highly secretory neoplastic plasma cell as well as a population of nonsecretory tumor cells that are resistant to treatment with single-agent PIs.

As with bortezomib, COMPOUND 1 combined with melphalan yields synergistic reduction of MM cell viability in vitro (11, 12, 13). Doses of melphalan that as a single agent permit unimpeded growth of LAGκ-1A prevent tumor progression when added to moderate doses of COMPOUND 1. Furthermore, COMPOUND 1 is capable of chemosensitizing the melphalan-resistant LAGκ-1B tumor. These data are consistent with bortezomib's ability to dramatically reduce the concentration of melphalan required to induce death in chemoresistant MM cells (11). The data presented here suggest that the optimal combination regimen for patients with MM may involve multiple PIs together with chemotherapy. The synergy observed between these agents in vitro further indicates that similar or greater efficacy may be achieved when these two drugs are combined at low doses as compared with standard-dose single-agent therapy. In this way, drug-associated toxicities, such as peripheral neuropathy for bortezomib and myelosuppression for melphalan, may be reduced or avoided (40, 41). In the experiments presented here, mice treated with combination therapies survived similarly to animals treated with single agents; importantly, they experienced little or no tumor progression whereas monotherapy groups had to be euthanized due to high tumor burden.

COMPOUND 1 has favorable therapeutic index, sparing normal human epithelial cells, BM progenitors, BM-derived stromal cells (29), and PBMCs at concentrations that are ten-fold higher than needed to significantly reduce MM cell viability; COMPOUND 1 is effective as a single agent in human MM tumors and is well tolerated; COMPOUND 1 synergizes with bortezomib and melphalan and sensitizes resistant tumors to combination therapy; COMPOUND 1 combined with bortezomib prevents the proliferation of non-secretory and drug-resistant MM cells that may comprise the cancer stem cell population; and, finally, COMPOUND 1 is orally bioavailable. In these studies, oral administration of COMPOUND 1 showed anti-MM effects in all three MM models tested. Compared to control animals, treatment with oral COMPOUND 1 achieved a marked reduction in the growth of LAGκ-1A and similar reductions in the growth of the LAGκ-1B tumors. The potential availability of an oral PI will greatly enhance the convenience of administration of drugs in this class as bortezomib has only shown efficacy when given intravenously twice weekly.

REFERENCES

1. Jemal A, Siegel R, Ward E, et al. Cancer statistics, 2008. CA Cancer J Clin 2008; 58:71-96.
2. Richardson P G, Sonneveld P, Schuster A, et al. Bortezomib demonstrates superior survival compared with high-dose dexamethasone and higher response rates after extended follow-up in the APEX trial in relapsed multiple myeloma. Presented at: 11th Congress of the European Hematology Association; Jun. 15-18, 2006; Amsterdam, the Netherlands. Abstract 224.
3. Chauhan D, Hideshima T, Anderson K C. Targeting proteasomes as therapy in multiple myeloma. Adv Exp Med Biol 2008; 615:251-60.
4. McConkey D J, Zhu K. Mechanisms of proteasome inhibitor action and resistance in cancer. Drug Resist Updat 2008; 11:164-79.
5. Hideshima T, Richardson P, Chauhan D, et al. The proteasome inhibitor PS-341 inhibits growth, induces apoptosis, and overcomes drug resistance in human multiple myeloma cells. Cancer Res 2001; 61:3071-6.
6. Obeng E A, Carlson L M, Gutman D M, Harrington Jr W J, Lee K P, Boise L H. Proteasome inhibitors induce a terminal unfolded protein response in multiple myeloma cells. Blood 2006; 107:4907-16.

7. Chauhan D, Anderson K C. Mechanisms of cell death and survival in multiple myeloma (MM): Therapeutic implications. Apoptosis 2003; 8:337-43.
8. Roccaro A M, Hideshima T, Raje N, et al. Bortezomib mediates antiangiogenesis in multiple myeloma via direct and indirect effects on endothelial cells. Cancer Res 2006; 66:184-91.
9. Richardson P G, Barlogie B, Berenson J, et al. A phase 2 study of bortezomib in relapsed, refractory myeloma. N Engl J Med 2003; 348:2609-17.
10. Jagannath S, Barlogie B, Berenson J, et al. A phase 2 study of two doses of bortezomib in relapsed or refractory myeloma. Br J Haematol 2004; 127:165-72.
11. Ma M H, Yang H H, Parker K, et al. The proteasome inhibitor PS-341 markedly enhances sensitivity of multiple myeloma tumor cells to chemotherapeutic agents. Clin Cancer Res 2003; 9:1136-44.
12. Mitsiades N, Mitsiades C S, Richardson P G, et al. The proteasome inhibitor PS-341 potentiates sensitivity of multiple myeloma cells to conventional chemotherapeutic agents: therapeutic applications. Blood 2003; 101:2377-80.
13. Baumann P, Mandl-Weber S, Oduncu F, Schmidmaier R. Alkylating agents induce activation of NFkappaB in multiple myeloma cells. Leuk Res 2008; 32:1144-7.
14. Mitsiades N, Mitsiades C S, Poulaki V, et al. Apoptotic signaling induced by immunomodulatory thalidomide analogs in human multiple myeloma cells: therapeutic implications. Blood 2002; 99:4525-30.
15. Campbell R A, Sanchez E, Steinberg J A, et al. Antimyeloma effects of arsenic trioxide are enhanced by melphalan, bortezomib and ascorbic acid. Br J Haematol 2007; 138:467-78.
16. Podar K, Raab M S, Zhang J, et al. Targeting PKC in multiple myeloma: in vitro and in vivo effects of the novel, orally available small-molecule inhibitor enzastaurin (LY317615.HCl). Blood 2007; 109:1669-77.
17. Chauhan D, Singh A, Brahmandam M, et al. Combination of proteasome inhibitors bortezomib and NPI-0052 trigger in vivo synergistic cytotoxicity in multiple myeloma. Blood 2008; 111:1654-64.
18. Pei X Y, Dai Y, Grant S. Synergistic induction of oxidative injury and apoptosis in human multiple myeloma cells by the proteasome inhibitor bortezomib and histone deacetylase inhibitors. Clin Cancer Res 2004; 10:3839-52.
19. San Miguel J F, Schlag R, Khuageva N K, et al. Updated follow-up and results of subsequent therapy in the phase III VISTA trial: bortezomib plus melphalan-prednisone versus melphalan-prednisone in newly diagnosed multiple myeloma. Blood (ASH Annual Meeting Abstracts) 2008; 112:650.
20. Berenson J R, Yang H H, Vescio R A, et al. Safety and efficacy of bortezomib and melphalan combination in patients with relapsed or refractory multiple myeloma: updated results of a phase ½ study after longer follow-up. Ann Hematol 2008; 87:623-31.
21. Pineda-Roman M, Zangari M, van Rhee F, et al. VTD combination therapy with bortezomib-thalidomide-dexamethasone is highly effective in advanced and refractory multiple myeloma. Leukemia 2008; 22:1419-27.
22. Bianchi G, Oliva L, Cascio P, et al. The proteasome load versus capacity balance determines apoptotic sensitivity of multiple myeloma cells to proteasome inhibition. Blood 2009; 113:3040-9.
23. Matsui W, Huff C A, Wang Q, et al. Characterization of clonogenic multiple myeloma cells. Blood 2004; 103:2332-6.
24. Matsui W, Wang Q, Barber J P, et al. Clonogenic multiple myeloma progenitors, stem cell properties, and drug resistance. Cancer Res 2008; 68:190-7.
25. Hamburger A, Salmon S E. Primary bioassay of human myeloma stem cells. J Clin Invest 1977; 60:846-54.
26. Pilarski L M, Seeberger K, Coupland R W, et al. Leukemic B cells clonally identical to myeloma plasma cells are myelomagenic in NOD/SCID mice. Exp Hematol 2002; 30:221-8.
27. Meister S, Schubert U, Neubert K, et al. Extensive immunoglobulin production sensitizes myeloma cells for proteasome inhibition. Cancer Res 2007; 67:1783-92.
28. Dorsey B D, Iqbal M, Chatterjee S, et al. Discovery of a potent, selective, and orally active proteasome inhibitor for the treatment of cancer. J Med Chem 2008; 51:1068-72.
29. Piva R, Ruggeri B, Williams M, et al. CEP-18770: a novel orally-active proteasome inhibitor with a tumor-selective pharmacological profile competitive with bortezomib. Blood 2008; 111:2765-75.
30. Chou T C, Talalay P. Quantitative analysis of dose-effect relationships: the combined effects of multiple drugs or enzyme inhibitors. Adv Enzyme Regul 1984; 22:27-55.
31. Chou T C. Theoretical basis, experimental design, and computerized simulation of synergism and antagonism in drug combination studies. Pharmacol Rev 2006; 58:621-81.
32. Campbell R A, Berenson J R. Animal models of multiple myeloma and their utility in drug discovery. In: Current Protocols in Pharmacology, vol. 40, unit 49. Hoboken, N.J.: John Wiley & Sons, Inc.; 2008:14.9.1-22.
33. Berenson J R, Yang H H, Sadler K, et al. Phase I/II trial assessing bortezomib and melphalan combination therapy for the treatment of patients with relapsed or refractory multiple myeloma. J Clin Oncol 2006; 24:937-44.
34. Demo S D, Kirk C J, Aujay M A, et al. Antitumor activity of PR-171, a novel irreversible inhibitor of the proteasome. Cancer Res 2007; 67:6383-91.
35. Crawford L J, Walker B, Ovaa H, et al. Comparative selectivity and specificity of the proteasome inhibitors BzLLLCOCHO, PS-341, and MG-132. Cancer Res 2006; 66:6379-86.
36. Sunters A, Springer C J, Bagshawe K D, Souhami R L, Hartley J A. The cytotoxicity, DNA crosslinking ability and DNA sequence selectivity of the aniline mustards melphalan, chlorambucil and 4-[bis(2-chloroethyl)amino] benzoic acid. Biochem Pharmacol 1992; 44:59-64.
37. Ahn K S, Sethi G, Chao T H, et al. Salinosporamide A (NPI-0052) potentiates apoptosis, suppresses osteoclastogenesis, and inhibits invasion through down-modulation of NF-kappaB regulated gene products. Blood 2007; 110:2286-95.
38. Chen Q, Van der Sluis P C, Boulware D, Hazlehurst L A, Dalton W S. The FA/BRCA pathway is involved in melphalan-induced DNA interstrand cross-link repair and accounts for melphalan resistance in multiple myeloma cells. Blood 2005; 106:698-705.
39. Jacquemont C, Taniguchi T. Proteasome function is required for DNA damage response and fanconi anemia pathway activation. Cancer Res 2007; 67:7395-405.
40. Zweegman S, Huijgens P C. Treatment of myeloma: recent developments. Anticancer Drugs 2002; 13:339-51.
41. Argyriou A A, Iconomou G, Kalofonos H P. Bortezomib-induced peripheral neuropathy in multiple myeloma: a comprehensive review of the literature. Blood 2008; 112:1593-9.

42. VELCADE® Full Prescribing Information
43. ALKERAN® Tablets Prescribing Information; ALKERAN® for Injection Prescribing Information
44. Bissery M-C, Guenard D, Gueritte-Voegelein F, Lavelle F. (1991) Experimental antitumor activity of Taxotere (RP 56976, NSC 628503), a taxol Analogue. *Cancer Research*, 51, 4845-4852.

PREFERRED EMBODIMENTS OF THE PRESENT INVENTION

Embodiment 1

A method for treating multiple myeloma in a subject, comprising the step of administering to the subject a combination of COMPOUND 1 and bortezomib.

Embodiment 2

The method of embodiment 1, wherein the bortezomib is administered as a prodrug.

Embodiment 3

The method of embodiments 1 or 2, wherein the bortezomib is administered intravenously.

Embodiment 4

The method of embodiments 1 or 2, wherein the bortezomib is administered orally.

Embodiment 5

The method of any of embodiments 1 to 4, wherein the bortezomib is administered at a dose in the range of about 0.5 mg/m$^2$ to about 2 mg/m$^2$.

Embodiment 6

The method of embodiment 5, wherein the bortezomib is administered at a dose in the range of about 0.7 mg/m$^2$ to about 1.3 mg/m$^2$.

Embodiment 7

The method of any of embodiments 1 to 6, wherein the bortezomib is administered pursuant to a scheduled dosing cycle in which bortezomib is administered every 3 to 7 days for 2 to 4 weeks, followed by a rest period of about 7 to 21 days during which bortezomib is not administered.

Embodiment 8

The method of embodiment 7, wherein the bortezomib is administered pursuant to a scheduled dosing cycle in which bortezomib is administered on days 1, 4, 8 and 11 of a 21 day cycle.

Embodiment 9

The method of embodiment 7, wherein the bortezomib is administered pursuant to a scheduled dosing cycle in which bortezomib is administered on days 1, 4, 8 and 11 of a 28 day cycle.

Embodiment 10

The method of any of embodiments 7 to 9, wherein the scheduled cycle is repeated at least once.

Embodiment 11

A method for treating multiple myeloma in a subject, comprising the step of administering to the subject a combination of COMPOUND 1 and melphalan.

Embodiment 12

The method according to embodiment 11, wherein the melphalan is administered as a prodrug.

Embodiment 13

The method according to embodiments 11 or 12, wherein the melphalan is administered orally.

Embodiment 14

The method according to embodiments 11 or 12, wherein the melphalan is administered intravenously.

Embodiment 15

The method of any of embodiments 11 to 14, wherein the melphalan is administered at a dose in the range of about 0.025 mg/kg to about 0.5 mg/kg.

Embodiment 16

The method of embodiment 15, wherein the melphalan is administered at a dose in the range of about 0.025 mg/kg to about 0.3 mg/kg.

Embodiment 17

The method of any of embodiments 11 to 16, wherein the melphalan is administered pursuant to a scheduled dosing cycle in which melphalan is administered every 3 to 7 days for 1 to 2 weeks, followed by a rest period of about 4-6 weeks during which melphalan is not administered.

Embodiment 18

The method of embodiment 17, wherein the melphalan is administered pursuant to a scheduled dosing cycle in which melphalan is administered once-daily for about 4 to about 7 days, followed by a rest period of about 4-6 weeks.

Embodiment 19

The method of embodiment 17, wherein the melphalan is administered pursuant to a scheduled dosing cycle in which melphalan is administered once-daily for about 4 to about 5 days, followed by a rest period of about 4-6 weeks.

Embodiment 20

The method of any of embodiments 17 to 19, wherein the scheduled cycle is repeated at least once.

Embodiment 21

The method of any of embodiments 1 to 20, wherein the COMPOUND 1 is administered as a prodrug.

Embodiment 22

The method of embodiment 21, wherein the COMPOUND 1 prodrug is a pharmaceutically acceptable ester form of COMPOUND 1.

Embodiment 23

The method of any of embodiments 1 to 22, wherein the COMPOUND 1 is administered intravenously.

Embodiment 24

The method of any of embodiments 1 to 22, wherein the COMPOUND 1 is administered orally.

Embodiment 25

The method of any of embodiments 1 to 24, wherein the COMPOUND 1 is administered at a dose in the range of about 0.5 mg/m$^2$ to about 5 mg/m$^2$.

Embodiment 26

The method of embodiment 25, wherein the COMPOUND 1 is administered at a dose in the range of about 1 mg/m$^2$ to about 3 mg/m$^2$.

Embodiment 27

The method of embodiment 26, wherein the COMPOUND 1 is administered at a dose of about 1.1 mg/m$^2$.

Embodiment 28

The method of embodiment 26, wherein the COMPOUND 1 is administered at a dose of about 1.5 mg/m$^2$.

Embodiment 29

The method of embodiment 26, wherein the COMPOUND 1 is administered at a dose of about 1.8 mg/m$^2$.

Embodiment 30

The method of embodiment 26, wherein the COMPOUND 1 is administered at a dose of about 2.1 mg/m$^2$.

Embodiment 31

The method of embodiment 26, wherein the COMPOUND 1 is administered at a dose of about 2.4 mg/m$^2$.

Embodiment 32

The method of any of embodiments 1 to 31, wherein the COMPOUND 1 is administered pursuant to a scheduled dosing cycle in which COMPOUND 1 is administered every 3 to 14 days for 2 to 4 weeks, followed by a rest period of about 7 to 21 days during which COMPOUND 1 is not administered.

Embodiment 33

The method of embodiment 32, wherein the COMPOUND 1 is administered pursuant to a scheduled dosing cycle in which COMPOUND 1 is administered on days 1, 4, 8 and 11 of a 21 day cycle.

Embodiment 34

The method of embodiment 32, wherein the COMPOUND 1 is administered pursuant to a scheduled dosing cycle in which COMPOUND 1 is administered on days 1, 4, 8 and 11 of a 28 day cycle.

Embodiment 35

The method of embodiment 32, wherein the COMPOUND 1 is administered pursuant to a scheduled dosing cycle in which COMPOUND 1 is administered on days 1 and 15 of a 21 day cycle.

Embodiment 36

The method of embodiment 32, wherein the COMPOUND 1 is administered pursuant to a scheduled dosing cycle in which COMPOUND 1 is administered on days 1 and 15 of a 28 day cycle.

Embodiment 37

The method of embodiment 32, wherein the COMPOUND 1 is administered pursuant to a scheduled dosing cycle in which COMPOUND 1 is administered on days 1, 8 and 15 of a 28 day cycle.

Embodiment 38

The method of any of embodiments 1 to 6, wherein the bortezomib is administered on days 1, 5 and 9 of a 21 day cycle, and COMPOUND 1 is administered on days 3, 8, and 12 of the 21 day cycle.

Embodiment 39

The method of any of embodiments 1 to 6, wherein the bortezomib is administered on days 1, 5 and 9 of a 28 day cycle, and COMPOUND 1 is administered on days 3, 8, and 12 of the 28 day cycle.

Embodiment 40

The method of any of embodiments 1 to 6, wherein the bortezomib is administered on days 1, 5 and 9 of a 28 day cycle, and COMPOUND 1 is administered on days 1, 8, and 15 of the 28 day cycle.

Embodiment 41

The method of any of embodiments 1 to 6, wherein the bortezomib is administered on days 1, 4, 8 and 11 of a 21 day cycle, and COMPOUND 1 is administered on days 1 and 8 of the 21 day cycle.

Embodiment 42

The method of any of embodiments 1 to 6, wherein the bortezomib is administered on days 1, 4, 8 and 11 of a 28 day cycle, and COMPOUND 1 is administered on days 1, 8 and 15 of the 28 day cycle.

Embodiment 43

The method of any of embodiments 1 to 6, wherein the bortezomib is administered on days 1 and 8 of a 21 day cycle, and COMPOUND 1 is administered on days 1 and 8 of the 21 day cycle.

Embodiment 44

The method of any of embodiments 1 to 6, wherein the bortezomib is administered on days 1 and 8 of a 28 day cycle, and COMPOUND 1 is administered on days 1, 8 and 15 of the 28 day cycle.

Embodiment 45

The method of any of embodiments 1 to 6, wherein the bortezomib is administered on days 1, 8 and 15 of a 28 day cycle, and COMPOUND 1 is administered on days 1, 8 and 15 of the 28 day cycle.

Embodiment 46

The method of any of embodiments 1 to 6, wherein the COMPOUND 1 is administered on days 1, 5 and 9 of a 21 day cycle, and bortezomib is administered on days 3, 8, and 12 of the 21 day cycle.

Embodiment 47

The method of any of embodiments 1 to 6, wherein the COMPOUND 1 is administered on days 1, 5 and 9 of a 28 day cycle, and bortezomib is administered on days 3, 8, and 12 of the 28 day cycle.

Embodiment 48

The method of any of embodiments 1 to 6, wherein the COMPOUND 1 is administered on days 1, 8 and 15 of a 28 day cycle, and bortezomib is administered on days 3, 8, and 12 of the 28 day cycle.

Embodiment 49

The method of any of embodiments 38 to 48, wherein the COMPOUND 1 is administered as a prodrug.

Embodiment 50

The method of embodiment 49, wherein the COMPOUND 1 prodrug is a pharmaceutically acceptable ester form of COMPOUND 1.

Embodiment 51

The method of any of embodiments 38 to 50, wherein the COMPOUND 1 is administered intravenously.

Embodiment 52

The method of any of embodiments 38 to 50, wherein the COMPOUND 1 is administered orally.

Embodiment 53

The method of any of embodiments 38 to 52, wherein the COMPOUND 1 is administered at a dose in the range of about 0.5 mg/m$^2$ to about 5 mg/m$^2$.

Embodiment 54

The method of embodiment 53, wherein the COMPOUND 1 is administered at a dose in the range of about 1 mg/m$^2$ to about 3 mg/m$^2$.

Embodiment 55

The method of embodiment 54, wherein the COMPOUND 1 is administered at a dose of about 1.1 mg/m$^2$.

Embodiment 56

The method of embodiment 54, wherein the COMPOUND 1 is administered at a dose of about 1.5 mg/m$^2$.

Embodiment 57

The method of embodiment 54, wherein the COMPOUND 1 is administered at a dose of about 1.8 mg/m$^2$.

Embodiment 58

The method of embodiment 54, wherein the COMPOUND 1 is administered at a dose of about 2.1 mg/m$^2$.

Embodiment 59

The method of embodiment 54, wherein the COMPOUND 1 is administered at a dose of about 2.4 mg/m$^2$.

Embodiment 60

The method of any of embodiments 32 to 59, wherein the scheduled cycle is repeated at least once.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

All publications referenced herein are incorporated by reference in their entireties for all purposes.

What is claimed:

1. A method for treating bortezomib-resistant multiple myeloma in a subject comprising administering to the subject a combination of COMPOUND 1, or a pharmaceutically acceptable ester of COMPOUND 1, or a prodrug of COMPOUND 1 and bortezomib, or a pharmaceutically acceptable ester of bortezomib, or a prodrug of bortezomib

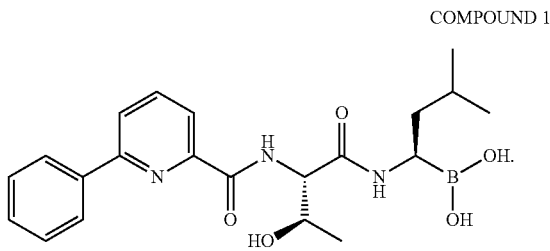 [SMILES: CC(C)C[C@H](NC(=O)[C@@H](NC(=O)c1cccc(-c2ccccc2)n1)[C@@H](C)O)B(O)O]

COMPOUND 1

2. The method of claim 1, wherein the bortezomib is administered as a prodrug.

3. The method of claim 1, wherein the bortezomib is administered at a dose in the range of about 0.5 mg/m$^2$ to about 2 mg/m$^2$.

4. The method of claim 3, wherein the bortezomib is administered at a dose in the range of about 0.7 mg/m$^2$ to about 1.3 mg/m$^2$.

5. The method of claim 1, wherein the bortezomib is administered pursuant to a scheduled dosing cycle in which bortezomib is administered every 3 to 7 days for 2 to 4 weeks, followed by a rest period of about 7 to 21 days during which bortezomib is not administered.

6. The method of claim 5, wherein the bortezomib is administered pursuant to a scheduled dosing cycle in which bortezomib is administered on days 1, 4, 8 and 11 of a 21 day cycle.

7. The method of claim 5, wherein the bortezomib is administered pursuant to a scheduled dosing cycle in which bortezomib is administered on days 1, 4, 8 and 11 of a 28 day cycle.

8. The method of claim 1, wherein the COMPOUND 1 is administered as a prodrug.

9. The method of claim 8, wherein the COMPOUND 1 prodrug is a pharmaceutically acceptable ester form of COMPOUND 1.

10. The method of claim 1, wherein the COMPOUND 1 is administered at a dose in the range of about 0.5 mg/m$^2$ to about 5 mg/m$^2$.

11. The method of claim 10, wherein the COMPOUND 1 is administered at a dose in the range of about 1 mg/m$^2$ to about 3 mg/m$^2$.

12. The method of claim 11, wherein the COMPOUND 1 is administered at a dose of about 1.5 mg/m$^2$.

13. The method of claim 1, wherein the COMPOUND 1 is administered pursuant to a scheduled dosing cycle in which COMPOUND 1 is administered every 3 to 14 days for 2 to 4 weeks, followed by a rest period of about 7 to 21 days during which COMPOUND 1 is not administered.

14. The method of claim 13, wherein the COMPOUND 1 is administered pursuant to a scheduled dosing cycle in which COMPOUND 1 is administered on days 1, 4, 8 and 11 of a 21 day cycle.

15. The method of claim 13, wherein the COMPOUND 1 is administered pursuant to a scheduled dosing cycle in which COMPOUND 1 is administered on days 1, 8 and 15 of a 28 day cycle.

16. The method of claim 15, wherein the scheduled dosing cycle is repeated at least once.

* * * * *